United States Patent
Saus et al.

(10) Patent No.: US 7,147,855 B2
(45) Date of Patent: Dec. 12, 2006

(54) GIPS, A FAMILY OF POLYPEPTIDES WITH TRANSCRIPTION FACTOR ACTIVITY THAT INTERACT WITH GOODPASTURE ANTIGEN BINDING PROTEIN

(76) Inventors: Juan Saus, Amadeo de Saboya 4, 46010, Valencia (ES); Francisco Revert-Ros, C/Sanchis Sivera 27, 6a, 46008, Valencia (ES)

( * ) Notice: Subject to any disclaimer, the term of this patent is extended or adjusted under 35 U.S.C. 154(b) by 340 days.

(21) Appl. No.: 10/309,851

(22) Filed: Dec. 4, 2002

(65) Prior Publication Data

US 2003/0108554 A1  Jun. 12, 2003

Related U.S. Application Data

(60) Provisional application No. 60/382,004, filed on May 20, 2002, provisional application No. 60/338,287, filed on Dec. 7, 2001.

(51) Int. Cl.
- *A61K 39/395* (2006.01)
- *A61K 38/43* (2006.01)
- *C07H 21/04* (2006.01)
- *C12P 21/02* (2006.01)
- *C12N 5/06* (2006.01)

(52) U.S. Cl. .............................. 424/155.1; 424/277.1; 424/94.1; 435/325; 435/320.1; 435/184.1; 435/91.1; 435/69.2; 536/23.2

(58) Field of Classification Search ............. 424/155.1, 424/94.1, 277.1; 435/69.2, 184, 320.1, 91.1, 435/325; 536/23.2
See application file for complete search history.

(56) References Cited

FOREIGN PATENT DOCUMENTS

| WO | WO 00/50607 | 8/2000 |
|----|-------------|--------|
| WO | WO 00/73801 A2 | 12/2000 |
| WO | WO 02/46378 | 6/2002 |
| WO | WO 02/061430 | 8/2002 |

OTHER PUBLICATIONS

See, e.g., Ngo, et al, The Protein Folding Problem and tertiary Structure Prediction, 1994, Merz, et al. (ed.), Birkhauser, Boston, MA, pp. 492-495).*

Copy of search report dated Aug. 12, 2003 for counterpart PCT application No. PCT/EP02/13802.
Genbank Entry Accession No. U53445.
Genseq Entry Accession No. AAG03283.
Genseq Entry Accession No. AAB58157.
Raya et al. (Apr. 30, 1999) "Characterization of a Novel Type of Serine/Threonine Kinase that Specifically Phosphorylates the Human Goodpasture Antigen" *Journal of Biological Chemistry* 274(18): 12642-12649.
Revert et al. (Jun. 2, 1995) "Phosphorylation of the Goodpasture Antigen by Type A Protein Kinases" *Journal of Biological Chemistry* 270(22): 13254-13261.
Raya et al. (Dec. 22, 2000) "Goodpasture Antigen-Binding Protein, the Kinase that Phosphorylates the Goodpasture Antigen, is an Alternatively Spliced Variant Implicated in Autoimmune Pathogenesis" *Journal of Biological Chemistry* 275(51):40392-40399.
EMBL Entry Accession No. AF329092.
Genbank Entry Accession No. BC027860.
Mok, et al., (1994), Gynecol. Oncol., vol. 52(2), pp. 247-252.
Genomic DNA Entry Accession No. NT_030634 for exon I.
Genomic DNA Entry Accession No. NT_033050 for the rest of the exons.
Genbank Entry Accession No. BAC00851.
Genbank Entry Accession No. BAA86589.
Nagano, et al., Nature Cell Biology, (2002), Jul., vol. 4(7), pp. 495-501.

* cited by examiner

*Primary Examiner*—Larry R. Helms
*Assistant Examiner*—Padma Baskar
(74) *Attorney, Agent, or Firm*—McDonnell Boehnen Hulbert & Berghoff LLP

(57) ABSTRACT

The present invention provides isolated GPBP-interacting 90 and 130 kDa polypeptides, and portions thereof (GIP90/130 polypeptides), antibodies to the GIP90/130 polypeptides, and pharmaceutical compositions thereof. The present invention also provides isolated GIP90/130 nucleic acid sequences, expression vectors comprising the nucleic acid sequences, and host cells transfected with the expression vectors. The invention further provides methods for detecting the GIP90/130 polypeptides or nucleic acid sequences, methods for inhibiting interactions between GPBP and GIP90/130 polypeptides, between pol k76 and GIP90/130 polypeptides or aggregation of GIP90/130 polypeptides, and methods for treating patients with autoimmune disorders or cancer.

3 Claims, 6 Drawing Sheets

| EXON | SIZE | INTRON | SIZE |
|------|------|--------|------|
| I | 462 bp | I | 162 kb |
| II | 262 bp | II | 0.9 kb |
| III | 173 bp | III | 5.4 kb |
| IV | 179 bp | IV | 73.2 kb |
| V | 3056 bp | V | 14.8 kb |
| VI | 118 bp | | |

FIGURE 3

```
GIP90     MRSRGSDTEGSAQKKFPRHTKGHSFQGPKNMKHRQQDKDSPSESDVILPCPKAEKPHSGN
GIP130a   MRSRGSDTEGSAQKKFPRHTKGHSFQGPKNMKHRQQDKDSPSESDVILPCPKAEKPHSGN
GIP130b   MRSRGSDTEGSAQKKFPRHTKGHSFQGPKNMKHRQQDKDSPSESDVILPCPKAEKPHSGN
GIP130c   MRSRGSDTEGSAQKKFPRHTKGHSFQGPKNMKHRQQDKDSPSESDVILPCPKAEKPHSGN
SDOC1     ------------------------------------------------------------
DOC1      ------------------------------------------------------------

GIP90     GHQAEDLSRDDLLFLLSILEGELQARDEVIGILKAEKMDLALLEAQYGFVTPKKVLEALQ
GIP130a   GHQAEDLSRDDLLFLLSILEGELQARDEVIGILKAEKMDLALLEAQYGFVTPKKVLEALQ
GIP130b   GHQAEDLSRDDLLFLLSILEGELQARDEVIGILKAEKMDLALLEAQYGFVTPKKVLEALQ
GIP130c   GHQAEDLSRDDLLFLLSILEGELQARDEVIGILKAEKMDLALLEAQYGFVTPKKVLEALQ
SDOC1     ------------------------------------------------------------
DOC1      ------------------------------------------------------------

GIP90     RDAFQAKSTPWQEDIYEKPMNELDKVVEKHKESYRRILGQLLVAEKSRRQTILELEEEKR
GIP130a   RDAFQAKSTPWQEDIYEKPMNELDKVVEKHKESYRRILGQLLVAEKSRRQTILELEEEKR
GIP130b   RDAFQAKSTPWQEDIYEKPMNELDKVVEKHKESYRRILGQLLVAEKSHRQTILELEEEKR
GIP130c   RDAFQAKSTPWQEDIYEKPMNELDKVVEKHKESYRRILGQLLVAEKSRRQTILELEEEKR
SDOC1     ------------------------------------------------------------
DOC1      ------------------------------------------------------------

GIP90     KHKEYMEKSDEFICLLEQECERLKKLIDQEIKSQEEKEQEKEKRVTTLKEELTKLKSFAL
GIP130a   KHKEYMEKSDEFICLLEQECERLKKLIDQEIKSQEEKEQEKEKRVTTLKEELTKLKSFAL
GIP130b   KHKEYMEKSDEFICLLEQECERLKKLIDQEIKSQEEKEQEKEKRVTTLKEELTKLKSFAL
GIP130c   KHKEYMEKSDEFICLLEQECERLKKLIDQEIKSQEEKEQEKEKRVTTLKEELTKLKSFAL
SDOC1     ------------------------------------------------------------
DOC1      ------------------------------------------------------------

GIP90     MVVDEQQRLTAQLTLQRQKIQELTTNAKETHTKLALAEARVQEEEQKATRLEKELQTQTT
GIP130a   MVVDEQQRLTAQLTLQRQKIQELTTNAKETHTKLALAEARVQEEEQKATRLEKELQTQTT
GIP130b   MVVDEQQRLTAQLTLQRQKIQELTTNAKETHTKLALAEARVQEEEQKATRLEKELQTQTT
GIP130c   MVVDEQQRLTAQLTLQRQKIQELTTNAKETHTKLALAEARVQEEEQKATRLEKELQTQTT
SDOC1     MVVDEQQRLTAQLTLQRQKIQELTTNAKETHTKLALAEARVQEEEQKATRLEKELQTQTT
DOC1      MVVDEQQRLTAQLTLQRQKIQELTTNAKETHTKLALAEARVQEEEQKATRLEKELQTQTT
          ************************************************************

GIP90     KFHQDQDTIMAKLTNEDSQNRQLQQKLAALSRQIDELEETNRSLRKAEEELQDIKEKISK
GIP130a   KFHQDQDTIMAKLTNEDSQNRQLQQKLAALSRQIDELEETNRSLRKAEEELQDIKEKISK
GIP130b   KFHQDQDTIMAKLTNEDSQNRQLQQKLAALSRQIDELEETNRSLRKAEEELQDIKEKISK
GIP130c   KFHQDQDTIMAKLTNEDSQNRQLQQKLAALSRQIDELEETNRSLRKAEEELQDIKEKISK
SDOC1     KFHQDQDTIMAKLTNEDSQNRQLQQKLAALSRQIDELEETNRSLRKAEEELQDIKEKISK
DOC1      KFHQDQDTIMAKLTNEDSQNRQLQQKLAALSRQIDELEETNRSLRKAEEELQDIKEKISK
          ************************************************************

GIP90     GEYGNAGIMAEVEELRKRVLDMEGKDEELIKMEEQCRDLNKRLERETLQSKDFKLEVEKL
GIP130a   GEYGNAGIMAEVEELRKRVLDMEGKDEELIKMEEQCRDLNKRLERETLQSKDFKLEVEKL
GIP130b   GEYGNAGIMAEVEELRKRVLDMEGKDEELIKMEEQCRDLNKRLERETLQSKDFKLEVEKL
GIP130c   GEYGNAGIMAEVEELRKRVLDMEGKDEELIKMEEQCRDLNKRLERETLQSKDFKLEVEKL
SDOC1     GEYGNAGIMAEVEELRKRVLDMEGKDEELIKMEEQCRDLNKRLERETLQSKDFKLEVEKL
DOC1      GEYGNAGIMAEVEEL--------------IKMEEQCRDLNKRLERETLQSKDFKLEVEKL
          ***************              ***********************************
```

```
GIP90      SKRIMALEKLEDAFNKSKQECYSLKCNLEKERMTTKQLSQELESLKVRIKELEAIESRLE
GIP130a    SKRIMALEKLEDAFNKSKQECYSLKCNLEKERMTTKQLSQELESLKVRIKELEAIESRLE
GIP130b    SKRIMALEKLEDAFNKSKQECYSLKCNLEKERMTTKQLSQELESLKVRIKELEAIESRLE
GIP130c    SKRIMALEKLEDAFNKSKQECYSLKCNLEKERMTTKQLSQELESLKVRIKELEAIESRLE
SDOC1      SKRIMALEKLEDAFNKSKQECYSLKCNLEKERMTTKQLSQELESLKVRIKELEAIESRLE
DOC1       SKRIMALEKLEDAFNKSKQECYSLKCNLEKERMTTKQLSQELESLKVRIKELEAIESRLE
           ************************************************************

GIP90      KTEFTLKEDLTKLKTLTVMFVDERKTMSEKLKKTEDKLQAASSQLQVEQNKVTTVTEKLI
GIP130a    KTEFTLKEDLTKLKTLTVMFVDERKTMSEKLKKTEDKLQAASSQLQVEQNKVTTVTEKLI
GIP130b    KTEFTLKEDLTKLKTLTVMFVDERKTMSEKLKKTEDKLQAASSQLQVEQNKVTTVTEKLI
GIP130c    KTEFTLKEDLTKLKTLTVMFVDERKTMSEKLKKTEDKLQAASSQLQVEQNKVTTVTEKLI
SDOC1      KTEFTLKEDLTKLKTLTVMFVDERKTMSEKLKKTEDKLQAASSQLQVEQNKVTTVTEKLI
DOC1       KTEFTLKEDLTKLKTLTVMFVDERKTMSEKLKKTEDKLQAASSQLQVEQNKVTTVTEKLI
           ************************************************************

GIP90      EETKRALKSKTDVEEKMYSVTKERDDLKNKLKAEEEKGNDLLSRVNMLKNRLQSLEAIEK
GIP130a    EETKRALKSKTDVEEKMYSVTKERDDLKNKLKAEEEKGNDLLSRVNMLKNRLQSLEAIEK
GIP130b    EETKRALKSKTDVEEKMYSVTKERDDLKNKLKAEEEKGNDLLSRVNMLKNRLQSLEAIEK
GIP130c    EETKRALKSKTDVEEKMYSVTKERDDLKNKLKAEEEKGNDLLSRVNMLKNRLQSLEAIEK
SDOC1      EETKRALKSKTDVEEKMYSVTKERDDLKNKLKAEEEKGNDLLSRVNMLKNRLQSLEAIEK
DOC1       EETKRALKSKTDVEEKMYSVTKERDDLKNKLKAEEEKGNDLLSRVNMLKNRLQSLEAIEK
           ************************************************************

GIP90      DFLKNKLNQDSGKSTTALHQENNKIKELSQEVERLKLKLKDMKAIEDDLMKTEDEYETLE
GIP130a    DFLKNKLNQDSGKSTTALHQENNKIKELSQEVERLKLKLKDMKAIEDDLMKTEDEYETLE
GIP130b    DFLKNKLNQDSGKSTTALHQENNKIKELSQEVERLKLKLKDMKAIEDDLMKTEDEYETLE
GIP130c    DFLKNKLNQDSGKSTTALHQENNKIKELSQEVERLKLKLKDMKAIEDDLMKTEDEYETLE
SDOC1      DFLKNKLNQDSGKSTTALHQENNKIKELSQEVERLKLKLKDMKAIEDDLMKTEDEYETLE
DOC1       DFLKNKLNQDSGKSTTALHQENNKIKELSQEVERLKLKLKDMKAIEDDLMKTEDEYETLE
           ************************************************************

GIP90      RRYANERDKAQFLSKELEHVKMELAKYKLAEKTETSHEQWLFKRLQEEEAKSGHLSREVD
GIP130a    RRYANERDKAQFLSKELEHVKMELAKYKLAEKTETSHEQWLFKRLQEEEAKSGHLSREVD
GIP130b    RRYANERDKAQFLSKELEHVKMELAKYKLAEKTETSHEQWLFKRLQEEEAKSGHLSREVD
GIP130c    RRYANERDKAQFLSKELEHVKMELAKYKLAEKTETSHEQWLFKRLQEEEAKSGHLSREVD
SDOC1      RRYANERDKAQFLSKELEHVKMELAKYKLAEKTETSHEQWLFKRLQEEEAKSGHLSREVD
DOC1       RRYANERDKAQFLSKELEHVKMELAKYKLAEKTETSHEQWLFKRLQEEEAKSGHLSREVD
           ************************************************************

GIP90      ALKEKIHEYMATEDLICHLQGDHSVLQKKTKSTRKQEQRFRKRD----------------
GIP130a    ALKEKIHEYMATEDLICHLQGDHSVLQKKLNQQENRNRDLGREIENLTKELERYRHFSKS
GIP130b    ALKEKIHEYMATEDLICHLQGDHSVLQKKLNQQENRNRDLGREIENLTKELERYRHFSKS
GIP130c    ALKEKIHEYMATEDLICHLQGDHSVLQKKLNQQENRNRDLGREIENLTKELERYRHFSKS
SDOC1      ALKEKIHEYMATEDLICHLQGDHSVLQKKLNQQENRNRDLGREIENLTKELERYRHFSKS
DOC1       ALKEKIHEYMATEDLICHLQGDHSVCKKKLNQQENRNRDLGREIENLTKELERYRHFSKS
           ************************ **  ..          :     :*:*:  .

GIP90      ------------------------------------------------------------
GIP130a    LRPSLNGRRISDPQVFSKEVQTEAVDNEPPDYKSLIPLERAVINGQLYEESENQDEDPND
GIP130b    LRPSLNGRRISDPQVFSKEVQTEAVDNEPPDYKSLIPLERAVINGQLYEESENQDEDPND
GIP130c    LRPSLNGRRISDPQVFSKEVQTEAVDNEPPDYKSLIPLERAVINGQLYEESENQDEDPND
SDOC1      LRPSLNGRRISDPQVFSKEVQTEAVDNEPPDYKSLIPLERAVINGQLYEESENQDEDPND
DOC1       LRPSLNGRRISDPQVFSKEVQTEAVDNEPPDYKSLIPLERAVINGQLYEESENQDEDPND
```

```
GIP90    ----------------------------------------------------------------
GIP130a  EGSVLSFKCSQSTPCPVNRKLWIPWMKSKEGHLQNGKMQTKPNANFVQPGDLVLSHTPGQ
GIP130b  EGSVLSFKCSQSTPCPVNRKLWIPWMKSKEGHLQNGKMQTKPNANFVQPGDLVLSHTPGQ
GIP130c  EGSVLSFKCSQSTPCPVNRKLWIPWMKSKEGHLQNGKMQTKPNANFVQPGDLVLSHTPGQ
SDOC1    EGSVLSFKCSQSTPCPVNRKLWIPWMKSKEGHLQNGKMQTKPNANFVQPGDLVLSHTPGQ
DOC1     EGSVLSFKCSQSTPCPVNRKLWIPWMKSKEGHLQNGKMQTKPNANFVQPGDLVLSHTPGQ

GIP90    ----------------------------------------------------------------
GIP130a  PLHIKVTPDHVQNTATLEITSPTTESPHSYTSTAVIPNCGTPKQRITILQNASITPVKSK
GIP130b  PLHIKVTPDHVQNTATLEITSPTTESPHSYTSTAVIPNCGTPKQRITILQNASITPVKSK
GIP130c  PLHIKVTPDHVQNTATLEITSPTTESPHSYTSTAVIPNCGTPKQRITILQNASITPVKSK
SDOC1    PLHIKVTPDHVQNTATLEITSPTTESPHSYTSTAVIPNCGTPKQRITILQNASITPVKSK
DOC1     PLHIKVTPDHVQNTATLEITSPTTESPHSYTSTAVIPNCGTPKQRITILQNASITPVKSK

GIP90    ----------------------------------------------------------------
GIP130a  TSTEDLMNLEQGMSPITMATFARAQTPESCGSLTPERTMSPIQVLAVTGSASSPEQGRSP
GIP130b  TSTEDLMNLEQGMSPITMATFARAQTPESCGSLTPERTMSPIQVLAVTGSASSPEQGRSP
GIP130c  TSTEDLMNLEQGMSPITMATFARAQTPESCGSLTPERTMSPIQVLAVTGSASSPEQGRSP
SDOC1    TSTEDLMNLEQGMSPITMATFARAQTPESCGSLTPERTMSPIQVLAVTGSASSPEQGRSP
DOC1     TSTEDLMNLEQGMSPITMATFARAQTPESCGSLTPERTMSLFRFWL--------------

GIP90    ----------------------------------------------------------------
GIP130a  EPTEISAKHAIFRVSPDRQSSWQFQRSNSNSSSVITTEDNKIHIHLGSPYMQAVASPVRP
GIP130b  EPTEISAKHAIFRVSPDRQSSWQFQRSNSNSSSVITTEDNKIHIHLGSPYMQAVASPVRP
GIP130c  EPTEISAKHAIFRVSPDRQSSWQFQRSNSNSSSVITTEDNKIHIHLGSPYMQAVASPVRP
SDOC1    EPTEISAKHAIFRVSPDRQSSWQFQRSNSNSSSVITTEDNKIHIHLGSPYMQAVASPVRP
DOC1     ----------------------------------------------------------------

GIP90    ----------------------------------------------------------------
GIP130a  ASPSAPLQDNRTQGLINGALNKTTNKVTSSITITPTATPLPRQSQITVEPLLLPH
GIP130b  ASPSAPLQDNRTQGLINGALNKTTNKVTSSITITPTATPLPRQSQITVSNIYN--
GIP130c  ASPSAPLQDNRTQXLINGALNKTTNKVTSSITITPTATPLPRQSQITVSNIYN--
SDOC1    ASPSAPLQDNRTQGLINGALNKTTNKVTSSITITPTATPLPRQSQITVSNIYN--
DOC1     ----------------------------------------------------------------
```

FIGURE 4

RDEVIGILKAEKMDLALLEAQYGFVTPKKVLEALQRDAFQAKSTPWQEDIYEKPMNE<u>ld</u>

<u>kvvekhke</u>SYRRILGQLLVAEKSRRQTILELEEEKRKHKEYMEKSDEFICLLEQECERL

KKLIDQEIKSQEEKEQEKEKRVTTLKEELTKLKSFALMVVDEQQRLTAQLTLQRQKIQE

LTTNAKETHTklalaearvqeeeqkatrleKELQTQTTKFHQDQDTIMAKLTNEDSQNR

QLQQKLAALSRQIDELEETNRSLRKAEEE

SEQUENCE LISTING

<160> NUMBER OF SEQ ID NOS: 38

<210> SEQ ID NO 1
<211> LENGTH: 30
<212> TYPE: DNA
<213> ORGANISM: Homo sapiens
<220> FEATURE:
<221> NAME/KEY: CDS
<222> LOCATION: (1)..(30)
<223> OTHER INFORMATION:

<400> SEQUENCE: 1

| tct | tac | aga | cga | atc | ctg | gga | cag | ctt | tta | | 30 |
|-----|-----|-----|-----|-----|-----|-----|-----|-----|-----|---|----|
| Ser | Tyr | Arg | Arg | Ile | Leu | Gly | Gln | Leu | Leu | | |
| 1 | | | | 5 | | | | | 10 | | |

<210> SEQ ID NO 2
<211> LENGTH: 10
<212> TYPE: PRT
<213> ORGANISM: Homo sapiens

<400> SEQUENCE: 2

Ser Tyr Arg Arg Ile Leu Gly Gln Leu Leu
1               5                   10

<210> SEQ ID NO 3
<211> LENGTH: 720
<212> TYPE: DNA
<213> ORGANISM: Homo sapiens
<220> FEATURE:
<221> NAME/KEY: CDS
<222> LOCATION: (1)..(720)
<223> OTHER INFORMATION:

<400> SEQUENCE: 3

| atg | cgt | tcc | aga | ggc | agt | gat | acc | gag | ggc | tca | gcc | caa | aag | aaa | ttt | 48 |
|-----|-----|-----|-----|-----|-----|-----|-----|-----|-----|-----|-----|-----|-----|-----|-----|----|
| Met | Arg | Ser | Arg | Gly | Ser | Asp | Thr | Glu | Gly | Ser | Ala | Gln | Lys | Lys | Phe | |
| 1 | | | | 5 | | | | | 10 | | | | | 15 | | |

| cca | aga | cat | act | aaa | ggc | cac | agt | ttc | caa | ggg | cct | aaa | aac | atg | aag | 96 |
|-----|-----|-----|-----|-----|-----|-----|-----|-----|-----|-----|-----|-----|-----|-----|-----|----|
| Pro | Arg | His | Thr | Lys | Gly | His | Ser | Phe | Gln | Gly | Pro | Lys | Asn | Met | Lys | |
| | | | 20 | | | | | 25 | | | | | 30 | | | |

| cat | aga | cag | caa | gac | aaa | gac | tcc | ccc | agt | gag | tcg | gat | gta | ata | ctt | 144 |
|-----|-----|-----|-----|-----|-----|-----|-----|-----|-----|-----|-----|-----|-----|-----|-----|-----|
| His | Arg | Gln | Gln | Asp | Lys | Asp | Ser | Pro | Ser | Glu | Ser | Asp | Val | Ile | Leu | |
| | | 35 | | | | | 40 | | | | | 45 | | | | |

| ccg | tgt | ccc | aag | gca | gag | aag | cca | cac | agt | ggt | aat | ggc | cac | caa | gca | 192 |
|-----|-----|-----|-----|-----|-----|-----|-----|-----|-----|-----|-----|-----|-----|-----|-----|-----|
| Pro | Cys | Pro | Lys | Ala | Glu | Lys | Pro | His | Ser | Gly | Asn | Gly | His | Gln | Ala | |
| 50 | | | | | 55 | | | | | 60 | | | | | | |

| gaa | gac | ctc | tca | aga | gat | gac | ctg | tta | ttt | ctc | ctc | agc | att | ctg | gag | 240 |
|-----|-----|-----|-----|-----|-----|-----|-----|-----|-----|-----|-----|-----|-----|-----|-----|-----|
| Glu | Asp | Leu | Ser | Arg | Asp | Asp | Leu | Leu | Phe | Leu | Leu | Ser | Ile | Leu | Glu | |
| 65 | | | | 70 | | | | | 75 | | | | | 80 | | |

| gga | gaa | ctg | cag | gct | cga | gat | gag | gtc | ata | ggc | att | tta | aag | gct | gaa | 288 |
|-----|-----|-----|-----|-----|-----|-----|-----|-----|-----|-----|-----|-----|-----|-----|-----|-----|
| Gly | Glu | Leu | Gln | Ala | Arg | Asp | Glu | Val | Ile | Gly | Ile | Leu | Lys | Ala | Glu | |
| | | | 85 | | | | | 90 | | | | | 95 | | | |

| aaa | atg | gac | ctg | gct | ttg | ctg | gaa | gct | cag | tat | ggg | ttt | gtc | act | cca | 336 |
|-----|-----|-----|-----|-----|-----|-----|-----|-----|-----|-----|-----|-----|-----|-----|-----|-----|
| Lys | Met | Asp | Leu | Ala | Leu | Leu | Glu | Ala | Gln | Tyr | Gly | Phe | Val | Thr | Pro | |
| | | | 100 | | | | | 105 | | | | | 110 | | | |

| aaa | aag | gtg | tta | gag | gct | ctc | cag | aga | gat | gct | ttt | caa | gcg | aaa | tct | 384 |
|-----|-----|-----|-----|-----|-----|-----|-----|-----|-----|-----|-----|-----|-----|-----|-----|-----|
| Lys | Lys | Val | Leu | Glu | Ala | Leu | Gln | Arg | Asp | Ala | Phe | Gln | Ala | Lys | Ser | |
| | | | 115 | | | | | 120 | | | | | 125 | | | |

| acc | cct | tgg | cag | gag | gac | atc | tat | gag | aaa | cca | atg | aat | gag | ttg | gac | 432 |
|-----|-----|-----|-----|-----|-----|-----|-----|-----|-----|-----|-----|-----|-----|-----|-----|-----|
| Thr | Pro | Trp | Gln | Glu | Asp | Ile | Tyr | Glu | Lys | Pro | Met | Asn | Glu | Leu | Asp | |
| | 130 | | | | | 135 | | | | | 140 | | | | | |

| aaa | gtt | gtg | gaa | aaa | cat | aaa | gaa | tct | tac | aga | cga | atc | ctg | gga | cag | 480 |
|-----|-----|-----|-----|-----|-----|-----|-----|-----|-----|-----|-----|-----|-----|-----|-----|-----|
| Lys | Val | Val | Glu | Lys | His | Lys | Glu | Ser | Tyr | Arg | Arg | Ile | Leu | Gly | Gln | |
| 145 | | | | | 150 | | | | | 155 | | | | | 160 | |

| ctt | tta | gtg | gca | gaa | aaa | tcc | cgt | agg | caa | acc | ata | ttg | gag | ttg | gag | 528 |

```
Leu Leu Val Ala Glu Lys Ser Arg Arg Gln Thr Ile Leu Glu Leu Glu
            165                 170                 175 gaa aag aga aaa cat aaa gaa tac atg gag aag agt gat gaa ttc        576
Glu Glu Lys Arg Lys His Lys Glu Tyr Met Glu Lys Ser Asp Glu Phe
        180                 185                 190 ata tgc cta cta gaa cag gaa tgt gaa aga tta aag aag cta att gat    624
Ile Cys Leu Leu Glu Gln Glu Cys Glu Arg Leu Lys Lys Leu Ile Asp
            195                 200                 205 caa gaa atc aag tct cag gag gag aag gag caa gaa aag gag aaa agg    672
Gln Glu Ile Lys Ser Gln Glu Glu Lys Glu Gln Glu Lys Glu Lys Arg
            210                 215                 220 gtc acc acc ctg aaa gag gag ctg acc aag ctg aag tct ttt gct ttg    720
Val Thr Thr Leu Lys Glu Glu Leu Thr Lys Leu Lys Ser Phe Ala Leu
225                 230                 235                 240
```

<210> SEQ ID NO 4
<211> LENGTH: 240
<212> TYPE: PRT
<213> ORGANISM: Homo sapiens

<400> SEQUENCE: 4

Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Asp Leu Leu Phe Leu Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

Thr Pro Trp Gln Glu Asp Ile Tyr Glu Lys Pro Met Asn Glu Leu Asp
    130                 135                 140

Lys Val Val Glu Lys His Lys Glu Ser Tyr Arg Arg Ile Leu Gly Gln
145                 150                 155                 160

Leu Leu Val Ala Glu Lys Ser Arg Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205

Gln Glu Ile Lys Ser Gln Glu Glu Lys Glu Gln Glu Lys Glu Lys Arg
    210                 215                 220

Val Thr Thr Leu Lys Glu Glu Leu Thr Lys Leu Lys Ser Phe Ala Leu
225                 230                 235                 240

<210> SEQ ID NO 5
<211> LENGTH: 795
<212> TYPE: DNA
<213> ORGANISM: Homo sapiens
<220> FEATURE:
<221> NAME/KEY: CDS

```
<222> LOCATION: (1)..(795)
<223> OTHER INFORMATION:

<400> SEQUENCE: 5 cga gat gag gtc ata ggc att tta aag gct gaa aaa atg gac ctg gct    48
Arg Asp Glu Val Ile Gly Ile Leu Lys Ala Glu Lys Met Asp Leu Ala
1               5                   10                  15 ttg ctg gaa gct cag tat ggg ttt gtc act cca aaa aag gtg tta gag    96
Leu Leu Glu Ala Gln Tyr Gly Phe Val Thr Pro Lys Lys Val Leu Glu
            20                  25                  30 gct ctc cag aga gat gct ttt caa gcg aaa tct acc cct tgg cag gag   144
Ala Leu Gln Arg Asp Ala Phe Gln Ala Lys Ser Thr Pro Trp Gln Glu
        35                  40                  45 gac atc tat gag aaa cca atg aat gag ttg gac aaa gtt gtg gaa aaa   192
Asp Ile Tyr Glu Lys Pro Met Asn Glu Leu Asp Lys Val Val Glu Lys
    50                  55                  60 cat aaa gaa tct tac aga cga atc ctg gga cag ctt tta gtg gca gaa   240
His Lys Glu Ser Tyr Arg Arg Ile Leu Gly Gln Leu Leu Val Ala Glu
65                  70                  75                  80 aaa tcc cgt agg caa acc ata ttg gag ttg gag gaa gaa aag aga aaa   288
Lys Ser Arg Arg Gln Thr Ile Leu Glu Leu Glu Glu Glu Lys Arg Lys
                85                  90                  95 cat aaa gaa tac atg gag aag agt gat gaa ttc ata tgc cta cta gaa   336
His Lys Glu Tyr Met Glu Lys Ser Asp Glu Phe Ile Cys Leu Leu Glu
            100                 105                 110 cag gaa tgt gaa aga tta aag aag cta att gat caa gaa atc aag tct   384
Gln Glu Cys Glu Arg Leu Lys Lys Leu Ile Asp Gln Glu Ile Lys Ser
        115                 120                 125 cag gag gag aag gag caa gaa aag gag aaa agg gtc acc acc ctg aaa   432
Gln Glu Glu Lys Glu Gln Glu Lys Glu Lys Arg Val Thr Thr Leu Lys
    130                 135                 140 gag gag ctg acc aag ctg aag tct ttt gct ttg atg gtg gtg gat gaa   480
Glu Glu Leu Thr Lys Leu Lys Ser Phe Ala Leu Met Val Val Asp Glu
145                 150                 155                 160 cag caa agg ctg acg gca cag ctc acc ctt caa aga cag aaa atc caa   528
Gln Gln Arg Leu Thr Ala Gln Leu Thr Leu Gln Arg Gln Lys Ile Gln
                165                 170                 175 gag ctg acc aca aat gca aag gaa aca cat acc aaa cta gcc ctt gct   576
Glu Leu Thr Thr Asn Ala Lys Glu Thr His Thr Lys Leu Ala Leu Ala
            180                 185                 190 gaa gcc aga gtt cag gag gaa gag cag aag gca acc aga cta gag aag   624
Glu Ala Arg Val Gln Glu Glu Glu Gln Lys Ala Thr Arg Leu Glu Lys
        195                 200                 205 gaa ctg caa acg cag acc aca aag ttt cac caa gac caa gac aca att   672
Glu Leu Gln Thr Gln Thr Thr Lys Phe His Gln Asp Gln Asp Thr Ile
    210                 215                 220 atg gcg aag ctc acc aat gag gac agt caa aat cgc cag ctt caa caa   720
Met Ala Lys Leu Thr Asn Glu Asp Ser Gln Asn Arg Gln Leu Gln Gln
225                 230                 235                 240 aag ctg gca gca ctc agc cgg cag att gat gag tta gaa gag aca aac   768
Lys Leu Ala Ala Leu Ser Arg Gln Ile Asp Glu Leu Glu Glu Thr Asn
                245                 250                 255 agg tct tta cga aaa gca gaa gag gag                               795
Arg Ser Leu Arg Lys Ala Glu Glu Glu
            260                 265

<210> SEQ ID NO 6
<211> LENGTH: 265
<212> TYPE: PRT
<213> ORGANISM: Homo sapiens
```

```
<400> SEQUENCE: 6

Arg Asp Glu Val Ile Gly Ile Leu Lys Ala Glu Lys Met Asp Leu Ala
1               5                   10                  15

Leu Leu Glu Ala Gln Tyr Gly Phe Val Thr Pro Lys Lys Val Leu Glu
            20                  25                  30

Ala Leu Gln Arg Asp Ala Phe Gln Ala Lys Ser Thr Pro Trp Gln Glu
        35                  40                  45

Asp Ile Tyr Glu Lys Pro Met Asn Glu Leu Asp Lys Val Val Glu Lys
    50                  55                  60

His Lys Glu Ser Tyr Arg Arg Ile Leu Gly Gln Leu Leu Val Ala Glu
65                  70                  75                  80

Lys Ser Arg Arg Gln Thr Ile Leu Glu Leu Glu Glu Lys Arg Lys
                85                  90                  95

His Lys Glu Tyr Met Glu Lys Ser Asp Glu Phe Ile Cys Leu Leu Glu
                100                 105                 110

Gln Glu Cys Glu Arg Leu Lys Lys Leu Ile Asp Gln Glu Ile Lys Ser
            115                 120                 125

Gln Glu Glu Lys Glu Gln Glu Lys Glu Lys Arg Val Thr Thr Leu Lys
        130                 135                 140

Glu Glu Leu Thr Lys Leu Lys Ser Phe Ala Leu Met Val Val Asp Glu
145                 150                 155                 160

Gln Gln Arg Leu Thr Ala Gln Leu Thr Leu Gln Arg Gln Lys Ile Gln
                165                 170                 175

Glu Leu Thr Thr Asn Ala Lys Glu Thr His Thr Lys Leu Ala Leu Ala
            180                 185                 190

Glu Ala Arg Val Gln Glu Glu Gln Lys Ala Thr Arg Leu Glu Lys
        195                 200                 205

Glu Leu Gln Thr Gln Thr Thr Lys Phe His Gln Asp Gln Asp Thr Ile
    210                 215                 220

Met Ala Lys Leu Thr Asn Glu Asp Ser Gln Asn Arg Gln Leu Gln Gln
225                 230                 235                 240

Lys Leu Ala Ala Leu Ser Arg Gln Ile Asp Glu Leu Glu Glu Thr Asn
                245                 250                 255

Arg Ser Leu Arg Lys Ala Glu Glu Glu
            260                 265

<210> SEQ ID NO 7
<211> LENGTH: 1050
<212> TYPE: DNA
<213> ORGANISM: Homo sapiens
<220> FEATURE:
<221> NAME/KEY: CDS
<222> LOCATION: (1)..(1050)
<223> OTHER INFORMATION:

<400> SEQUENCE: 7 atg cgt tcc aga ggc agt gat acc gag ggc tca gcc caa aag aaa ttt      48
Met Arg Ser Arg Gly Ser Asp Thr Glu Gly Ser Ala Gln Lys Lys Phe
1               5                   10                  15 cca aga cat act aaa ggc cac agt ttc caa ggg cct aaa aac atg aag      96
Pro Arg His Thr Lys Gly His Ser Phe Gln Gly Pro Lys Asn Met Lys
            20                  25                  30 cat aga cag caa gac aaa gac tcc ccc agt gag tcg gat gta ata ctt     144
His Arg Gln Gln Asp Lys Asp Ser Pro Ser Glu Ser Asp Val Ile Leu
        35                  40                  45 ccg tgt ccc aag gca gag aag cca cac agt ggt aat ggc cac caa gca     192
Pro Cys Pro Lys Ala Glu Lys Pro His Ser Gly Asn Gly His Gln Ala
```

```
              50                  55                  60
gaa gac ctc tca aga gat gac ctg tta ttt ctc ctc agc att ctg gag     240
Glu Asp Leu Ser Arg Asp Asp Leu Leu Phe Leu Leu Ser Ile Leu Glu
 65                  70                  75                  80 gga gaa ctg cag gct cga gat gag gtc ata ggc att tta aag gct gaa     288
Gly Glu Leu Gln Ala Arg Asp Glu Val Ile Gly Ile Leu Lys Ala Glu
             85                  90                  95 aaa atg gac ctg gct ttg ctg gaa gct cag tat ggg ttt gtc act cca     336
Lys Met Asp Leu Ala Leu Leu Glu Ala Gln Tyr Gly Phe Val Thr Pro
            100                 105                 110 aaa aag gtg tta gag gct ctc cag aga gat gct ttt caa gcg aaa tct     384
Lys Lys Val Leu Glu Ala Leu Gln Arg Asp Ala Phe Gln Ala Lys Ser
            115                 120                 125 acc cct tgg cag gag gac atc tat gag aaa cca atg aat gag ttg gac     432
Thr Pro Trp Gln Glu Asp Ile Tyr Glu Lys Pro Met Asn Glu Leu Asp
        130                 135                 140 aaa gtt gtg gaa aaa cat aaa gaa tct tac aga cga atc ctg gga cag     480
Lys Val Val Glu Lys His Lys Glu Ser Tyr Arg Arg Ile Leu Gly Gln
145                 150                 155                 160 ctt tta gtg gca gaa aaa tcc cgt agg caa acc ata ttg gag ttg gag     528
Leu Leu Val Ala Glu Lys Ser Arg Arg Gln Thr Ile Leu Glu Leu Glu
                165                 170                 175 gaa gaa aag aga aaa cat aaa gaa tac atg gag aag agt gat gaa ttc     576
Glu Glu Lys Arg Lys His Lys Glu Tyr Met Glu Lys Ser Asp Glu Phe
            180                 185                 190 ata tgc cta cta gaa cag gaa tgt gaa aga tta aag aag cta att gat     624
Ile Cys Leu Leu Glu Gln Glu Cys Glu Arg Leu Lys Lys Leu Ile Asp
        195                 200                 205 caa gaa atc aag tct cag gag gag aag gag caa gaa aag gag aaa agg     672
Gln Glu Ile Lys Ser Gln Glu Glu Lys Glu Gln Glu Lys Glu Lys Arg
210                 215                 220 gtc acc acc ctg aaa gag gag ctg acc aag ctg aag tct ttt gct ttg     720
Val Thr Thr Leu Lys Glu Glu Leu Thr Lys Leu Lys Ser Phe Ala Leu
                225                 230                 235                 240 atg gtg gtg gat gaa cag caa agg ctg acg gca cag ctc acc ctt caa     768
Met Val Val Asp Glu Gln Gln Arg Leu Thr Ala Gln Leu Thr Leu Gln
            245                 250                 255 aga cag aaa atc caa gag ctg acc aca aat gca aag gaa aca cat acc     816
Arg Gln Lys Ile Gln Glu Leu Thr Thr Asn Ala Lys Glu Thr His Thr
        260                 265                 270 aaa cta gcc ctt gct gaa gcc aga gtt cag gag gaa gag cag aag gca     864
Lys Leu Ala Leu Ala Glu Ala Arg Val Gln Glu Glu Glu Gln Lys Ala
    275                 280                 285 acc aga cta gag aag gaa ctg caa acg cag acc aca aag ttt cac caa     912
Thr Arg Leu Glu Lys Glu Leu Gln Thr Gln Thr Thr Lys Phe His Gln
290                 295                 300 gac caa gac aca att atg gcg aag ctc acc aat gag gac agt caa aat     960
Asp Gln Asp Thr Ile Met Ala Lys Leu Thr Asn Glu Asp Ser Gln Asn
305                 310                 315                 320 cgc cag ctt caa caa aag ctg gca gca ctc agc cgg cag att gat gag    1008
Arg Gln Leu Gln Gln Lys Leu Ala Ala Leu Ser Arg Gln Ile Asp Glu
            325                 330                 335 tta gaa gag aca aac agg tct tta cga aaa gca gaa gag gag             1050
Leu Glu Glu Thr Asn Arg Ser Leu Arg Lys Ala Glu Glu Glu
        340                 345                 350

<210> SEQ ID NO 8
<211> LENGTH: 350
<212> TYPE: PRT
<213> ORGANISM: Homo sapiens
```

<400> SEQUENCE: 8

```
Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Leu Leu Phe Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

Thr Pro Trp Gln Glu Asp Ile Tyr Glu Lys Pro Met Asn Glu Leu Asp
    130                 135                 140

Lys Val Val Glu Lys His Lys Glu Ser Tyr Arg Arg Ile Leu Gly Gln
145                 150                 155                 160

Leu Leu Val Ala Glu Lys Ser Arg Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205

Gln Glu Ile Lys Ser Gln Glu Glu Lys Glu Gln Glu Lys Glu Lys Arg
    210                 215                 220

Val Thr Thr Leu Lys Glu Glu Leu Thr Lys Leu Lys Ser Phe Ala Leu
225                 230                 235                 240

Met Val Val Asp Glu Gln Arg Leu Thr Ala Gln Leu Thr Leu Gln
                245                 250                 255

Arg Gln Lys Ile Gln Glu Leu Thr Thr Asn Ala Lys Glu Thr His Thr
            260                 265                 270

Lys Leu Ala Leu Ala Glu Ala Arg Val Gln Glu Glu Gln Lys Ala
        275                 280                 285

Thr Arg Leu Glu Lys Glu Leu Gln Thr Gln Thr Lys Phe His Gln
    290                 295                 300

Asp Gln Asp Thr Ile Met Ala Lys Leu Thr Asn Glu Asp Ser Gln Asn
305                 310                 315                 320

Arg Gln Leu Gln Gln Lys Leu Ala Ala Leu Ser Arg Gln Ile Asp Glu
                325                 330                 335

Leu Glu Glu Thr Asn Arg Ser Leu Arg Lys Ala Glu Glu Glu
            340                 345                 350
```

<210> SEQ ID NO 9
<211> LENGTH: 3998
<212> TYPE: DNA
<213> ORGANISM: Homo sapiens
<220> FEATURE:
<221> NAME/KEY: CDS
<222> LOCATION: (473)..(2767)
<223> OTHER INFORMATION:
<220> FEATURE:

-continued

```
<221> NAME/KEY: misc_feature
<223> OTHER INFORMATION: GIP90

<400> SEQUENCE: 9
cacacacaca cacacacaca gacgtgctca cggagcctgt gcctgcctct acttgtctgc    60
tctgcgcaga tggttcctgg cttttgggtc acctcatcct gcagcccagt ccagttagaa   120
cctttcttcc acagagactg gcaagctgtg gggtaagagt tttggtaagg ctgcctgtct   180
tcagagcatg aaggacactg cccggagagg gaagagggca atatttagtg tttgggccta   240
cttgttgttg ggctccccac tgcctctcct ttgcagagct atcactggcc ctggttgca    300 aactctcggt ggctttcaag cctacaaaac aaaaactgag agggtgtcca aaagagaag    360 aagaaaacgt tgttgttggt cctggattcc actgttggat tttggtgggg atgagaagaa   420
ggaattacca ggtgtgatca acacctgcac ggtacctgca cggctttaaa ga atg cgt   478
                                                         Met Arg
                                                          1
```

| | | | | | | | | | | | | | | | | |
|---|---|---|---|---|---|---|---|---|---|---|---|---|---|---|---|---|
| tcc | aga | ggc | agt | gat | acc | gag | ggc | tca | gcc | caa | aag | aaa | ttt | cca | aga | 526 |
| Ser | Arg | Gly | Ser | Asp | Thr | Glu | Gly | Ser | Ala | Gln | Lys | Lys | Phe | Pro | Arg | |
| | 5 | | | | 10 | | | | | 15 | | | | | | |
| cat | act | aaa | ggc | cac | agt | ttc | caa | ggg | cct | aaa | aac | atg | aag | cat | aga | 574 |
| His | Thr | Lys | Gly | His | Ser | Phe | Gln | Gly | Pro | Lys | Asn | Met | Lys | His | Arg | |
| | 20 | | | | 25 | | | | | 30 | | | | | | |
| cag | caa | gac | aaa | gac | tcc | ccc | agt | gag | tcg | gat | gta | ata | ctt | ccg | tgt | 622 |
| Gln | Gln | Asp | Lys | Asp | Ser | Pro | Ser | Glu | Ser | Asp | Val | Ile | Leu | Pro | Cys | |
| 35 | | | | | 40 | | | | | 45 | | | | | 50 | |
| ccc | aag | gca | gag | aag | cca | cac | agt | ggt | aat | ggc | cac | caa | gca | gaa | gac | 670 |
| Pro | Lys | Ala | Glu | Lys | Pro | His | Ser | Gly | Asn | Gly | His | Gln | Ala | Glu | Asp | |
| | | | | 55 | | | | | 60 | | | | | 65 | | |
| ctc | tca | aga | gat | gac | ctg | tta | ttt | ctc | ctc | agc | att | ctg | gag | gga | gaa | 718 |
| Leu | Ser | Arg | Asp | Asp | Leu | Leu | Phe | Leu | Leu | Ser | Ile | Leu | Glu | Gly | Glu | |
| | | | 70 | | | | | 75 | | | | | 80 | | | |
| ctg | cag | gct | cga | gat | gag | gtc | ata | ggc | att | tta | aag | gct | gaa | aaa | atg | 766 |
| Leu | Gln | Ala | Arg | Asp | Glu | Val | Ile | Gly | Ile | Leu | Lys | Ala | Glu | Lys | Met | |
| | | | 85 | | | | | 90 | | | | | 95 | | | |
| gac | ctg | gct | ttg | ctg | gaa | gct | cag | tat | ggg | ttt | gtc | act | cca | aaa | aag | 814 |
| Asp | Leu | Ala | Leu | Leu | Glu | Ala | Gln | Tyr | Gly | Phe | Val | Thr | Pro | Lys | Lys | |
| | | 100 | | | | | 105 | | | | | 110 | | | | |
| gtg | tta | gag | gct | ctc | cag | aga | gat | gct | ttt | caa | gcg | aaa | tct | acc | cct | 862 |
| Val | Leu | Glu | Ala | Leu | Gln | Arg | Asp | Ala | Phe | Gln | Ala | Lys | Ser | Thr | Pro | |
| 115 | | | | | 120 | | | | | 125 | | | | | 130 | |
| tgg | cag | gag | gac | atc | tat | gag | aaa | cca | atg | aat | gag | ttg | gac | aaa | gtt | 910 |
| Trp | Gln | Glu | Asp | Ile | Tyr | Glu | Lys | Pro | Met | Asn | Glu | Leu | Asp | Lys | Val | |
| | | | | 135 | | | | | 140 | | | | | 145 | | |
| gtg | gaa | aaa | cat | aaa | gaa | tct | tac | aga | cga | atc | ctg | gga | cag | ctt | tta | 958 |
| Val | Glu | Lys | His | Lys | Glu | Ser | Tyr | Arg | Arg | Ile | Leu | Gly | Gln | Leu | Leu | |
| | | | 150 | | | | | 155 | | | | | 160 | | | |
| gtg | gca | gaa | aaa | tcc | cgt | agg | caa | acc | ata | ttg | gag | ttg | gag | gaa | gaa | 1006 |
| Val | Ala | Glu | Lys | Ser | Arg | Arg | Gln | Thr | Ile | Leu | Glu | Leu | Glu | Glu | Glu | |
| | | | 165 | | | | | 170 | | | | | 175 | | | |
| aag | aga | aaa | cat | aaa | gaa | tac | atg | gag | aag | agt | gat | gaa | ttc | ata | tgc | 1054 |
| Lys | Arg | Lys | His | Lys | Glu | Tyr | Met | Glu | Lys | Ser | Asp | Glu | Phe | Ile | Cys | |
| | | 180 | | | | | 185 | | | | | 190 | | | | |
| cta | cta | gaa | cag | gaa | tgt | gaa | aga | tta | aag | aag | cta | att | gat | caa | gaa | 1102 |
| Leu | Leu | Glu | Gln | Glu | Cys | Glu | Arg | Leu | Lys | Lys | Leu | Ile | Asp | Gln | Glu | |
| 195 | | | | | 200 | | | | | 205 | | | | | 210 | |
| atc | aag | tct | cag | gag | gag | aag | gag | caa | gaa | aag | gag | aaa | agg | gtc | acc | 1150 |
| Ile | Lys | Ser | Gln | Glu | Glu | Lys | Glu | Gln | Glu | Lys | Glu | Lys | Arg | Val | Thr | |
| | | | | 215 | | | | | 220 | | | | | 225 | | |

```
                                                           -continued
acc ctg aaa gag gag ctg acc aag ctg aag tct ttt gct ttg atg gtg    1198
Thr Leu Lys Glu Glu Leu Thr Lys Leu Lys Ser Phe Ala Leu Met Val
        230                 235                 240 gtg gat gaa cag caa agg ctg acg gca cag ctc acc ctt caa aga cag    1246
Val Asp Glu Gln Gln Arg Leu Thr Ala Gln Leu Thr Leu Gln Arg Gln
245                 250                 255 aaa atc caa gag ctg acc aca aat gca aag gaa aca cat acc aaa cta    1294
Lys Ile Gln Glu Leu Thr Thr Asn Ala Lys Glu Thr His Thr Lys Leu
        260                 265                 270 gcc ctt gct gaa gcc aga gtt cag gag gaa gag cag aag gca acc aga    1342
Ala Leu Ala Glu Ala Arg Val Gln Glu Glu Glu Gln Lys Ala Thr Arg
275                 280                 285                 290 cta gag aag gaa ctg caa acg cag acc aca aag ttt cac caa gac caa    1390
Leu Glu Lys Glu Leu Gln Thr Gln Thr Thr Lys Phe His Gln Asp Gln
            295                 300                 305 gac aca att atg gcg aag ctc acc aat gag gac agt caa aat cgc cag    1438
Asp Thr Ile Met Ala Lys Leu Thr Asn Glu Asp Ser Gln Asn Arg Gln
        310                 315                 320 ctt caa caa aag ctg gca gca ctc agc cgg cag att gat gag tta gaa    1486
Leu Gln Gln Lys Leu Ala Ala Leu Ser Arg Gln Ile Asp Glu Leu Glu
325                 330                 335 gag aca aac agg tct tta cga aaa gca gag gag ctg caa gat ata        1534
Glu Thr Asn Arg Ser Leu Arg Lys Ala Glu Glu Leu Gln Asp Ile
            340                 345                 350 aaa gaa aaa atc agt aag gga gaa tat gga aac gct ggt atc atg gct    1582
Lys Glu Lys Ile Ser Lys Gly Glu Tyr Gly Asn Ala Gly Ile Met Ala
355                 360                 365                 370 gaa gtg gaa gag ctc agg aaa cgt gtg cta gat atg gaa ggg aaa gat    1630
Glu Val Glu Glu Leu Arg Lys Arg Val Leu Asp Met Glu Gly Lys Asp
                375                 380                 385 gaa gag ctc ata aaa atg gag gag cag tgc aga gat ctc aat aag agg    1678
Glu Glu Leu Ile Lys Met Glu Glu Gln Cys Arg Asp Leu Asn Lys Arg
        390                 395                 400 ctt gaa agg gag acg tta cag agt aaa gac ttt aaa cta gag gtt gaa    1726
Leu Glu Arg Glu Thr Leu Gln Ser Lys Asp Phe Lys Leu Glu Val Glu
            405                 410                 415 aaa ctc agt aaa aga att atg gct ctg gaa aag tta gaa gac gct ttc    1774
Lys Leu Ser Lys Arg Ile Met Ala Leu Glu Lys Leu Glu Asp Ala Phe
420                 425                 430 aac aaa agc aaa caa gaa tgc tac tct ctg aaa tgc aat tta gaa aaa    1822
Asn Lys Ser Lys Gln Glu Cys Tyr Ser Leu Lys Cys Asn Leu Glu Lys
435                 440                 445                 450 gaa agg atg acc aca aag cag ttg tct caa gaa ctg gag agt tta aaa    1870
Glu Arg Met Thr Thr Lys Gln Leu Ser Gln Glu Leu Glu Ser Leu Lys
                455                 460                 465 gta agg atc aaa gag cta gaa gcc att gaa agt cgg cta gaa aag aca    1918
Val Arg Ile Lys Glu Leu Glu Ala Ile Glu Ser Arg Leu Glu Lys Thr
        470                 475                 480 gaa ttc act cta aaa gag gat tta act aaa ctg aaa aca tta act gtg    1966
Glu Phe Thr Leu Lys Glu Asp Leu Thr Lys Leu Lys Thr Leu Thr Val
            485                 490                 495 atg ttt gta gat gaa cgg aaa aca atg agt gaa aaa tta aag aaa act    2014
Met Phe Val Asp Glu Arg Lys Thr Met Ser Glu Lys Leu Lys Lys Thr
500                 505                 510 gaa gat aaa tta caa gct gct tct tct cag ctt caa gtg gag caa aat    2062
Glu Asp Lys Leu Gln Ala Ala Ser Ser Gln Leu Gln Val Glu Gln Asn
515                 520                 525                 530 aaa gta aca aca gtt act gag aag tta att gag gaa act aaa agg gcg    2110
Lys Val Thr Thr Val Thr Glu Lys Leu Ile Glu Glu Thr Lys Arg Ala
                535                 540                 545
```

| | |
|---|---|
| ctc aag tcc aaa acc gat gta gaa gaa aag atg tac agc gta acc aag<br>Leu Lys Ser Lys Thr Asp Val Glu Glu Lys Met Tyr Ser Val Thr Lys<br>550                555                 560 | 2158 |
| gag aga gat gat tta aaa aac aaa ttg aaa gcg gaa gaa gag aaa gga<br>Glu Arg Asp Asp Leu Lys Asn Lys Leu Lys Ala Glu Glu Glu Lys Gly<br>    565                 570                 575 | 2206 |
| aat gat ctc ctg tca aga gtt aat atg ttg aaa aat agg ctt caa tca<br>Asn Asp Leu Leu Ser Arg Val Asn Met Leu Lys Asn Arg Leu Gln Ser<br>580                 585                 590 | 2254 |
| ttg gaa gca att gag aaa gat ttc cta aaa aac aaa tta aat caa gac<br>Leu Glu Ala Ile Glu Lys Asp Phe Leu Lys Asn Lys Leu Asn Gln Asp<br>595                 600                 605                 610 | 2302 |
| tct ggg aaa tcc aca aca gca tta cac caa gaa aac aat aag att aag<br>Ser Gly Lys Ser Thr Thr Ala Leu His Gln Glu Asn Asn Lys Ile Lys<br>    615                 620                 625 | 2350 |
| gag ctc tct caa gaa gtg gaa aga ctg aaa ctg aag cta aag gac atg<br>Glu Leu Ser Gln Glu Val Glu Arg Leu Lys Leu Lys Leu Lys Asp Met<br>630                 635                 640 | 2398 |
| aaa gcc att gag gat gac ctc atg aaa aca gaa gat gaa tat gag act<br>Lys Ala Ile Glu Asp Asp Leu Met Lys Thr Glu Asp Glu Tyr Glu Thr<br>645                 650                 655 | 2446 |
| cta gaa cga agg tat gct aat gaa cga gac aaa gct caa ttt tta tct<br>Leu Glu Arg Arg Tyr Ala Asn Glu Arg Asp Lys Ala Gln Phe Leu Ser<br>660                 665                 670 | 2494 |
| aaa gag cta gaa cat gtt aaa atg gaa ctt gct aag tac aag tta gca<br>Lys Glu Leu Glu His Val Lys Met Glu Leu Ala Lys Tyr Lys Leu Ala<br>675                 680                 685                 690 | 2542 |
| gaa aag aca gag acc agc cat gaa caa tgg ctt ttc aaa agg ctt caa<br>Glu Lys Thr Glu Thr Ser His Glu Gln Trp Leu Phe Lys Arg Leu Gln<br>    695                 700                 705 | 2590 |
| gaa gaa gaa gct aag tca ggg cac ctc tca aga gaa gtg gat gca tta<br>Glu Glu Glu Ala Lys Ser Gly His Leu Ser Arg Glu Val Asp Ala Leu<br>    710                 715                 720 | 2638 |
| aaa gag aaa att cat gaa tac atg gca act gaa gac cta ata tgt cac<br>Lys Glu Lys Ile His Glu Tyr Met Ala Thr Glu Asp Leu Ile Cys His<br>725                 730                 735 | 2686 |
| ctc cag gga gat cac tca gtc ctg caa aaa aaa act aaa tca aca aga<br>Leu Gln Gly Asp His Ser Val Leu Gln Lys Lys Thr Lys Ser Thr Arg<br>740                 745                 750 | 2734 |
| aaa cag gaa cag aga ttt agg aag aga gat tga aaacctcact aaggagttag<br>Lys Gln Glu Gln Arg Phe Arg Lys Arg Asp<br>755                 760 | 2787 |
| agaggtaccg gcatttcagt aagagcctca ggcctagtct caatggaaga agaatttccg | 2847 |
| atcctcaagt attttctaaa gaagttcaga cagaagcagt agacaatgaa ccacctgatt | 2907 |
| acaagagcct cattcctctg gaacgtgcag tcatcaatgg tcagttatat gaggagagtg | 2967 |
| agaatcaaga cgaggaccct aatgatgagg gatctgtgct gtccttcaaa tgcagccagt | 3027 |
| ctactccatg tcctgttaac agaaagctat ggattccctg gatgaaatcc aaggagggcc | 3087 |
| atcttcagaa tggaaaaatg caaactaaac ccaatgccaa cttttgtgcaa cctggagatc | 3147 |
| tagtcctaag ccacacacct gggcagccac ttcatataaa ggttactcca gaccatgtac | 3207 |
| aaaacacagc cactcttgaa atcacaagtc caaccacaga gagtcctcac tcttacacga | 3267 |
| gtactgcagt gataccgaac tgtggcacgc caaagcaaag gataaccatc ctccaaaacg | 3327 |
| cctccataac accagtaaag tccaaaaacct ctaccgaaga cctcatgaat ttagaacaag | 3387 |
| gcatgtcccc aattaccatg gcaacctttg ccagagcaca gaccccagag tcttgtggtt | 3447 |

-continued

```
ctctaactcc agaaggaca atgtcccta ttcaggtttt ggctgtgact ggttcagcta      3507
gctctcctga gcagggacgc tccccagaac caacagaaat cagtgccaag catgcgatat    3567
tcagagtctc cccagaccgg cagtcatcat ggcagtttca gcgttcaaac agcaatagct    3627
caagtgtgat aactactgag gataataaaa tccacattca cttaggaagt ccttacatgc    3687
aagctgtagc cagccctgtg agacctgcca gcccttcagc accactgcag gataaccgaa    3747
ctcaaggctt aattaacggg gcactaaaca aaacaaccaa taaagtcacc agcagtatta    3807
ctatcacacc aacagccaca cctcttcctc gacaatcaca aattacagtg gaaccacttc    3867
ttctgcctca ttgaactcaa catccttcag acttttaagg cattccaaat cccagtcttc    3927
atgttgaact gggttaagca tttattaaaa aatcgttttc ttctacaaaa aaaaaaaaa    3987
aaaaaaaaa a                                                          3998
```

<210> SEQ ID NO 10
<211> LENGTH: 764
<212> TYPE: PRT
<213> ORGANISM: Homo sapiens

<400> SEQUENCE: 10

```
Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Leu Leu Phe Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

Thr Pro Trp Gln Glu Asp Ile Tyr Glu Lys Pro Met Asn Glu Leu Asp
    130                 135                 140

Lys Val Glu Lys His Lys Glu Ser Tyr Arg Arg Ile Leu Gly Gln
145                 150                 155                 160

Leu Leu Val Ala Glu Lys Ser Arg Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205

Gln Glu Ile Lys Ser Gln Glu Glu Lys Glu Gln Glu Lys Glu Lys Arg
    210                 215                 220

Val Thr Thr Leu Lys Glu Glu Leu Thr Lys Leu Lys Ser Phe Ala Leu
225                 230                 235                 240

Met Val Val Asp Glu Gln Arg Leu Thr Ala Gln Leu Thr Leu Gln
                245                 250                 255

Arg Gln Lys Ile Gln Glu Leu Thr Thr Asn Ala Lys Glu Thr His Thr
            260                 265                 270
```

-continued

```
Lys Leu Ala Leu Ala Glu Ala Arg Val Gln Glu Glu Gln Lys Ala
            275                 280                 285
Thr Arg Leu Glu Lys Glu Leu Gln Thr Gln Thr Thr Lys Phe His Gln
        290                 295                 300
Asp Gln Asp Thr Ile Met Ala Lys Leu Thr Asn Glu Asp Ser Gln Asn
305                 310                 315                 320
Arg Gln Leu Gln Gln Lys Leu Ala Ala Leu Ser Arg Gln Ile Asp Glu
                325                 330                 335
Leu Glu Glu Thr Asn Arg Ser Leu Arg Lys Ala Glu Glu Leu Gln
            340                 345                 350
Asp Ile Lys Glu Lys Ile Ser Lys Gly Glu Tyr Gly Asn Ala Gly Ile
            355                 360                 365
Met Ala Glu Val Glu Glu Leu Arg Lys Arg Val Leu Asp Met Glu Gly
        370                 375                 380
Lys Asp Glu Glu Leu Ile Lys Met Glu Glu Gln Cys Arg Asp Leu Asn
385                 390                 395                 400
Lys Arg Leu Glu Arg Glu Thr Leu Gln Ser Lys Asp Phe Lys Leu Glu
                405                 410                 415
Val Glu Lys Leu Ser Lys Arg Ile Met Ala Leu Glu Lys Leu Glu Asp
            420                 425                 430
Ala Phe Asn Lys Ser Lys Gln Glu Cys Tyr Ser Leu Lys Cys Asn Leu
        435                 440                 445
Glu Lys Glu Arg Met Thr Thr Lys Gln Leu Ser Gln Glu Leu Glu Ser
    450                 455                 460
Leu Lys Val Arg Ile Lys Glu Leu Glu Ala Ile Glu Ser Arg Leu Glu
465                 470                 475                 480
Lys Thr Glu Phe Thr Leu Lys Glu Asp Leu Thr Lys Leu Lys Thr Leu
                485                 490                 495
Thr Val Met Phe Val Asp Glu Arg Lys Thr Met Ser Glu Lys Leu Lys
            500                 505                 510
Lys Thr Glu Asp Lys Leu Gln Ala Ala Ser Ser Gln Leu Gln Val Glu
        515                 520                 525
Gln Asn Lys Val Thr Thr Val Thr Glu Lys Leu Ile Glu Glu Thr Lys
    530                 535                 540
Arg Ala Leu Lys Ser Lys Thr Asp Val Glu Glu Lys Met Tyr Ser Val
545                 550                 555                 560
Thr Lys Glu Arg Asp Asp Leu Lys Asn Lys Leu Lys Ala Glu Glu Glu
                565                 570                 575
Lys Gly Asn Asp Leu Leu Ser Arg Val Asn Met Leu Lys Asn Arg Leu
            580                 585                 590
Gln Ser Leu Glu Ala Ile Glu Lys Asp Phe Leu Lys Asn Lys Leu Asn
        595                 600                 605
Gln Asp Ser Gly Lys Ser Thr Thr Ala Leu His Gln Glu Asn Asn Lys
    610                 615                 620
Ile Lys Glu Leu Ser Gln Glu Val Glu Arg Leu Lys Leu Lys Leu Lys
625                 630                 635                 640
Asp Met Lys Ala Ile Glu Asp Leu Met Lys Thr Glu Asp Glu Tyr
                645                 650                 655
Glu Thr Leu Glu Arg Arg Tyr Ala Asn Glu Arg Asp Lys Ala Gln Phe
            660                 665                 670
Leu Ser Lys Glu Leu Glu His Val Lys Met Glu Leu Ala Lys Tyr Lys
        675                 680                 685
Leu Ala Glu Lys Thr Glu Thr Ser His Glu Gln Trp Leu Phe Lys Arg
```

-continued

```
                690                 695                 700
Leu Gln Glu Glu Glu Ala Lys Ser Gly His Leu Ser Arg Glu Val Asp
705                 710                 715                 720

Ala Leu Lys Glu Lys Ile His Glu Tyr Met Ala Thr Glu Asp Leu Ile
                725                 730                 735

Cys His Leu Gln Gly Asp His Ser Val Leu Gln Lys Lys Thr Lys Ser
                740                 745                 750

Thr Arg Lys Gln Glu Gln Arg Phe Arg Lys Arg Asp
            755                 760

<210> SEQ ID NO 11
<211> LENGTH: 3430
<212> TYPE: DNA
<213> ORGANISM: Homo sapiens
<220> FEATURE:
<221> NAME/KEY: misc_feature
<223> OTHER INFORMATION: GIP130a
<220> FEATURE:
<221> NAME/KEY: CDS
<222> LOCATION: (9)..(3413)
<223> OTHER INFORMATION:

<400> SEQUENCE: 11 tttaaaga atg cgt tcc aga ggc agt gat acc gag ggc tca gcc caa aag        50
        Met Arg Ser Arg Gly Ser Asp Thr Glu Gly Ser Ala Gln Lys
        1               5                   10 aaa ttt cca aga cat act aaa ggc cac agt ttc caa ggg cct aaa aac        98
Lys Phe Pro Arg His Thr Lys Gly His Ser Phe Gln Gly Pro Lys Asn
15              20                  25                  30 atg aag cat aga cag caa gac aaa gac tcc ccc agt gag tcg gat gta       146
Met Lys His Arg Gln Gln Asp Lys Asp Ser Pro Ser Glu Ser Asp Val
                35                  40                  45 ata ctt ccg tgt ccc aag gca gag aag cca cac agt ggt aat ggc cac       194
Ile Leu Pro Cys Pro Lys Ala Glu Lys Pro His Ser Gly Asn Gly His
            50                  55                  60 caa gca gaa gac ctc tca aga gat gac ctg tta ttt ctc ctc agc att       242
Gln Ala Glu Asp Leu Ser Arg Asp Asp Leu Leu Phe Leu Leu Ser Ile
        65                  70                  75 ctg gag gga gaa ctg cag gct cga gat gag gtc ata ggc att tta aag       290
Leu Glu Gly Glu Leu Gln Ala Arg Asp Glu Val Ile Gly Ile Leu Lys
80                  85                  90 gct gaa aaa atg gac ctg gct ttg ctg gaa gct cag tat ggg ttt gtc       338
Ala Glu Lys Met Asp Leu Ala Leu Leu Glu Ala Gln Tyr Gly Phe Val
95                  100                 105                 110 act cca aaa aag gtg tta gag gct ctc cag aga gat gct ttt caa gcg       386
Thr Pro Lys Lys Val Leu Glu Ala Leu Gln Arg Asp Ala Phe Gln Ala
                115                 120                 125 aaa tct acc cct tgg cag gag gac atc tat gag aaa cca atg aat gag       434
Lys Ser Thr Pro Trp Gln Glu Asp Ile Tyr Glu Lys Pro Met Asn Glu
            130                 135                 140 ttg gac aaa gtt gtg gaa aaa cat aaa gaa tct tac aga cga atc ctg       482
Leu Asp Lys Val Val Glu Lys His Lys Glu Ser Tyr Arg Arg Ile Leu
        145                 150                 155 gga cag ctt tta gtg gca gaa aaa tcc cgt agg caa acc ata ttg gag       530
Gly Gln Leu Leu Val Ala Glu Lys Ser Arg Arg Gln Thr Ile Leu Glu
    160                 165                 170 ttg gag gaa gaa aag aga aaa cat aaa gaa tac atg gag aag agt gat       578
Leu Glu Glu Glu Lys Arg Lys His Lys Glu Tyr Met Glu Lys Ser Asp
175                 180                 185                 190 gaa ttc ata tgc cta cta gaa cag gaa tgt gaa aga tta aag aag cta       626
Glu Phe Ile Cys Leu Leu Glu Gln Glu Cys Glu Arg Leu Lys Lys Leu
```

-continued

```
              195                 200                 205
att gat caa gaa atc aag tct cag gag gag aag gag caa gaa aag gag    674
Ile Asp Gln Glu Ile Lys Ser Gln Glu Glu Lys Glu Gln Glu Lys Glu
            210                 215                 220 aaa agg gtc acc acc ctg aaa gag gag ctg acc aag ctg aag tct ttt    722
Lys Arg Val Thr Thr Leu Lys Glu Glu Leu Thr Lys Leu Lys Ser Phe
                225                 230                 235 gct ttg atg gtg gtg gat gaa cag caa agg ctg acg gca cag ctc acc    770
Ala Leu Met Val Val Asp Glu Gln Gln Arg Leu Thr Ala Gln Leu Thr
    240                 245                 250 ctt caa aga cag aaa atc caa gag ctg acc aca aat gca aag gaa aca    818
Leu Gln Arg Gln Lys Ile Gln Glu Leu Thr Thr Asn Ala Lys Glu Thr
255                 260                 265                 270 cat acc aaa cta gcc ctt gct gaa gcc aga gtt cag gag gaa gag cag    866
His Thr Lys Leu Ala Leu Ala Glu Ala Arg Val Gln Glu Glu Glu Gln
                275                 280                 285 aag gca acc aga cta gag aag gaa ctg caa acg cag acc aca aag ttt    914
Lys Ala Thr Arg Leu Glu Lys Glu Leu Gln Thr Gln Thr Thr Lys Phe
            290                 295                 300 cac caa gac caa gac aca att atg gcg aag ctc acc aat gag gac agt    962
His Gln Asp Gln Asp Thr Ile Met Ala Lys Leu Thr Asn Glu Asp Ser
        305                 310                 315 caa aat cgc cag ctt caa caa aag ctg gca gca ctc agc cgg cag att   1010
Gln Asn Arg Gln Leu Gln Gln Lys Leu Ala Ala Leu Ser Arg Gln Ile
    320                 325                 330 gat gag tta gaa gag aca aac agg tct tta cga aaa gca gaa gag gag   1058
Asp Glu Leu Glu Glu Thr Asn Arg Ser Leu Arg Lys Ala Glu Glu Glu
335                 340                 345                 350 ctg caa gat ata aaa gaa aaa atc agt aag gga gaa tat gga aac gct   1106
Leu Gln Asp Ile Lys Glu Lys Ile Ser Lys Gly Glu Tyr Gly Asn Ala
                355                 360                 365 ggt atc atg gct gaa gtg gaa gag ctc agg aaa cgt gtg cta gat atg   1154
Gly Ile Met Ala Glu Val Glu Glu Leu Arg Lys Arg Val Leu Asp Met
            370                 375                 380 gaa ggg aaa gat gaa gag ctc ata aaa atg gag gag cag tgc aga gat   1202
Glu Gly Lys Asp Glu Glu Leu Ile Lys Met Glu Glu Gln Cys Arg Asp
        385                 390                 395 ctc aat aag agg ctt gaa agg gag acg tta cag agt aaa gac ttt aaa   1250
Leu Asn Lys Arg Leu Glu Arg Glu Thr Leu Gln Ser Lys Asp Phe Lys
    400                 405                 410 cta gag gtt gaa aaa ctc agt aaa aga att atg gct ctg gaa aag tta   1298
Leu Glu Val Glu Lys Leu Ser Lys Arg Ile Met Ala Leu Glu Lys Leu
415                 420                 425                 430 gaa gac gct ttc aac aaa agc aaa caa gaa tgc tac tct ctg aaa tgc   1346
Glu Asp Ala Phe Asn Lys Ser Lys Gln Glu Cys Tyr Ser Leu Lys Cys
                435                 440                 445 aat tta gaa aaa gaa agg atg acc aca aag cag ttg tct caa gaa ctg   1394
Asn Leu Glu Lys Glu Arg Met Thr Thr Lys Gln Leu Ser Gln Glu Leu
            450                 455                 460 gag agt tta aaa gta agg atc aaa gag cta gaa gcc att gaa agt cgg   1442
Glu Ser Leu Lys Val Arg Ile Lys Glu Leu Glu Ala Ile Glu Ser Arg
        465                 470                 475 cta gaa aag aca gaa ttc act cta aaa gag gat tta act aaa ctg aaa   1490
Leu Glu Lys Thr Glu Phe Thr Leu Lys Glu Asp Leu Thr Lys Leu Lys
    480                 485                 490 aca tta act gtg atg ttt gta gat gaa cgg aaa aca atg agt gaa aaa   1538
Thr Leu Thr Val Met Phe Val Asp Glu Arg Lys Thr Met Ser Glu Lys
495                 500                 505                 510 tta aag aaa act gaa gat aaa tta caa gct gct tct tct cag ctt caa   1586
```

-continued

| | | | | | | | | | | | | |
|---|---|---|---|---|---|---|---|---|---|---|---|---|
| Leu | Lys | Lys | Thr | Glu | Asp | Lys | Leu | Gln | Ala | Ala | Ser | Ser | Gln | Leu | Gln |
| | | | | 515 | | | | 520 | | | | | 525 | | | gtg gag caa aat aaa gta aca aca gtt act gag aag tta att gag gaa    1634
Val Glu Gln Asn Lys Val Thr Thr Val Thr Glu Lys Leu Ile Glu Glu
            530                 535                 540 act aaa agg gcg ctc aag tcc aaa acc gat gta gaa gaa aag atg tac    1682
Thr Lys Arg Ala Leu Lys Ser Lys Thr Asp Val Glu Glu Lys Met Tyr
            545                 550                 555 agc gta acc aag gag aga gat gat tta aaa aac aaa ttg aaa gcg gaa    1730
Ser Val Thr Lys Glu Arg Asp Asp Leu Lys Asn Lys Leu Lys Ala Glu
            560                 565                 570 gaa gag aaa gga aat gat ctc ctg tca aga gtt aat atg ttg aaa aat    1778
Glu Glu Lys Gly Asn Asp Leu Leu Ser Arg Val Asn Met Leu Lys Asn
575                 580                 585                 590 agg ctt caa tca ttg gaa gca att gag aaa gat ttc cta aaa aac aaa    1826
Arg Leu Gln Ser Leu Glu Ala Ile Glu Lys Asp Phe Leu Lys Asn Lys
                595                 600                 605 tta aat caa gac tct ggg aaa tcc aca aca gca tta cac caa gaa aac    1874
Leu Asn Gln Asp Ser Gly Lys Ser Thr Thr Ala Leu His Gln Glu Asn
            610                 615                 620 aat aag att aag gag ctc tct caa gaa gtg gaa aga ctg aaa ctg aag    1922
Asn Lys Ile Lys Glu Leu Ser Gln Glu Val Glu Arg Leu Lys Leu Lys
            625                 630                 635 cta aag gac atg aaa gcc att gag gat gac ctc atg aaa aca gaa gat    1970
Leu Lys Asp Met Lys Ala Ile Glu Asp Asp Leu Met Lys Thr Glu Asp
            640                 645                 650 gaa tat gag act cta gaa cga agg tat gct aat gaa cga gac aaa gct    2018
Glu Tyr Glu Thr Leu Glu Arg Arg Tyr Ala Asn Glu Arg Asp Lys Ala
655                 660                 665                 670 caa ttt tta tct aaa gag cta gaa cat gtt aaa atg gaa ctt gct aag    2066
Gln Phe Leu Ser Lys Glu Leu Glu His Val Lys Met Glu Leu Ala Lys
                675                 680                 685 tac aag tta gca gaa aag aca gag acc agc cat gaa caa tgg ctt ttc    2114
Tyr Lys Leu Ala Glu Lys Thr Glu Thr Ser His Glu Gln Trp Leu Phe
            690                 695                 700 aaa agg ctt caa gaa gaa gaa gct aag tca ggg cac ctc tca aga gaa    2162
Lys Arg Leu Gln Glu Glu Glu Ala Lys Ser Gly His Leu Ser Arg Glu
            705                 710                 715 gtg gat gca tta aaa gag aaa att cat gaa tac atg gca act gaa gac    2210
Val Asp Ala Leu Lys Glu Lys Ile His Glu Tyr Met Ala Thr Glu Asp
720                 725                 730 cta ata tgt cac ctc cag gga gat cac tca gtc ctg caa aaa aaa cta    2258
Leu Ile Cys His Leu Gln Gly Asp His Ser Val Leu Gln Lys Lys Leu
735                 740                 745                 750 aat caa caa gaa aac agg aac aga gat tta gga aga gag att gaa aac    2306
Asn Gln Gln Glu Asn Arg Asn Arg Asp Leu Gly Arg Glu Ile Glu Asn
                755                 760                 765 ctc act aag gag tta gag agg tac cgg cat ttc agt aag agc ctc agg    2354
Leu Thr Lys Glu Leu Glu Arg Tyr Arg His Phe Ser Lys Ser Leu Arg
            770                 775                 780 cct agt ctc aat gga aga aga att tcc gat cct caa gta ttt tct aaa    2402
Pro Ser Leu Asn Gly Arg Arg Ile Ser Asp Pro Gln Val Phe Ser Lys
            785                 790                 795 gaa gtt cag aca gaa gca gta gac aat gaa cca cct gat tac aag agc    2450
Glu Val Gln Thr Glu Ala Val Asp Asn Glu Pro Pro Asp Tyr Lys Ser
800                 805                 810 ctc att cct ctg gaa cgt gca gtc atc aat ggt cag tta tat gag gag    2498
Leu Ile Pro Leu Glu Arg Ala Val Ile Asn Gly Gln Leu Tyr Glu Glu
815                 820                 825                 830

-continued

```
agt gag aat caa gac gag gac cct aat gat gag gga tct gtg ctg tcc    2546
Ser Glu Asn Gln Asp Glu Asp Pro Asn Asp Glu Gly Ser Val Leu Ser
                835                 840                 845 ttc aaa tgc agc cag tct act cca tgt cct gtt aac aga aag cta tgg    2594
Phe Lys Cys Ser Gln Ser Thr Pro Cys Pro Val Asn Arg Lys Leu Trp
        850                 855                 860 att ccc tgg atg aaa tcc aag gag ggc cat ctt cag aat gga aaa atg    2642
Ile Pro Trp Met Lys Ser Lys Glu Gly His Leu Gln Asn Gly Lys Met
865                 870                 875 caa act aaa ccc aat gcc aac ttt gtg caa cct gga gat cta gtc cta    2690
Gln Thr Lys Pro Asn Ala Asn Phe Val Gln Pro Gly Asp Leu Val Leu
        880                 885                 890 agc cac aca cct ggg cag cca ctt cat ata aag gtt act cca gac cat    2738
Ser His Thr Pro Gly Gln Pro Leu His Ile Lys Val Thr Pro Asp His
895                 900                 905                 910 gta caa aac aca gcc act ctt gaa atc aca agt cca acc aca gag agt    2786
Val Gln Asn Thr Ala Thr Leu Glu Ile Thr Ser Pro Thr Thr Glu Ser
                915                 920                 925 cct cac tct tac acg agt act gca gtg ata ccg aac tgt ggc acg cca    2834
Pro His Ser Tyr Thr Ser Thr Ala Val Ile Pro Asn Cys Gly Thr Pro
        930                 935                 940 aag caa agg ata acc atc ctc caa aac gcc tcc ata aca cca gta aag    2882
Lys Gln Arg Ile Thr Ile Leu Gln Asn Ala Ser Ile Thr Pro Val Lys
945                 950                 955 tcc aaa acc tct acc gaa gac ctc atg aat tta gaa caa ggc atg tcc    2930
Ser Lys Thr Ser Thr Glu Asp Leu Met Asn Leu Glu Gln Gly Met Ser
        960                 965                 970 cca att acc atg gca acc ttt gcc aga gca cag acc cca gag tct tgt    2978
Pro Ile Thr Met Ala Thr Phe Ala Arg Ala Gln Thr Pro Glu Ser Cys
975                 980                 985                 990 ggt tct cta act cca gaa agg aca atg tcc cct att cag gtt ttg  gct   3026
Gly Ser Leu Thr Pro Glu Arg Thr Met Ser Pro Ile Gln Val Leu  Ala
                995                 1000                1005 gtg act ggt tca  gct agc tct cct gag  cag gga cgc tcc cca  gaa     3071
Val Thr Gly Ser Ala Ser Ser Pro Glu  Gln Gly Arg Ser Pro  Glu
                1010                 1015                 1020 cca aca gaa atc  agt gcc aag cat gcg  ata ttc aga gtc tcc  cca     3116
Pro Thr Glu Ile Ser Ala Lys His Ala  Ile Phe Arg Val Ser  Pro
                1025                 1030                 1035 gac cgg cag tca  tca tgg cag ttt cag  cgt tca aac agc aat  agc     3161
Asp Arg Gln Ser Ser Trp Gln Phe Gln  Arg Ser Asn Ser Asn  Ser
                1040                 1045                 1050 tca agt gtg ata  act act gag gat aat  aaa atc cac att cac  tta     3206
Ser Ser Val Ile Thr Thr Glu Asp Asn  Lys Ile His Ile His  Leu
                1055                 1060                 1065 gga agt cct tac  atg caa gct gta gcc  agc cct gtg aga cct  gcc     3251
Gly Ser Pro Tyr Met Gln Ala Val Ala  Ser Pro Val Arg Pro  Ala
                1070                 1075                 1080 agc cct tca gca  cca ctg cag gat aac  cga act caa ggc tta  att     3296
Ser Pro Ser Ala Pro Leu Gln Asp Asn  Arg Thr Gln Gly Leu  Ile
                1085                 1090                 1095 aac ggg gca cta  aac aaa aca acc aat  aaa gtc acc agc agt  att     3341
Asn Gly Ala Leu Asn Lys Thr Thr Asn  Lys Val Thr Ser Ser  Ile
                1100                 1105                 1110 act atc aca cca  aca gcc aca cct ctt  cct cga caa tca caa  att     3386
Thr Ile Thr Pro Thr Ala Thr Pro Leu  Pro Arg Gln Ser Gln  Ile
                1115                 1120                 1125 aca gtg gaa cca ctt ctt ctg cct cat tgaactcaac atccttc              3430
Thr Val Glu Pro Leu Leu Leu Pro His
                1130                 1135
```

<210> SEQ ID NO 12
<211> LENGTH: 1135
<212> TYPE: PRT
<213> ORGANISM: Homo sapiens

<400> SEQUENCE: 12

```
Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Asp Leu Leu Phe Leu Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

Thr Pro Trp Gln Glu Asp Ile Tyr Glu Lys Pro Met Asn Glu Leu Asp
    130                 135                 140

Lys Val Val Glu Lys His Lys Glu Ser Tyr Arg Arg Ile Leu Gly Gln
145                 150                 155                 160

Leu Leu Val Ala Glu Lys Ser Arg Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205

Gln Glu Ile Lys Ser Gln Glu Lys Glu Gln Glu Lys Glu Lys Arg
    210                 215                 220

Val Thr Thr Leu Lys Glu Glu Leu Thr Lys Leu Lys Ser Phe Ala Leu
225                 230                 235                 240

Met Val Val Asp Glu Gln Gln Arg Leu Thr Ala Gln Leu Thr Leu Gln
                245                 250                 255

Arg Gln Lys Ile Gln Glu Leu Thr Thr Asn Ala Lys Glu Thr His Thr
            260                 265                 270

Lys Leu Ala Leu Ala Glu Ala Arg Val Gln Glu Glu Gln Lys Ala
        275                 280                 285

Thr Arg Leu Glu Lys Glu Leu Gln Thr Gln Thr Thr Lys Phe His Gln
    290                 295                 300

Asp Gln Asp Thr Ile Met Ala Lys Leu Thr Asn Glu Asp Ser Gln Asn
305                 310                 315                 320

Arg Gln Leu Gln Gln Lys Leu Ala Ala Leu Ser Arg Gln Ile Asp Glu
                325                 330                 335

Leu Glu Glu Thr Asn Arg Ser Leu Arg Lys Ala Glu Glu Leu Gln
            340                 345                 350

Asp Ile Lys Glu Lys Ile Ser Lys Gly Glu Tyr Gly Asn Ala Gly Ile
        355                 360                 365

Met Ala Glu Val Glu Glu Leu Arg Lys Arg Val Leu Asp Met Glu Gly
```

-continued

```
                370                 375                 380
Lys Asp Glu Glu Leu Ile Lys Met Glu Glu Gln Cys Arg Asp Leu Asn
385                 390                 395                 400

Lys Arg Leu Glu Arg Glu Thr Leu Gln Ser Lys Asp Phe Lys Leu Glu
                405                 410                 415

Val Glu Lys Leu Ser Lys Arg Ile Met Ala Leu Glu Lys Leu Glu Asp
            420                 425                 430

Ala Phe Asn Lys Ser Lys Gln Glu Cys Tyr Ser Leu Lys Cys Asn Leu
        435                 440                 445

Glu Lys Glu Arg Met Thr Thr Lys Gln Leu Ser Gln Glu Leu Glu Ser
    450                 455                 460

Leu Lys Val Arg Ile Lys Glu Leu Glu Ala Ile Glu Ser Arg Leu Glu
465                 470                 475                 480

Lys Thr Glu Phe Thr Leu Lys Glu Asp Leu Thr Lys Leu Lys Thr Leu
                485                 490                 495

Thr Val Met Phe Val Asp Glu Arg Lys Thr Met Ser Glu Lys Leu Lys
            500                 505                 510

Lys Thr Glu Asp Lys Leu Gln Ala Ala Ser Ser Gln Leu Gln Val Glu
        515                 520                 525

Gln Asn Lys Val Thr Thr Val Thr Glu Lys Leu Ile Glu Glu Thr Lys
    530                 535                 540

Arg Ala Leu Lys Ser Lys Thr Asp Val Glu Glu Lys Met Tyr Ser Val
545                 550                 555                 560

Thr Lys Glu Arg Asp Asp Leu Lys Asn Lys Leu Lys Ala Glu Glu Glu
                565                 570                 575

Lys Gly Asn Asp Leu Leu Ser Arg Val Asn Met Leu Lys Asn Arg Leu
            580                 585                 590

Gln Ser Leu Glu Ala Ile Glu Lys Asp Phe Leu Lys Asn Lys Leu Asn
        595                 600                 605

Gln Asp Ser Gly Lys Ser Thr Thr Ala Leu His Gln Glu Asn Asn Lys
    610                 615                 620

Ile Lys Glu Leu Ser Gln Glu Val Glu Arg Leu Lys Leu Lys Leu Lys
625                 630                 635                 640

Asp Met Lys Ala Ile Glu Asp Asp Leu Met Lys Thr Glu Asp Glu Tyr
                645                 650                 655

Glu Thr Leu Glu Arg Arg Tyr Ala Asn Glu Arg Asp Lys Ala Gln Phe
            660                 665                 670

Leu Ser Lys Glu Leu Glu His Val Lys Met Glu Leu Ala Lys Tyr Lys
        675                 680                 685

Leu Ala Glu Lys Thr Glu Thr Ser His Glu Gln Trp Leu Phe Lys Arg
    690                 695                 700

Leu Gln Glu Glu Glu Ala Lys Ser Gly His Leu Ser Arg Glu Val Asp
705                 710                 715                 720

Ala Leu Lys Glu Lys Ile His Glu Tyr Met Ala Thr Glu Asp Leu Ile
                725                 730                 735

Cys His Leu Gln Gly Asp His Ser Val Leu Gln Lys Lys Leu Asn Gln
            740                 745                 750

Gln Glu Asn Arg Asn Arg Asp Leu Gly Arg Glu Ile Glu Asn Leu Thr
        755                 760                 765

Lys Glu Leu Glu Arg Tyr Arg His Phe Ser Lys Ser Leu Arg Pro Ser
    770                 775                 780

Leu Asn Gly Arg Arg Ile Ser Asp Pro Gln Val Phe Ser Lys Glu Val
785                 790                 795                 800
```

```
Gln Thr Glu Ala Val Asp Asn Glu Pro Pro Asp Tyr Lys Ser Leu Ile
            805                 810                 815

Pro Leu Glu Arg Ala Val Ile Asn Gly Gln Leu Tyr Glu Glu Ser Glu
        820                 825                 830

Asn Gln Asp Glu Asp Pro Asn Asp Glu Gly Ser Val Leu Ser Phe Lys
        835                 840                 845

Cys Ser Gln Ser Thr Pro Cys Pro Val Asn Arg Lys Leu Trp Ile Pro
    850                 855                 860

Trp Met Lys Ser Lys Glu Gly His Leu Gln Asn Gly Lys Met Gln Thr
865                 870                 875                 880

Lys Pro Asn Ala Asn Phe Val Gln Pro Gly Asp Leu Val Leu Ser His
                885                 890                 895

Thr Pro Gly Gln Pro Leu His Ile Lys Val Thr Pro Asp His Val Gln
            900                 905                 910

Asn Thr Ala Thr Leu Glu Ile Thr Ser Pro Thr Thr Glu Ser Pro His
        915                 920                 925

Ser Tyr Thr Ser Thr Ala Val Ile Pro Asn Cys Gly Thr Pro Lys Gln
    930                 935                 940

Arg Ile Thr Ile Leu Gln Asn Ala Ser Ile Thr Pro Val Lys Ser Lys
945                 950                 955                 960

Thr Ser Thr Glu Asp Leu Met Asn Leu Glu Gln Gly Met Ser Pro Ile
                965                 970                 975

Thr Met Ala Thr Phe Ala Arg Ala Gln Thr Pro Glu Ser Cys Gly Ser
            980                 985                 990

Leu Thr Pro Glu Arg Thr Met Ser Pro Ile Gln Val Leu Ala Val Thr
        995                 1000                1005

Gly Ser Ala Ser Ser Pro Glu Gln Gly Arg Ser Pro Glu Pro Thr
        1010                1015                1020

Glu Ile Ser Ala Lys His Ala Ile Phe Arg Val Ser Pro Asp Arg
        1025                1030                1035

Gln Ser Ser Trp Gln Phe Arg Ser Asn Ser Asn Ser Ser Ser
        1040                1045                1050

Val Ile Thr Thr Glu Asp Asn Lys Ile His Ile His Leu Gly Ser
        1055                1060                1065

Pro Tyr Met Gln Ala Val Ala Ser Pro Val Arg Pro Ala Ser Pro
        1070                1075                1080

Ser Ala Pro Leu Gln Asp Asn Arg Thr Gln Gly Leu Ile Asn Gly
        1085                1090                1095

Ala Leu Asn Lys Thr Thr Asn Lys Val Thr Ser Ser Ile Thr Ile
        1100                1105                1110

Thr Pro Thr Ala Thr Pro Leu Pro Arg Gln Ser Gln Ile Thr Val
        1115                1120                1125

Glu Pro Leu Leu Leu Pro His
        1130                1135

<210> SEQ ID NO 13
<211> LENGTH: 3415
<212> TYPE: DNA
<213> ORGANISM: Homo sapiens
<220> FEATURE:
<221> NAME/KEY: misc_feature
<223> OTHER INFORMATION: GIP130b
<220> FEATURE:
<221> NAME/KEY: CDS
<222> LOCATION: (12)..(3410)
<223> OTHER INFORMATION:
```

-continued

```
<400> SEQUENCE: 13
ggctttaaag a atg cgt tcc aga ggc agt gat acc gag ggc tca gcc caa              50
           Met Arg Ser Arg Gly Ser Asp Thr Glu Gly Ser Ala Gln
             1               5                  10 aag aaa ttt cca aga cat act aaa ggc cac agt ttc caa ggg cct aaa              98
Lys Lys Phe Pro Arg His Thr Lys Gly His Ser Phe Gln Gly Pro Lys
 15              20                  25 aac atg aag cat aga cag caa gac aaa gac tcc ccc agt gag tcg gat             146
Asn Met Lys His Arg Gln Gln Asp Lys Asp Ser Pro Ser Glu Ser Asp
 30              35                  40                  45 gta ata ctt ccg tgt ccc aag gca gag aag cca cac agt ggt aat ggc             194
Val Ile Leu Pro Cys Pro Lys Ala Glu Lys Pro His Ser Gly Asn Gly
                 50                  55                  60 cac caa gca gaa gac ctc tca aga gat gac ctg tta ttt ctc ctc agc             242
His Gln Ala Glu Asp Leu Ser Arg Asp Asp Leu Leu Phe Leu Leu Ser
             65                  70                  75 att ctg gag gga gaa ctg cag gct cga gat gag gtc ata ggc att tta             290
Ile Leu Glu Gly Glu Leu Gln Ala Arg Asp Glu Val Ile Gly Ile Leu
         80                  85                  90 aag gct gaa aaa atg gac ctg gct ttg ctg gaa gct cag tat ggg ttt             338
Lys Ala Glu Lys Met Asp Leu Ala Leu Leu Glu Ala Gln Tyr Gly Phe
     95                 100                 105 gtc act cca aaa aag gtg tta gag gct ctc cag aga gat gct ttt caa             386
Val Thr Pro Lys Lys Val Leu Glu Ala Leu Gln Arg Asp Ala Phe Gln
110                 115                 120                 125 gcg aaa tct acc cct tgg cag gag gac atc tat gag aaa cca atg aat             434
Ala Lys Ser Thr Pro Trp Gln Glu Asp Ile Tyr Glu Lys Pro Met Asn
                130                 135                 140 gag ttg gac aaa gtt gtg gaa aaa cat aaa gaa tct tac aga cga atc             482
Glu Leu Asp Lys Val Val Glu Lys His Lys Glu Ser Tyr Arg Arg Ile
            145                 150                 155 ctg gga cag ctt tta gtg gca gaa aaa tcc cat agg caa acc ata ttg             530
Leu Gly Gln Leu Leu Val Ala Glu Lys Ser His Arg Gln Thr Ile Leu
        160                 165                 170 gag ttg gag gaa gaa aag aga aaa cat aaa gaa tac atg gag aag agt             578
Glu Leu Glu Glu Glu Lys Arg Lys His Lys Glu Tyr Met Glu Lys Ser
    175                 180                 185 gat gaa ttc ata tgc cta cta gaa cag gaa tgt gaa aga tta aag aag             626
Asp Glu Phe Ile Cys Leu Leu Glu Gln Glu Cys Glu Arg Leu Lys Lys
190                 195                 200                 205 cta att gat caa gaa atc aag tct cag gag gag aag gag caa gaa aag             674
Leu Ile Asp Gln Glu Ile Lys Ser Gln Glu Glu Lys Glu Gln Glu Lys
                210                 215                 220 gag aaa agg gtc acc acc ctg aaa gag gag ctg acc aag ctg aag tct             722
Glu Lys Arg Val Thr Thr Leu Lys Glu Glu Leu Thr Lys Leu Lys Ser
            225                 230                 235 ttt gct ttg atg gtg gtg gat gaa cag caa agg ctg acg gca cag ctc             770
Phe Ala Leu Met Val Val Asp Glu Gln Gln Arg Leu Thr Ala Gln Leu
        240                 245                 250 acc ctt caa aga cag aaa atc caa gag ctg acc aca aat gca aag gaa             818
Thr Leu Gln Arg Gln Lys Ile Gln Glu Leu Thr Thr Asn Ala Lys Glu
    255                 260                 265 aca cat acc aaa cta gcc ctt gct gaa gcc aga gtt cag gag gaa gag             866
Thr His Thr Lys Leu Ala Leu Ala Glu Ala Arg Val Gln Glu Glu Glu
270                 275                 280                 285 cag aag gca acc aga cta gag aag gaa ctg caa acg cag acc aca aag             914
Gln Lys Ala Thr Arg Leu Glu Lys Glu Leu Gln Thr Gln Thr Thr Lys
                290                 295                 300
```

```
ttt cac caa gac caa gac aca att atg gcg aag ctc acc aat gag gac        962
Phe His Gln Asp Gln Asp Thr Ile Met Ala Lys Leu Thr Asn Glu Asp
            305                 310                 315 agt caa aat cgc cag ctt caa caa aag ctg gca gca ctc agc cgg cag       1010
Ser Gln Asn Arg Gln Leu Gln Gln Lys Leu Ala Ala Leu Ser Arg Gln
        320                 325                 330 att gat gag tta gaa gag aca aac agg tct tta cga aaa gca gaa gag       1058
Ile Asp Glu Leu Glu Glu Thr Asn Arg Ser Leu Arg Lys Ala Glu Glu
335                 340                 345 gag ctg caa gat ata aaa gaa aaa atc agt aag gga gaa tat gga aac       1106
Glu Leu Gln Asp Ile Lys Glu Lys Ile Ser Lys Gly Glu Tyr Gly Asn
350                 355                 360                 365 gct ggt atc atg gct gaa gtg gaa gag ctc agg aaa cgt gtg cta gat       1154
Ala Gly Ile Met Ala Glu Val Glu Glu Leu Arg Lys Arg Val Leu Asp
                370                 375                 380 atg gaa ggg aaa gat gaa gag ctc ata aaa atg gag gag cag tgc aga       1202
Met Glu Gly Lys Asp Glu Glu Leu Ile Lys Met Glu Glu Gln Cys Arg
            385                 390                 395 gat ctc aat aag agg ctt gaa agg gag acg tta cag agt aaa gac ttt       1250
Asp Leu Asn Lys Arg Leu Glu Arg Glu Thr Leu Gln Ser Lys Asp Phe
        400                 405                 410 aaa cta gag gtt gaa aaa ctc agt aaa aga att atg gct ctg gaa aag       1298
Lys Leu Glu Val Glu Lys Leu Ser Lys Arg Ile Met Ala Leu Glu Lys
    415                 420                 425 tta gaa gac gct ttc aac aaa agc aaa caa gaa tgc tac tct ctg aaa       1346
Leu Glu Asp Ala Phe Asn Lys Ser Lys Gln Glu Cys Tyr Ser Leu Lys
430                 435                 440                 445 tgc aat tta gaa aaa gaa agg atg acc aca aag cag ttg tct caa gaa       1394
Cys Asn Leu Glu Lys Glu Arg Met Thr Thr Lys Gln Leu Ser Gln Glu
                450                 455                 460 ctg gag agt tta aaa gta agg atc aaa gag cta gaa gcc att gaa agt       1442
Leu Glu Ser Leu Lys Val Arg Ile Lys Glu Leu Glu Ala Ile Glu Ser
            465                 470                 475 cgg cta gaa aag aca gaa ttc act cta aaa gag gat tta act aaa ctg       1490
Arg Leu Glu Lys Thr Glu Phe Thr Leu Lys Glu Asp Leu Thr Lys Leu
        480                 485                 490 aaa aca tta act gtg atg ttt gta gat gaa cgg aaa aca atg agt gaa       1538
Lys Thr Leu Thr Val Met Phe Val Asp Glu Arg Lys Thr Met Ser Glu
    495                 500                 505 aaa tta aag aaa act gaa gat aaa tta caa gct gct tct tct cag ctt       1586
Lys Leu Lys Lys Thr Glu Asp Lys Leu Gln Ala Ala Ser Ser Gln Leu
510                 515                 520                 525 caa gtg gag caa aat aaa gta aca aca gtt act gag aag tta att gag       1634
Gln Val Glu Gln Asn Lys Val Thr Thr Val Thr Glu Lys Leu Ile Glu
                530                 535                 540 gaa act aaa agg gcg ctc aag tcc aaa acc gat gta gaa gaa aag atg       1682
Glu Thr Lys Arg Ala Leu Lys Ser Lys Thr Asp Val Glu Glu Lys Met
            545                 550                 555 tac agc gta acc aag gag aga gat gat tta aaa aac aaa ttg aaa gcg       1730
Tyr Ser Val Thr Lys Glu Arg Asp Asp Leu Lys Asn Lys Leu Lys Ala
        560                 565                 570 gaa gaa gag aaa gga aat gat ctc ctg tca aga gtt aat atg ttg aaa       1778
Glu Glu Glu Lys Gly Asn Asp Leu Leu Ser Arg Val Asn Met Leu Lys
    575                 580                 585 aat agg ctt caa tca ttg gaa gca att gag aaa gat ttc cta aaa aac       1826
Asn Arg Leu Gln Ser Leu Glu Ala Ile Glu Lys Asp Phe Leu Lys Asn
590                 595                 600                 605 aaa tta aat caa gac tct ggg aaa tcc aca aca gca tta cac caa gaa       1874
Lys Leu Asn Gln Asp Ser Gly Lys Ser Thr Thr Ala Leu His Gln Glu
                610                 615                 620
```

```
aac aat aag att aag gag ctc tct caa gaa gtg gaa aga ctg aaa ctg      1922
Asn Asn Lys Ile Lys Glu Leu Ser Gln Glu Val Glu Arg Leu Lys Leu
            625                 630                 635 aag cta aag gac atg aaa gcc att gag gat gac ctc atg aaa aca gaa      1970
Lys Leu Lys Asp Met Lys Ala Ile Glu Asp Asp Leu Met Lys Thr Glu
        640                 645                 650 gat gaa tat gag act cta gaa cga agg tat gct aat gaa cga gac aaa      2018
Asp Glu Tyr Glu Thr Leu Glu Arg Arg Tyr Ala Asn Glu Arg Asp Lys
    655                 660                 665 gct caa ttt tta tct aaa gag cta gaa cat gtt aaa atg gaa ctt gct      2066
Ala Gln Phe Leu Ser Lys Glu Leu Glu His Val Lys Met Glu Leu Ala
670                 675                 680                 685 aag tac aag tta gca gaa aag aca gag acc agc cat gaa caa tgg ctt      2114
Lys Tyr Lys Leu Ala Glu Lys Thr Glu Thr Ser His Glu Gln Trp Leu
            690                 695                 700 ttc aaa agg ctt caa gaa gaa gaa gct aag tca ggg cac ctc tca aga      2162
Phe Lys Arg Leu Gln Glu Glu Glu Ala Lys Ser Gly His Leu Ser Arg
        705                 710                 715 gaa gtg gat gca tta aaa gag aaa att cat gaa tac atg gca act gaa      2210
Glu Val Asp Ala Leu Lys Glu Lys Ile His Glu Tyr Met Ala Thr Glu
    720                 725                 730 gac cta ata tgt cac ctc cag gga gat cac tca gtc ctg caa aaa aaa      2258
Asp Leu Ile Cys His Leu Gln Gly Asp His Ser Val Leu Gln Lys Lys
735                 740                 745 cta aat caa caa gaa aac agg aac aga gat tta gga aga gag att gaa      2306
Leu Asn Gln Gln Glu Asn Arg Asn Arg Asp Leu Gly Arg Glu Ile Glu
750                 755                 760                 765 aac ctc act aag gag tta gag agg tac cgg cat ttc agt aag agc ctc      2354
Asn Leu Thr Lys Glu Leu Glu Arg Tyr Arg His Phe Ser Lys Ser Leu
            770                 775                 780 agg cct agt ctc aat gga aga aga att tcc gat cct caa gta ttt tct      2402
Arg Pro Ser Leu Asn Gly Arg Arg Ile Ser Asp Pro Gln Val Phe Ser
        785                 790                 795 aaa gaa gtt cag aca gaa gca gta gac aat gaa cca cct gat tac aag      2450
Lys Glu Val Gln Thr Glu Ala Val Asp Asn Glu Pro Pro Asp Tyr Lys
    800                 805                 810 agc ctc att cct ctg gaa cgt gca gtc atc aat ggt cag tta tat gag      2498
Ser Leu Ile Pro Leu Glu Arg Ala Val Ile Asn Gly Gln Leu Tyr Glu
815                 820                 825 gag agt gag aat caa gac gag gac cct aat gat gag gga tct gtg ctg      2546
Glu Ser Glu Asn Gln Asp Glu Asp Pro Asn Asp Glu Gly Ser Val Leu
830                 835                 840                 845 tcc ttc aaa tgc agc cag tct act cca tgt cct gtt aac aga aag cta      2594
Ser Phe Lys Cys Ser Gln Ser Thr Pro Cys Pro Val Asn Arg Lys Leu
            850                 855                 860 tgg att ccc tgg atg aaa tcc aag gag ggc cat ctt cag aat gga aaa      2642
Trp Ile Pro Trp Met Lys Ser Lys Glu Gly His Leu Gln Asn Gly Lys
        865                 870                 875 atg caa act aaa ccc aat gcc aac ttt gtg caa cct gga gat cta gtc      2690
Met Gln Thr Lys Pro Asn Ala Asn Phe Val Gln Pro Gly Asp Leu Val
    880                 885                 890 cta agc cac aca cct ggg cag cca ctt cat ata aag gtt act cca gac      2738
Leu Ser His Thr Pro Gly Gln Pro Leu His Ile Lys Val Thr Pro Asp
895                 900                 905 cat gta caa aac aca gcc act ctt gaa atc aca agt cca acc aca gag      2786
His Val Gln Asn Thr Ala Thr Leu Glu Ile Thr Ser Pro Thr Thr Glu
910                 915                 920                 925 agt cct cac tct tac acg agt act gca gtg ata ccg aac tgt ggc acg      2834
Ser Pro His Ser Tyr Thr Ser Thr Ala Val Ile Pro Asn Cys Gly Thr
```

-continued

```
            930              935              940
cca aag caa agg ata acc atc ctc caa aac gcc tcc ata aca cca gta        2882
Pro Lys Gln Arg Ile Thr Ile Leu Gln Asn Ala Ser Ile Thr Pro Val
            945              950              955 aag tcc aaa acc tct acc gaa gac ctc atg aat tta gaa caa ggc atg        2930
Lys Ser Lys Thr Ser Thr Glu Asp Leu Met Asn Leu Glu Gln Gly Met
        960              965              970 tcc cca att acc atg gca acc ttt gcc aga gca cag acc cca gag tct        2978
Ser Pro Ile Thr Met Ala Thr Phe Ala Arg Ala Gln Thr Pro Glu Ser
    975              980              985 tgt ggt tct cta act cca gaa agg aca atg tcc cct att cag gtt ttg        3026
Cys Gly Ser Leu Thr Pro Glu Arg Thr Met Ser Pro Ile Gln Val Leu
990              995              1000             1005 gct gtg act ggt tca gct agc tct cct gag cag gga cgc tcc cca            3071
Ala Val Thr Gly Ser Ala Ser Ser Pro Glu Gln Gly Arg Ser Pro
                1010             1015             1020 gaa cca aca gaa atc agt gcc aag cat gcg ata ttc aga gtc tcc            3116
Glu Pro Thr Glu Ile Ser Ala Lys His Ala Ile Phe Arg Val Ser
            1025             1030             1035 cca gac cgg cag tca tca tgg cag ttt cag cgt tca aac agc aat            3161
Pro Asp Arg Gln Ser Ser Trp Gln Phe Gln Arg Ser Asn Ser Asn
            1040             1045             1050 agc tca agt gtg ata act act gag gat aat aaa atc cac att cac            3206
Ser Ser Ser Val Ile Thr Thr Glu Asp Asn Lys Ile His Ile His
            1055             1060             1065 tta gga agt cct tac atg caa gct gta gcc agc cct gtg aga cct            3251
Leu Gly Ser Pro Tyr Met Gln Ala Val Ala Ser Pro Val Arg Pro
            1070             1075             1080 gcc agc cct tca gca cca ctg cag gat aac cga act caa ggc tta            3296
Ala Ser Pro Ser Ala Pro Leu Gln Asp Asn Arg Thr Gln Gly Leu
            1085             1090             1095 att aac ggg gca cta aac aaa aca acc aat aaa gtc acc agc agt            3341
Ile Asn Gly Ala Leu Asn Lys Thr Thr Asn Lys Val Thr Ser Ser
            1100             1105             1110 att act atc aca cca aca gcc aca cct ctt cct cga caa tca caa            3386
Ile Thr Ile Thr Pro Thr Ala Thr Pro Leu Pro Arg Gln Ser Gln
            1115             1120             1125 att aca gta agt aat ata tat aac tgacc                                  3415
Ile Thr Val Ser Asn Ile Tyr Asn
            1130
```

<210> SEQ ID NO 14
<211> LENGTH: 1133
<212> TYPE: PRT
<213> ORGANISM: Homo sapiens

<400> SEQUENCE: 14

```
Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
                20                  25                  30

His Arg Gln Gln Asp Lys Asp Ser Pro Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Asp Leu Leu Phe Leu Ser Ile Leu Glu
65                  70                  75                  80

Gly Glu Leu Gln Ala Arg Asp Glu Val Ile Gly Ile Leu Lys Ala Glu
                85                  90                  95
```

```
Lys Met Asp Leu Ala Leu Leu Glu Ala Gln Tyr Gly Phe Val Thr Pro
            100                 105                 110
Lys Lys Val Leu Glu Ala Leu Gln Arg Asp Ala Phe Gln Ala Lys Ser
            115                 120                 125
Thr Pro Trp Gln Glu Asp Ile Tyr Glu Lys Pro Met Asn Glu Leu Asp
            130                 135                 140
Lys Val Val Glu Lys His Lys Glu Ser Tyr Arg Arg Ile Leu Gly Gln
145                 150                 155                 160
Leu Leu Val Ala Glu Lys Ser His Arg Gln Thr Ile Leu Glu Leu Glu
                165                 170                 175
Glu Glu Lys Arg Lys His Lys Glu Tyr Met Glu Lys Ser Asp Glu Phe
            180                 185                 190
Ile Cys Leu Leu Glu Gln Glu Cys Glu Arg Leu Lys Lys Leu Ile Asp
            195                 200                 205
Gln Glu Ile Lys Ser Gln Glu Glu Lys Glu Gln Glu Lys Glu Lys Arg
            210                 215                 220
Val Thr Thr Leu Lys Glu Glu Leu Thr Lys Leu Lys Ser Phe Ala Leu
225                 230                 235                 240
Met Val Val Asp Glu Gln Gln Arg Leu Thr Ala Gln Leu Thr Leu Gln
                245                 250                 255
Arg Gln Lys Ile Gln Glu Leu Thr Thr Asn Ala Lys Glu Thr His Thr
            260                 265                 270
Lys Leu Ala Leu Ala Glu Ala Arg Val Gln Glu Glu Glu Gln Lys Ala
            275                 280                 285
Thr Arg Leu Glu Lys Glu Leu Gln Thr Gln Thr Lys Phe His Gln
            290                 295                 300
Asp Gln Asp Thr Ile Met Ala Lys Leu Thr Asn Glu Asp Ser Gln Asn
305                 310                 315                 320
Arg Gln Leu Gln Gln Lys Leu Ala Ala Leu Ser Arg Gln Ile Asp Glu
                325                 330                 335
Leu Glu Glu Thr Asn Arg Ser Leu Arg Lys Ala Glu Glu Glu Leu Gln
            340                 345                 350
Asp Ile Lys Glu Lys Ile Ser Lys Gly Glu Tyr Gly Asn Ala Gly Ile
            355                 360                 365
Met Ala Glu Val Glu Glu Leu Arg Lys Arg Val Leu Asp Met Glu Gly
            370                 375                 380
Lys Asp Glu Glu Leu Ile Lys Met Glu Glu Gln Cys Arg Asp Leu Asn
385                 390                 395                 400
Lys Arg Leu Glu Arg Glu Thr Leu Gln Ser Lys Asp Phe Lys Leu Glu
                405                 410                 415
Val Glu Lys Leu Ser Lys Arg Ile Met Ala Leu Glu Lys Leu Glu Asp
            420                 425                 430
Ala Phe Asn Lys Ser Lys Gln Glu Cys Tyr Ser Leu Lys Cys Asn Leu
            435                 440                 445
Glu Lys Glu Arg Met Thr Thr Lys Gln Leu Ser Gln Glu Leu Glu Ser
            450                 455                 460
Leu Lys Val Arg Ile Lys Glu Leu Glu Ala Ile Glu Ser Arg Leu Glu
465                 470                 475                 480
Lys Thr Glu Phe Thr Leu Lys Glu Asp Leu Thr Lys Leu Lys Thr Leu
                485                 490                 495
Thr Val Met Phe Val Asp Glu Arg Lys Thr Met Ser Glu Lys Leu Lys
            500                 505                 510
```

```
Lys Thr Glu Asp Lys Leu Gln Ala Ala Ser Ser Gln Leu Gln Val Glu
            515                 520                 525

Gln Asn Lys Val Thr Val Thr Glu Lys Leu Ile Glu Glu Thr Lys
    530                 535                 540

Arg Ala Leu Lys Ser Lys Thr Asp Val Glu Glu Lys Met Tyr Ser Val
545                 550                 555                 560

Thr Lys Glu Arg Asp Asp Leu Lys Asn Lys Leu Lys Ala Glu Glu
                565                 570                 575

Lys Gly Asn Asp Leu Leu Ser Arg Val Asn Met Leu Lys Asn Arg Leu
            580                 585                 590

Gln Ser Leu Glu Ala Ile Glu Lys Asp Phe Leu Lys Asn Lys Leu Asn
    595                 600                 605

Gln Asp Ser Gly Lys Ser Thr Thr Ala Leu His Gln Glu Asn Asn Lys
    610                 615                 620

Ile Lys Glu Leu Ser Gln Glu Val Glu Arg Leu Lys Leu Lys Leu Lys
625                 630                 635                 640

Asp Met Lys Ala Ile Glu Asp Asp Leu Met Lys Thr Glu Asp Glu Tyr
            645                 650                 655

Glu Thr Leu Glu Arg Arg Tyr Ala Asn Glu Arg Asp Lys Ala Gln Phe
            660                 665                 670

Leu Ser Lys Glu Leu Glu His Val Lys Met Glu Leu Ala Lys Tyr Lys
    675                 680                 685

Leu Ala Glu Lys Thr Glu Thr Ser His Glu Gln Trp Leu Phe Lys Arg
    690                 695                 700

Leu Gln Glu Glu Glu Ala Lys Ser Gly His Leu Ser Arg Glu Val Asp
705                 710                 715                 720

Ala Leu Lys Glu Lys Ile His Glu Tyr Met Ala Thr Glu Asp Leu Ile
                725                 730                 735

Cys His Leu Gln Gly Asp His Ser Val Leu Gln Lys Lys Leu Asn Gln
            740                 745                 750

Gln Glu Asn Arg Asn Arg Asp Leu Gly Arg Glu Ile Glu Asn Leu Thr
    755                 760                 765

Lys Glu Leu Glu Arg Tyr Arg His Phe Ser Lys Ser Leu Arg Pro Ser
    770                 775                 780

Leu Asn Gly Arg Arg Ile Ser Asp Pro Gln Val Phe Ser Lys Glu Val
785                 790                 795                 800

Gln Thr Glu Ala Val Asp Asn Glu Pro Asp Tyr Lys Ser Leu Ile
                805                 810                 815

Pro Leu Glu Arg Ala Val Ile Asn Gly Gln Leu Tyr Glu Glu Ser Glu
            820                 825                 830

Asn Gln Asp Glu Asp Pro Asn Asp Glu Gly Ser Val Leu Ser Phe Lys
    835                 840                 845

Cys Ser Gln Ser Thr Pro Cys Pro Val Asn Arg Lys Leu Trp Ile Pro
    850                 855                 860

Trp Met Lys Ser Lys Glu Gly His Leu Gln Asn Gly Lys Met Gln Thr
865                 870                 875                 880

Lys Pro Asn Ala Asn Phe Val Gln Pro Gly Asp Leu Val Leu Ser His
                885                 890                 895

Thr Pro Gly Gln Pro Leu His Ile Lys Val Thr Pro Asp His Val Gln
            900                 905                 910

Asn Thr Ala Thr Leu Glu Ile Thr Ser Pro Thr Thr Glu Ser Pro His
    915                 920                 925

Ser Tyr Thr Ser Thr Ala Val Ile Pro Asn Cys Gly Thr Pro Lys Gln
```

```
                    930             935             940
Arg Ile Thr Ile Leu Gln Asn Ala Ser Ile Thr Pro Val Lys Ser Lys
945                 950             955                 960

Thr Ser Thr Glu Asp Leu Met Asn Leu Glu Gln Gly Met Ser Pro Ile
                965             970                 975

Thr Met Ala Thr Phe Ala Arg Ala Gln Thr Pro Glu Ser Cys Gly Ser
            980             985                 990

Leu Thr Pro Glu Arg Thr Met Ser Pro Ile Gln Val Leu Ala Val Thr
        995             1000            1005

Gly Ser Ala Ser Ser Pro Glu Gln Gly Arg Ser Pro Glu Pro Thr
    1010            1015            1020

Glu Ile Ser Ala Lys His Ala Ile Phe Arg Val Ser Pro Asp Arg
    1025            1030            1035

Gln Ser Ser Trp Gln Phe Gln Arg Ser Asn Ser Asn Ser Ser Ser
    1040            1045            1050

Val Ile Thr Thr Glu Asp Asn Lys Ile His Ile His Leu Gly Ser
    1055            1060            1065

Pro Tyr Met Gln Ala Val Ala Ser Pro Val Arg Pro Ala Ser Pro
    1070            1075            1080

Ser Ala Pro Leu Gln Asp Asn Arg Thr Gln Gly Leu Ile Asn Gly
    1085            1090            1095

Ala Leu Asn Lys Thr Thr Asn Lys Val Thr Ser Ser Ile Thr Ile
    1100            1105            1110

Thr Pro Thr Ala Thr Pro Leu Pro Arg Gln Ser Gln Ile Thr Val
    1115            1120            1125

Ser Asn Ile Tyr Asn
    1130

<210> SEQ ID NO 15
<211> LENGTH: 3416
<212> TYPE: DNA
<213> ORGANISM: Homo sapiens
<220> FEATURE:
<221> NAME/KEY: misc_feature
<223> OTHER INFORMATION: GIP130c
<220> FEATURE:
<221> NAME/KEY: CDS
<222> LOCATION: (9)..(3407)
<223> OTHER INFORMATION:

<400> SEQUENCE: 15 tttaaaga atg cgt tcc aga ggc agt gat acc gag ggc tca gcc caa aag     50
        Met Arg Ser Arg Gly Ser Asp Thr Glu Gly Ser Ala Gln Lys
        1               5                   10 aaa ttt cca aga cat act aaa ggc cac agt ttc caa ggg cct aaa aac     98
Lys Phe Pro Arg His Thr Lys Gly His Ser Phe Gln Gly Pro Lys Asn
15                  20                  25                  30 atg aag cat aga cag caa gac aaa gac tcc ccc agt gag tcg gat gta    146
Met Lys His Arg Gln Gln Asp Lys Asp Ser Pro Ser Glu Ser Asp Val
                35                  40                  45 ata ctt ccg tgt ccc aag gca gag aag cca cac agt ggt aat ggc cac    194
Ile Leu Pro Cys Pro Lys Ala Glu Lys Pro His Ser Gly Asn Gly His
            50                  55                  60 caa gca gaa gac ctc tca aga gat gac ctg tta ttt ctc ctc agc att    242
Gln Ala Glu Asp Leu Ser Arg Asp Asp Leu Leu Phe Leu Leu Ser Ile
        65                  70                  75 ctg gag gga gaa ctg cag gct cga gat gag gtc ata ggc att tta aag    290
Leu Glu Gly Glu Leu Gln Ala Arg Asp Glu Val Ile Gly Ile Leu Lys
    80                  85                  90
```

```
gct gaa aaa atg gac ctg gct ttg ctg gaa gct cag tat ggg ttt gtc       338
Ala Glu Lys Met Asp Leu Ala Leu Leu Glu Ala Gln Tyr Gly Phe Val
 95             100                 105                 110 act cca aaa aag gtg tta gag gct ctc cag aga gat gct ttt caa gcg       386
Thr Pro Lys Lys Val Leu Glu Ala Leu Gln Arg Asp Ala Phe Gln Ala
                115                 120                 125 aaa tct acc cct tgg cag gag gac atc tat gag aaa cca atg aat gag       434
Lys Ser Thr Pro Trp Gln Glu Asp Ile Tyr Glu Lys Pro Met Asn Glu
            130                 135                 140 ttg gac aaa gtt gtg gaa aaa cat aaa gaa tct tac aga cga atc ctg       482
Leu Asp Lys Val Val Glu Lys His Lys Glu Ser Tyr Arg Arg Ile Leu
        145                 150                 155 gga cag ctt tta gtg gca gaa aaa tcc cgt agg caa acc ata ttg gag       530
Gly Gln Leu Leu Val Ala Glu Lys Ser Arg Arg Gln Thr Ile Leu Glu
    160                 165                 170 ttg gag gaa gaa aag aga aaa cat aaa gaa tac atg gag aag agt gat       578
Leu Glu Glu Glu Lys Arg Lys His Lys Glu Tyr Met Glu Lys Ser Asp
175                 180                 185                 190 gaa ttc ata tgc cta cta gaa cag gaa tgt gaa aga tta aag aag cta       626
Glu Phe Ile Cys Leu Leu Glu Gln Glu Cys Glu Arg Leu Lys Lys Leu
                195                 200                 205 att gat caa gaa atc aag tct cag gag gag aag gag caa gaa aag gag       674
Ile Asp Gln Glu Ile Lys Ser Gln Glu Glu Lys Glu Gln Glu Lys Glu
            210                 215                 220 aaa agg gtc acc acc ctg aaa gag gag ctg acc aag ctg aag tct ttt       722
Lys Arg Val Thr Thr Leu Lys Glu Glu Leu Thr Lys Leu Lys Ser Phe
        225                 230                 235 gct ttg atg gtg gtg gat gaa cag caa agg ctg acg gca cag ctc acc       770
Ala Leu Met Val Val Asp Glu Gln Gln Arg Leu Thr Ala Gln Leu Thr
    240                 245                 250 ctt caa aga cag aaa atc caa gag ctg acc aca aat gca aag gaa aca       818
Leu Gln Arg Gln Lys Ile Gln Glu Leu Thr Thr Asn Ala Lys Glu Thr
255                 260                 265                 270 cat acc aaa cta gcc ctt gct gaa gcc aga gtt cag gag gaa gag cag       866
His Thr Lys Leu Ala Leu Ala Glu Ala Arg Val Gln Glu Glu Glu Gln
                275                 280                 285 aag gca acc aga cta gag aag gaa ctg caa acg cag acc aca aag ttt       914
Lys Ala Thr Arg Leu Glu Lys Glu Leu Gln Thr Gln Thr Thr Lys Phe
            290                 295                 300 cac caa gac caa gac aca att atg gcg aag ctc acc aat gag gac agt       962
His Gln Asp Gln Asp Thr Ile Met Ala Lys Leu Thr Asn Glu Asp Ser
        305                 310                 315 caa aat cgc cag ctt caa caa aag ctg gca gca ctc agc cgg cag att      1010
Gln Asn Arg Gln Leu Gln Gln Lys Leu Ala Ala Leu Ser Arg Gln Ile
    320                 325                 330 gat gag tta gaa gag aca aac agg tct tta cga aaa gca gaa gag gag      1058
Asp Glu Leu Glu Glu Thr Asn Arg Ser Leu Arg Lys Ala Glu Glu Glu
335                 340                 345                 350 ctg caa gat ata aaa gaa aaa atc agt aag gga gaa tat gga aac gct      1106
Leu Gln Asp Ile Lys Glu Lys Ile Ser Lys Gly Glu Tyr Gly Asn Ala
                355                 360                 365 ggt atc atg gct gaa gtg gaa gag ctc agg aaa cgt gtg cta gat atg      1154
Gly Ile Met Ala Glu Val Glu Glu Leu Arg Lys Arg Val Leu Asp Met
            370                 375                 380 gaa ggg aaa gat gaa gag ctc ata aaa atg gag gag cag tgc aga gat      1202
Glu Gly Lys Asp Glu Glu Leu Ile Lys Met Glu Glu Gln Cys Arg Asp
        385                 390                 395 ctc aat aag agg ctt gaa agg gag acg tta cag agt aaa gac ttt aaa      1250
Leu Asn Lys Arg Leu Glu Arg Glu Thr Leu Gln Ser Lys Asp Phe Lys
```

-continued

```
            400                 405                 410
cta gag gtt gaa aaa ctc agt aaa aga att atg gct ctg gaa aag tta      1298
Leu Glu Val Glu Lys Leu Ser Lys Arg Ile Met Ala Leu Glu Lys Leu
415                 420                 425                 430 gaa gac gct ttc aac aaa agc aaa caa gaa tgc tac tct ctg aaa tgc      1346
Glu Asp Ala Phe Asn Lys Ser Lys Gln Glu Cys Tyr Ser Leu Lys Cys
                435                 440                 445 aat tta gaa aaa gaa agg atg acc aca aag cag ttg tct caa gaa ctg      1394
Asn Leu Glu Lys Glu Arg Met Thr Thr Lys Gln Leu Ser Gln Glu Leu
        450                 455                 460 gag agt tta aaa gta agg atc aaa gag cta gaa gcc att gaa agt cgg      1442
Glu Ser Leu Lys Val Arg Ile Lys Glu Leu Glu Ala Ile Glu Ser Arg
    465                 470                 475 cta gaa aag aca gaa ttc act cta aaa gag gat tta act aaa ctg aaa      1490
Leu Glu Lys Thr Glu Phe Thr Leu Lys Glu Asp Leu Thr Lys Leu Lys
480                 485                 490 aca tta act gtg atg ttt gta gat gaa cgg aaa aca atg agt gaa aaa      1538
Thr Leu Thr Val Met Phe Val Asp Glu Arg Lys Thr Met Ser Glu Lys
495                 500                 505                 510 tta aag aaa act gaa gat aaa tta caa gct gct tct tct cag ctt caa      1586
Leu Lys Lys Thr Glu Asp Lys Leu Gln Ala Ala Ser Ser Gln Leu Gln
                515                 520                 525 gtg gag caa aat aaa gta aca aca gtt act gag aag tta att gag gaa      1634
Val Glu Gln Asn Lys Val Thr Thr Val Thr Glu Lys Leu Ile Glu Glu
        530                 535                 540 act aaa agg gcg ctc aag tcc aaa acc gat gta gaa gaa aag atg tac      1682
Thr Lys Arg Ala Leu Lys Ser Lys Thr Asp Val Glu Glu Lys Met Tyr
    545                 550                 555 agc gta acc aag gag aga gat gat tta aaa aac aaa ttg aaa gcg gaa      1730
Ser Val Thr Lys Glu Arg Asp Asp Leu Lys Asn Lys Leu Lys Ala Glu
560                 565                 570 gaa gag aaa gga aat gat ctc ctg tca aga gtt aat atg ttg aaa aat      1778
Glu Glu Lys Gly Asn Asp Leu Leu Ser Arg Val Asn Met Leu Lys Asn
575                 580                 585                 590 agg ctt caa tca ttg gaa gca att gag aaa gat ttc cta aaa aac aaa      1826
Arg Leu Gln Ser Leu Glu Ala Ile Glu Lys Asp Phe Leu Lys Asn Lys
                595                 600                 605 tta aat caa gac tct ggg aaa tcc aca aca gca tta cac caa gaa aac      1874
Leu Asn Gln Asp Ser Gly Lys Ser Thr Thr Ala Leu His Gln Glu Asn
        610                 615                 620 aat aag att aag gag ctc tct caa gaa gtg gaa aga ctg aaa ctg aag      1922
Asn Lys Ile Lys Glu Leu Ser Gln Glu Val Glu Arg Leu Lys Leu Lys
    625                 630                 635 cta aag gac atg aaa gcc att gag gat gac ctc atg aaa aca gaa gat      1970
Leu Lys Asp Met Lys Ala Ile Glu Asp Asp Leu Met Lys Thr Glu Asp
640                 645                 650 gaa tat gag act cta gaa cga agg tat gct aat gaa cga gac aaa gct      2018
Glu Tyr Glu Thr Leu Glu Arg Arg Tyr Ala Asn Glu Arg Asp Lys Ala
655                 660                 665                 670 caa ttt tta tct aaa gag cta gaa cat gtt aaa atg gaa ctt gct aag      2066
Gln Phe Leu Ser Lys Glu Leu Glu His Val Lys Met Glu Leu Ala Lys
                675                 680                 685 tac aag tta gca gaa aag aca gag acc agc cat gaa caa tgg ctt ttc      2114
Tyr Lys Leu Ala Glu Lys Thr Glu Thr Ser His Glu Gln Trp Leu Phe
        690                 695                 700 aaa agg ctt caa gaa gaa gaa gct aag tca ggg cac ctc tca aga gaa      2162
Lys Arg Leu Gln Glu Glu Glu Ala Lys Ser Gly His Leu Ser Arg Glu
    705                 710                 715 gtg gat gca tta aaa gag aaa att cat gaa tac atg gca act gaa gac      2210
Val Asp Ala Leu Lys Glu Lys Ile His Glu Tyr Met Ala Thr Glu Asp
```

```
Val Asp Ala Leu Lys Glu Lys Ile His Glu Tyr Met Ala Thr Glu Asp
    720                 725                 730 cta ata tgt cac ctc cag gga gat cac tca gtc ctg caa aaa aaa cta    2258
Leu Ile Cys His Leu Gln Gly Asp His Ser Val Leu Gln Lys Lys Leu
735                 740                 745                 750 aat caa caa gaa aac agg aac aga gat tta gga aga gag att gaa aac    2306
Asn Gln Gln Glu Asn Arg Asn Arg Asp Leu Gly Arg Glu Ile Glu Asn
                755                 760                 765 ctc act aag gag tta gag agg tac cgg cat ttc agt aag agc ctc agg    2354
Leu Thr Lys Glu Leu Glu Arg Tyr Arg His Phe Ser Lys Ser Leu Arg
        770                 775                 780 cct agt ctc aat gga aga aga att tcc gat cct caa gta ttt tct aaa    2402
Pro Ser Leu Asn Gly Arg Arg Ile Ser Asp Pro Gln Val Phe Ser Lys
            785                 790                 795 gaa gtt cag aca gaa gca gta gac aat gaa cca cct gat tac aag agc    2450
Glu Val Gln Thr Glu Ala Val Asp Asn Glu Pro Pro Asp Tyr Lys Ser
                800                 805                 810 ctc att cct ctg gaa cgt gca gtc atc aat ggt cag tta tat gag gag    2498
Leu Ile Pro Leu Glu Arg Ala Val Ile Asn Gly Gln Leu Tyr Glu Glu
815                 820                 825                 830 agt gag aat caa gac gag gac cct aat gat gag gga tct gtg ctg tcc    2546
Ser Glu Asn Gln Asp Glu Asp Pro Asn Asp Glu Gly Ser Val Leu Ser
                835                 840                 845 ttc aaa tgc agc cag tct act cca tgt cct gtt aac aga aag cta tgg    2594
Phe Lys Cys Ser Gln Ser Thr Pro Cys Pro Val Asn Arg Lys Leu Trp
            850                 855                 860 att ccc tgg atg aaa tcc aag gag ggc cat ctt cag aat gga aaa atg    2642
Ile Pro Trp Met Lys Ser Lys Glu Gly His Leu Gln Asn Gly Lys Met
        865                 870                 875 caa act aaa ccc aat gcc aac ttt gtg caa cct gga gat cta gtc cta    2690
Gln Thr Lys Pro Asn Ala Asn Phe Val Gln Pro Gly Asp Leu Val Leu
    880                 885                 890 agc cac aca cct ggg cag cca ctt cat ata aag gtt act cca gac cat    2738
Ser His Thr Pro Gly Gln Pro Leu His Ile Lys Val Thr Pro Asp His
895                 900                 905                 910 gta caa aac aca gcc act ctt gaa atc aca agt cca acc aca gag agt    2786
Val Gln Asn Thr Ala Thr Leu Glu Ile Thr Ser Pro Thr Thr Glu Ser
                915                 920                 925 cct cac tct tac acg agt act gca gtg ata ccg aac tgt ggc acg cca    2834
Pro His Ser Tyr Thr Ser Thr Ala Val Ile Pro Asn Cys Gly Thr Pro
            930                 935                 940 aag caa agg ata acc atc ctc caa aac gcc tcc ata aca cca gta aag    2882
Lys Gln Arg Ile Thr Ile Leu Gln Asn Ala Ser Ile Thr Pro Val Lys
        945                 950                 955 tcc aaa acc tct acc gaa gac ctc atg aat tta gaa caa ggc atg tcc    2930
Ser Lys Thr Ser Thr Glu Asp Leu Met Asn Leu Glu Gln Gly Met Ser
    960                 965                 970 cca att acc atg gca acc ttt gcc aga gca cag acc cca gag tct tgt    2978
Pro Ile Thr Met Ala Thr Phe Ala Arg Ala Gln Thr Pro Glu Ser Cys
975                 980                 985                 990 ggt tct cta act cca gaa agg aca atg tcc cct att cag gtt ttg gct    3026
Gly Ser Leu Thr Pro Glu Arg Thr Met Ser Pro Ile Gln Val Leu Ala
                995                 1000                1005 gtg act ggt tca gct agc tct cct gag cag gga cgc tcc cca gaa        3071
Val Thr Gly Ser Ala Ser Ser Pro Glu Gln Gly Arg Ser Pro Glu
                1010                1015                1020 cca aca gaa atc agt gcc aag cat gcg ata ttc aga gtc tcc cca        3116
Pro Thr Glu Ile Ser Ala Lys His Ala Ile Phe Arg Val Ser Pro
                1025                1030                1035
```

```
gac cgg cag tca tca tgg cag ttt cag cgt tca aac agc aat agc    3161
Asp Arg Gln Ser Ser Trp Gln Phe Gln Arg Ser Asn Ser Asn Ser
            1040                1045                1050 tca agt gtg ata act act gag gat aat aaa atc cac att cac tta    3206
Ser Ser Val Ile Thr Thr Glu Asp Asn Lys Ile His Ile His Leu
            1055                1060                1065 gga agt cct tac atg caa gct gta gcc agc cct gtg aga cct gcc    3251
Gly Ser Pro Tyr Met Gln Ala Val Ala Ser Pro Val Arg Pro Ala
            1070                1075                1080 agc cct tca gca cca ctg cag gat aac cga act caa ggc tta att    3296
Ser Pro Ser Ala Pro Leu Gln Asp Asn Arg Thr Gln Gly Leu Ile
            1085                1090                1095 aac ggg gca cta aac aaa aca acc aat aaa gtc acc agc agt att    3341
Asn Gly Ala Leu Asn Lys Thr Thr Asn Lys Val Thr Ser Ser Ile
            1100                1105                1110 act atc aca cca aca gcc aca cct ctt cct cga caa tca caa att    3386
Thr Ile Thr Pro Thr Ala Thr Pro Leu Pro Arg Gln Ser Gln Ile
            1115                1120                1125 aca gta agt aat ata tat aac tgaccacgc                          3416
Thr Val Ser Asn Ile Tyr Asn
            1130
```

<210> SEQ ID NO 16
<211> LENGTH: 1133
<212> TYPE: PRT
<213> ORGANISM: Homo sapiens

<400> SEQUENCE: 16

```
Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Leu Leu Phe Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

Thr Pro Trp Gln Glu Asp Ile Tyr Glu Lys Pro Met Asn Glu Leu Asp
    130                 135                 140

Lys Val Val Glu Lys His Lys Glu Ser Tyr Arg Arg Ile Leu Gly Gln
145                 150                 155                 160

Leu Leu Val Ala Glu Lys Ser Arg Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205

Gln Glu Ile Lys Ser Gln Glu Glu Lys Glu Gln Glu Lys Glu Lys Arg
    210                 215                 220

Val Thr Thr Leu Lys Glu Glu Leu Thr Lys Leu Lys Ser Phe Ala Leu
```

-continued

```
            225                 230                 235                 240
Met Val Asp Glu Gln Gln Arg Leu Thr Ala Gln Leu Thr Leu Gln
                245                 250                 255
Arg Gln Lys Ile Gln Glu Leu Thr Thr Asn Ala Lys Glu Thr His Thr
                260                 265                 270
Lys Leu Ala Leu Ala Glu Ala Arg Val Gln Glu Glu Gln Lys Ala
                275                 280                 285
Thr Arg Leu Glu Lys Glu Leu Gln Thr Gln Thr Lys Phe His Gln
            290                 295                 300
Asp Gln Asp Thr Ile Met Ala Lys Leu Thr Asn Glu Asp Ser Gln Asn
305                 310                 315                 320
Arg Gln Leu Gln Gln Lys Leu Ala Ala Leu Ser Arg Gln Ile Asp Glu
                325                 330                 335
Leu Glu Glu Thr Asn Arg Ser Leu Arg Lys Ala Glu Glu Leu Gln
                340                 345                 350
Asp Ile Lys Glu Lys Ile Ser Lys Gly Glu Tyr Gly Asn Ala Gly Ile
                355                 360                 365
Met Ala Glu Val Glu Glu Leu Arg Lys Arg Val Leu Asp Met Glu Gly
            370                 375                 380
Lys Asp Glu Glu Leu Ile Lys Met Glu Glu Gln Cys Arg Asp Leu Asn
385                 390                 395                 400
Lys Arg Leu Glu Arg Glu Thr Leu Gln Ser Lys Asp Phe Lys Leu Glu
                405                 410                 415
Val Glu Lys Leu Ser Lys Arg Ile Met Ala Leu Glu Lys Leu Glu Asp
                420                 425                 430
Ala Phe Asn Lys Ser Lys Gln Glu Cys Tyr Ser Leu Lys Cys Asn Leu
                435                 440                 445
Glu Lys Glu Arg Met Thr Thr Lys Gln Leu Ser Gln Glu Leu Glu Ser
            450                 455                 460
Leu Lys Val Arg Ile Lys Glu Leu Glu Ala Ile Glu Ser Arg Leu Glu
465                 470                 475                 480
Lys Thr Glu Phe Thr Leu Lys Glu Asp Leu Thr Lys Leu Lys Thr Leu
                485                 490                 495
Thr Val Met Phe Val Asp Glu Arg Lys Thr Met Ser Glu Lys Leu Lys
            500                 505                 510
Lys Thr Glu Asp Lys Leu Gln Ala Ala Ser Ser Gln Leu Gln Val Glu
            515                 520                 525
Gln Asn Lys Val Thr Thr Val Thr Glu Lys Leu Ile Glu Glu Thr Lys
            530                 535                 540
Arg Ala Leu Lys Ser Lys Thr Asp Val Glu Glu Lys Met Tyr Ser Val
545                 550                 555                 560
Thr Lys Glu Arg Asp Asp Leu Lys Asn Lys Leu Lys Ala Glu Glu Glu
                565                 570                 575
Lys Gly Asn Asp Leu Leu Ser Arg Val Asn Met Leu Lys Asn Arg Leu
            580                 585                 590
Gln Ser Leu Glu Ala Ile Glu Lys Asp Phe Leu Lys Asn Lys Leu Asn
            595                 600                 605
Gln Asp Ser Gly Lys Ser Thr Thr Ala Leu His Gln Glu Asn Asn Lys
            610                 615                 620
Ile Lys Glu Leu Ser Gln Glu Val Glu Arg Leu Lys Leu Lys Leu Lys
625                 630                 635                 640
Asp Met Lys Ala Ile Glu Asp Asp Leu Met Lys Thr Glu Asp Glu Tyr
                645                 650                 655
```

```
Glu Thr Leu Glu Arg Arg Tyr Ala Asn Glu Arg Asp Lys Ala Gln Phe
            660                 665                 670

Leu Ser Lys Glu Leu Glu His Val Lys Met Glu Leu Ala Lys Tyr Lys
        675                 680                 685

Leu Ala Glu Lys Thr Glu Thr Ser His Glu Gln Trp Leu Phe Lys Arg
        690                 695                 700

Leu Gln Glu Glu Ala Lys Ser Gly His Leu Ser Arg Glu Val Asp
705                 710                 715                 720

Ala Leu Lys Glu Lys Ile His Glu Tyr Met Ala Thr Glu Asp Leu Ile
                725                 730                 735

Cys His Leu Gln Gly Asp His Ser Val Leu Gln Lys Lys Leu Asn Gln
            740                 745                 750

Gln Glu Asn Arg Asn Arg Asp Leu Gly Arg Glu Ile Glu Asn Leu Thr
            755                 760                 765

Lys Glu Leu Glu Arg Tyr Arg His Phe Ser Lys Ser Leu Arg Pro Ser
        770                 775                 780

Leu Asn Gly Arg Arg Ile Ser Asp Pro Gln Val Phe Ser Lys Glu Val
785                 790                 795                 800

Gln Thr Glu Ala Val Asp Asn Glu Pro Pro Asp Tyr Lys Ser Leu Ile
                805                 810                 815

Pro Leu Glu Arg Ala Val Ile Asn Gly Gln Leu Tyr Glu Glu Ser Glu
            820                 825                 830

Asn Gln Asp Glu Asp Pro Asn Asp Glu Gly Ser Val Leu Ser Phe Lys
            835                 840                 845

Cys Ser Gln Ser Thr Pro Cys Pro Val Asn Arg Lys Leu Trp Ile Pro
850                 855                 860

Trp Met Lys Ser Lys Glu Gly His Leu Gln Asn Gly Lys Met Gln Thr
865                 870                 875                 880

Lys Pro Asn Ala Asn Phe Val Gln Pro Gly Asp Leu Val Leu Ser His
                885                 890                 895

Thr Pro Gly Gln Pro Leu His Ile Lys Val Thr Pro Asp His Val Gln
            900                 905                 910

Asn Thr Ala Thr Leu Glu Ile Thr Ser Pro Thr Thr Glu Ser Pro His
        915                 920                 925

Ser Tyr Thr Ser Thr Ala Val Ile Pro Asn Cys Gly Thr Pro Lys Gln
        930                 935                 940

Arg Ile Thr Ile Leu Gln Asn Ala Ser Ile Thr Pro Val Lys Ser Lys
945                 950                 955                 960

Thr Ser Thr Glu Asp Leu Met Asn Leu Glu Gln Gly Met Ser Pro Ile
                965                 970                 975

Thr Met Ala Thr Phe Ala Arg Ala Gln Thr Pro Glu Ser Cys Gly Ser
            980                 985                 990

Leu Thr Pro Glu Arg Thr Met Ser  Pro Ile Gln Val Leu  Ala Val Thr
            995                 1000                1005

Gly Ser  Ala Ser Ser Pro Glu  Gln Gly Arg Ser Pro  Glu Pro Thr
     1010                 1015                1020

Glu Ile  Ser Ala Lys His Ala  Ile Phe Arg Val Ser  Pro Asp Arg
     1025                 1030                1035

Gln Ser  Ser Trp Gln Phe Gln  Arg Ser Asn Ser Asn  Ser Ser Ser
     1040                 1045                1050

Val Ile  Thr Thr Glu Asp Asn  Lys Ile His Ile His  Leu Gly Ser
     1055                 1060                1065
```

-continued

```
Pro Tyr Met Gln Ala Val Ala Ser Pro Val Arg Pro Ala Ser Pro
    1070            1075                1080
Ser Ala Pro Leu Gln Asp Asn Arg Thr Gln Gly Leu Ile Asn Gly
    1085            1090                1095
Ala Leu Asn Lys Thr Thr Asn Lys Val Thr Ser Ser Ile Thr Ile
    1100            1105                1110
Thr Pro Thr Ala Thr Pro Leu Pro Arg Gln Ser Gln Ile Thr Val
    1115            1120                1125
Ser Asn Ile Tyr Asn
    1130

<210> SEQ ID NO 17
<211> LENGTH: 45
<212> TYPE: DNA
<213> ORGANISM: Homo sapiens
<220> FEATURE:
<221> NAME/KEY: CDS
<222> LOCATION: (1)..(45)
<223> OTHER INFORMATION:

<400> SEQUENCE: 17 act aaa tca aca aga aaa cag gaa cag aga ttt agg aag aga gat      45
Thr Lys Ser Thr Arg Lys Gln Glu Gln Arg Phe Arg Lys Arg Asp
1               5                   10                  15

<210> SEQ ID NO 18
<211> LENGTH: 15
<212> TYPE: PRT
<213> ORGANISM: Homo sapiens

<400> SEQUENCE: 18

Thr Lys Ser Thr Arg Lys Gln Glu Gln Arg Phe Arg Lys Arg Asp
1               5                   10                  15

<210> SEQ ID NO 19
<211> LENGTH: 90
<212> TYPE: DNA
<213> ORGANISM: Homo sapiens
<220> FEATURE:
<221> NAME/KEY: CDS
<222> LOCATION: (1)..(90)
<223> OTHER INFORMATION:

<400> SEQUENCE: 19 gtg gat gaa cag caa agg ctg acg gca cag ctc acc ctt caa aga cag      48
Val Asp Glu Gln Gln Arg Leu Thr Ala Gln Leu Thr Leu Gln Arg Gln
1               5                   10                  15 aaa atc caa gag ctg acc aca aat gca aag gaa aca cat acc              90
Lys Ile Gln Glu Leu Thr Thr Asn Ala Lys Glu Thr His Thr
                20                  25                  30

<210> SEQ ID NO 20
<211> LENGTH: 30
<212> TYPE: PRT
<213> ORGANISM: Homo sapiens

<400> SEQUENCE: 20

Val Asp Glu Gln Gln Arg Leu Thr Ala Gln Leu Thr Leu Gln Arg Gln
1               5                   10                  15

Lys Ile Gln Glu Leu Thr Thr Asn Ala Lys Glu Thr His Thr
                20                  25                  30

<210> SEQ ID NO 21
<211> LENGTH: 1158
```

```
<212> TYPE: DNA
<213> ORGANISM: Homo sapiens
<220> FEATURE:
<221> NAME/KEY: CDS
<222> LOCATION: (1)..(1158)
<223> OTHER INFORMATION:

<400> SEQUENCE: 21 cta aat caa caa gaa aac agg aac aga gat tta gga aga gag att gaa      48
Leu Asn Gln Gln Glu Asn Arg Asn Arg Asp Leu Gly Arg Glu Ile Glu
1               5                   10                  15 aac ctc act aag gag tta gag agg tac cgg cat ttc agt aag agc ctc      96
Asn Leu Thr Lys Glu Leu Glu Arg Tyr Arg His Phe Ser Lys Ser Leu
            20                  25                  30 agg cct agt ctc aat gga aga aga att tcc gat cct caa gta ttt tct     144
Arg Pro Ser Leu Asn Gly Arg Arg Ile Ser Asp Pro Gln Val Phe Ser
        35                  40                  45 aaa gaa gtt cag aca gaa gca gta gac aat gaa cca cct gat tac aag     192
Lys Glu Val Gln Thr Glu Ala Val Asp Asn Glu Pro Pro Asp Tyr Lys
    50                  55                  60 agc ctc att cct ctg gaa cgt gca gtc atc aat ggt cag tta tat gag     240
Ser Leu Ile Pro Leu Glu Arg Ala Val Ile Asn Gly Gln Leu Tyr Glu
65                  70                  75                  80 gag agt gag aat caa gac gag gac cct aat gat gag gga tct gtg ctg     288
Glu Ser Glu Asn Gln Asp Glu Asp Pro Asn Asp Glu Gly Ser Val Leu
                85                  90                  95 tcc ttc aaa tgc agc cag tct act cca tgt cct gtt aac aga aag cta     336
Ser Phe Lys Cys Ser Gln Ser Thr Pro Cys Pro Val Asn Arg Lys Leu
            100                 105                 110 tgg att ccc tgg atg aaa tcc aag gag ggc cat ctt cag aat gga aaa     384
Trp Ile Pro Trp Met Lys Ser Lys Glu Gly His Leu Gln Asn Gly Lys
        115                 120                 125 atg caa act aaa ccc aat gcc aac ttt gtg caa cct gga gat cta gtc     432
Met Gln Thr Lys Pro Asn Ala Asn Phe Val Gln Pro Gly Asp Leu Val
    130                 135                 140 cta agc cac aca cct ggg cag cca ctt cat ata aag gtt act cca gac     480
Leu Ser His Thr Pro Gly Gln Pro Leu His Ile Lys Val Thr Pro Asp
145                 150                 155                 160 cat gta caa aac aca gcc act ctt gaa atc aca agt cca acc aca gag     528
His Val Gln Asn Thr Ala Thr Leu Glu Ile Thr Ser Pro Thr Thr Glu
                165                 170                 175 agt cct cac tct tac acg agt act gca gtg ata ccg aac tgt ggc acg     576
Ser Pro His Ser Tyr Thr Ser Thr Ala Val Ile Pro Asn Cys Gly Thr
            180                 185                 190 cca aag caa agg ata acc atc ctc caa aac gcc tcc ata aca cca gta     624
Pro Lys Gln Arg Ile Thr Ile Leu Gln Asn Ala Ser Ile Thr Pro Val
        195                 200                 205 aag tcc aaa acc tct acc gaa gac ctc atg aat tta gaa caa ggc atg     672
Lys Ser Lys Thr Ser Thr Glu Asp Leu Met Asn Leu Glu Gln Gly Met
    210                 215                 220 tcc cca att acc atg gca acc ttt gcc aga gca cag acc cca gag tct     720
Ser Pro Ile Thr Met Ala Thr Phe Ala Arg Ala Gln Thr Pro Glu Ser
225                 230                 235                 240 tgt ggt tct cta act cca gaa agg aca atg tcc cct att cag gtt ttg     768
Cys Gly Ser Leu Thr Pro Glu Arg Thr Met Ser Pro Ile Gln Val Leu
                245                 250                 255 gct gtg act ggt tca gct agc tct cct gag cag gga cgc tcc cca gaa     816
Ala Val Thr Gly Ser Ala Ser Ser Pro Glu Gln Gly Arg Ser Pro Glu
            260                 265                 270 cca aca gaa atc agt gcc aag cat gcg ata ttc aga gtc tcc cca gac     864
Pro Thr Glu Ile Ser Ala Lys His Ala Ile Phe Arg Val Ser Pro Asp
```

```
                    275                 280                 285
cgg cag tca tca tgg cag ttt cag cgt tca aac agc aat agc tca agt   912
Arg Gln Ser Ser Trp Gln Phe Gln Arg Ser Asn Ser Asn Ser Ser Ser
    290                 295                 300 gtg ata act act gag gat aat aaa atc cac att cac tta gga agt cct   960
Val Ile Thr Thr Glu Asp Asn Lys Ile His Ile His Leu Gly Ser Pro
305                 310                 315                 320 tac atg caa gct gta gcc agc cct gtg aga cct gcc agc cct tca gca  1008
Tyr Met Gln Ala Val Ala Ser Pro Val Arg Pro Ala Ser Pro Ser Ala
                325                 330                 335 cca ctg cag gat aac cga act caa ggc tta att aac ggg gca cta aac  1056
Pro Leu Gln Asp Asn Arg Thr Gln Gly Leu Ile Asn Gly Ala Leu Asn
            340                 345                 350 aaa aca acc aat aaa gtc acc agc agt att act atc aca cca aca gcc  1104
Lys Thr Thr Asn Lys Val Thr Ser Ser Ile Thr Ile Thr Pro Thr Ala
        355                 360                 365 aca cct ctt cct cga caa tca caa att aca gtg gaa cca ctt ctt ctg  1152
Thr Pro Leu Pro Arg Gln Ser Gln Ile Thr Val Glu Pro Leu Leu Leu
    370                 375                 380 cct cat                                                           1158
Pro His
385

<210> SEQ ID NO 22
<211> LENGTH: 386
<212> TYPE: PRT
<213> ORGANISM: Homo sapiens

<400> SEQUENCE: 22

Leu Asn Gln Gln Glu Asn Arg Asn Arg Asp Leu Gly Arg Glu Ile Glu
1               5                   10                  15

Asn Leu Thr Lys Glu Leu Glu Arg Tyr Arg His Phe Ser Lys Ser Leu
            20                  25                  30

Arg Pro Ser Leu Asn Gly Arg Arg Ile Ser Asp Pro Gln Val Phe Ser
        35                  40                  45

Lys Glu Val Gln Thr Glu Ala Val Asp Asn Glu Pro Pro Asp Tyr Lys
    50                  55                  60

Ser Leu Ile Pro Leu Glu Arg Ala Val Ile Asn Gly Gln Leu Tyr Glu
65                  70                  75                  80

Glu Ser Glu Asn Gln Asp Glu Asp Pro Asn Asp Glu Gly Ser Val Leu
                85                  90                  95

Ser Phe Lys Cys Ser Gln Ser Thr Pro Cys Pro Val Asn Arg Lys Leu
            100                 105                 110

Trp Ile Pro Trp Met Lys Ser Lys Glu Gly His Leu Gln Asn Gly Lys
        115                 120                 125

Met Gln Thr Lys Pro Asn Ala Asn Phe Val Gln Pro Gly Asp Leu Val
    130                 135                 140

Leu Ser His Thr Pro Gly Gln Pro Leu His Ile Lys Val Thr Pro Asp
145                 150                 155                 160

His Val Gln Asn Thr Ala Thr Leu Glu Ile Thr Ser Pro Thr Thr Glu
                165                 170                 175

Ser Pro His Ser Tyr Thr Ser Thr Ala Val Ile Pro Asn Cys Gly Thr
            180                 185                 190

Pro Lys Gln Arg Ile Thr Ile Leu Gln Asn Ala Ser Ile Thr Pro Val
        195                 200                 205

Lys Ser Lys Thr Ser Thr Glu Asp Leu Met Asn Leu Glu Gln Gly Met
    210                 215                 220
```

```
Ser Pro Ile Thr Met Ala Thr Phe Ala Arg Ala Gln Thr Pro Glu Ser
225                 230                 235                 240

Cys Gly Ser Leu Thr Pro Glu Arg Thr Met Ser Pro Ile Gln Val Leu
            245                 250                 255

Ala Val Thr Gly Ser Ala Ser Ser Pro Glu Gln Gly Arg Ser Pro Glu
        260                 265                 270

Pro Thr Glu Ile Ser Ala Lys His Ala Ile Phe Arg Val Ser Pro Asp
    275                 280                 285

Arg Gln Ser Ser Trp Gln Phe Gln Arg Ser Asn Ser Asn Ser Ser Ser
290                 295                 300

Val Ile Thr Thr Glu Asp Asn Lys Ile His Ile His Leu Gly Ser Pro
305                 310                 315                 320

Tyr Met Gln Ala Val Ala Ser Pro Val Arg Pro Ala Ser Pro Ser Ala
                325                 330                 335

Pro Leu Gln Asp Asn Arg Thr Gln Gly Leu Ile Asn Gly Ala Leu Asn
            340                 345                 350

Lys Thr Thr Asn Lys Val Thr Ser Ser Ile Thr Ile Thr Pro Thr Ala
            355                 360                 365

Thr Pro Leu Pro Arg Gln Ser Gln Ile Thr Val Glu Pro Leu Leu Leu
    370                 375                 380

Pro His
385

<210> SEQ ID NO 23
<211> LENGTH: 2355
<212> TYPE: DNA
<213> ORGANISM: Homo sapiens
<220> FEATURE:
<221> NAME/KEY: CDS
<222> LOCATION: (1)..(2355)
<223> OTHER INFORMATION:

<400> SEQUENCE: 23 ctg caa gat ata aaa gaa aaa atc agt aag gga gaa tat gga aac gct      48
Leu Gln Asp Ile Lys Glu Lys Ile Ser Lys Gly Glu Tyr Gly Asn Ala
1               5                   10                  15 ggt atc atg gct gaa gtg gaa gag ctc agg aaa cgt gtg cta gat atg      96
Gly Ile Met Ala Glu Val Glu Glu Leu Arg Lys Arg Val Leu Asp Met
            20                  25                  30 gaa ggg aaa gat gaa gag ctc ata aaa atg gag gag cag tgc aga gat     144
Glu Gly Lys Asp Glu Glu Leu Ile Lys Met Glu Glu Gln Cys Arg Asp
        35                  40                  45 ctc aat aag agg ctt gaa agg gag acg tta cag agt aaa gac ttt aaa     192
Leu Asn Lys Arg Leu Glu Arg Glu Thr Leu Gln Ser Lys Asp Phe Lys
    50                  55                  60 cta gag gtt gaa aaa ctc agt aaa aga att atg gct ctg gaa aag tta     240
Leu Glu Val Glu Lys Leu Ser Lys Arg Ile Met Ala Leu Glu Lys Leu
65                  70                  75                  80 gaa gac gct ttc aac aaa agc aaa caa gaa tgc tac tct ctg aaa tgc     288
Glu Asp Ala Phe Asn Lys Ser Lys Gln Glu Cys Tyr Ser Leu Lys Cys
                85                  90                  95 aat tta gaa aaa gaa agg atg acc aca aag cag ttg tct caa gaa ctg     336
Asn Leu Glu Lys Glu Arg Met Thr Thr Lys Gln Leu Ser Gln Glu Leu
            100                 105                 110 gag agt tta aaa gta agg atc aaa gag cta gaa gcc att gaa agt cgg     384
Glu Ser Leu Lys Val Arg Ile Lys Glu Leu Glu Ala Ile Glu Ser Arg
        115                 120                 125 cta gaa aag aca gaa ttc act cta aaa gag gat tta act aaa ctg aaa     432
```

```
                    Leu Glu Lys Thr Glu Phe Thr Leu Lys Glu Asp Leu Thr Lys Leu Lys
                        130                 135                 140 aca tta act gtg atg ttt gta gat gaa cgg aaa aca atg agt gaa aaa        480
Thr Leu Thr Val Met Phe Val Asp Glu Arg Lys Thr Met Ser Glu Lys
145                 150                 155                 160 tta aag aaa act gaa gat aaa tta caa gct gct tct tct cag ctt caa        528
Leu Lys Lys Thr Glu Asp Lys Leu Gln Ala Ala Ser Ser Gln Leu Gln
                    165                 170                 175 gtg gag caa aat aaa gta aca aca gtt act gag aag tta att gag gaa        576
Val Glu Gln Asn Lys Val Thr Thr Val Thr Glu Lys Leu Ile Glu Glu
                180                 185                 190 act aaa agg gcg ctc aag tcc aaa acc gat gta gaa gaa aag atg tac        624
Thr Lys Arg Ala Leu Lys Ser Lys Thr Asp Val Glu Glu Lys Met Tyr
            195                 200                 205 agc gta acc aag gag aga gat gat tta aaa aac aaa ttg aaa gcg gaa        672
Ser Val Thr Lys Glu Arg Asp Asp Leu Lys Asn Lys Leu Lys Ala Glu
        210                 215                 220 gaa gag aaa gga aat gat ctc ctg tca aga gtt aat atg ttg aaa aat        720
Glu Glu Lys Gly Asn Asp Leu Leu Ser Arg Val Asn Met Leu Lys Asn
225                 230                 235                 240 agg ctt caa tca ttg gaa gca att gag aaa gat ttc cta aaa aac aaa        768
Arg Leu Gln Ser Leu Glu Ala Ile Glu Lys Asp Phe Leu Lys Asn Lys
                    245                 250                 255 tta aat caa gac tct ggg aaa tcc aca aca gca tta cac caa gaa aac        816
Leu Asn Gln Asp Ser Gly Lys Ser Thr Thr Ala Leu His Gln Glu Asn
                260                 265                 270 aat aag att aag gag ctc tct caa gaa gtg gaa aga ctg aaa ctg aag        864
Asn Lys Ile Lys Glu Leu Ser Gln Glu Val Glu Arg Leu Lys Leu Lys
            275                 280                 285 cta aag gac atg aaa gcc att gag gat gac ctc atg aaa aca gaa gat        912
Leu Lys Asp Met Lys Ala Ile Glu Asp Asp Leu Met Lys Thr Glu Asp
        290                 295                 300 gaa tat gag act cta gaa cga agg tat gct aat gaa cga gac aaa gct        960
Glu Tyr Glu Thr Leu Glu Arg Arg Tyr Ala Asn Glu Arg Asp Lys Ala
305                 310                 315                 320 caa ttt tta tct aaa gag cta gaa cat gtt aaa atg gaa ctt gct aag       1008
Gln Phe Leu Ser Lys Glu Leu Glu His Val Lys Met Glu Leu Ala Lys
                    325                 330                 335 tac aag tta gca gaa aag aca gag acc agc cat gaa caa tgg ctt ttc       1056
Tyr Lys Leu Ala Glu Lys Thr Glu Thr Ser His Glu Gln Trp Leu Phe
                340                 345                 350 aaa agg ctt caa gaa gaa gaa gct aag tca ggg cac ctc tca aga gaa       1104
Lys Arg Leu Gln Glu Glu Glu Ala Lys Ser Gly His Leu Ser Arg Glu
            355                 360                 365 gtg gat gca tta aaa gag aaa att cat gaa tac atg gca act gaa gac       1152
Val Asp Ala Leu Lys Glu Lys Ile His Glu Tyr Met Ala Thr Glu Asp
        370                 375                 380 cta ata tgt cac ctc cag gga gat cac tca gtc ctg caa aaa aaa cta       1200
Leu Ile Cys His Leu Gln Gly Asp His Ser Val Leu Gln Lys Lys Leu
385                 390                 395                 400 aat caa caa gaa aac agg aac aga gat tta gga aga gag att gaa aac       1248
Asn Gln Gln Glu Asn Arg Asn Arg Asp Leu Gly Arg Glu Ile Glu Asn
                    405                 410                 415 ctc act aag gag tta gag agg tac cgg cat ttc agt aag agc ctc agg       1296
Leu Thr Lys Glu Leu Glu Arg Tyr Arg His Phe Ser Lys Ser Leu Arg
                420                 425                 430 cct agt ctc aat gga aga aga att tcc gat cct caa gta ttt tct aaa       1344
Pro Ser Leu Asn Gly Arg Arg Ile Ser Asp Pro Gln Val Phe Ser Lys
            435                 440                 445
```

```
                                                      -continued gaa gtt cag aca gaa gca gta gac aat gaa cca cct gat tac aag agc    1392
Glu Val Gln Thr Glu Ala Val Asp Asn Glu Pro Pro Asp Tyr Lys Ser
    450                 455                 460 ctc att cct ctg gaa cgt gca gtc atc aat ggt cag tta tat gag gag    1440
Leu Ile Pro Leu Glu Arg Ala Val Ile Asn Gly Gln Leu Tyr Glu Glu
465                 470                 475                 480 agt gag aat caa gac gag gac cct aat gat gag gga tct gtg ctg tcc    1488
Ser Glu Asn Gln Asp Glu Asp Pro Asn Asp Glu Gly Ser Val Leu Ser
                485                 490                 495 ttc aaa tgc agc cag tct act cca tgt cct gtt aac aga aag cta tgg    1536
Phe Lys Cys Ser Gln Ser Thr Pro Cys Pro Val Asn Arg Lys Leu Trp
            500                 505                 510 att ccc tgg atg aaa tcc aag gag ggc cat ctt cag aat gga aaa atg    1584
Ile Pro Trp Met Lys Ser Lys Glu Gly His Leu Gln Asn Gly Lys Met
        515                 520                 525 caa act aaa ccc aat gcc aac ttt gtg caa cct gga gat cta gtc cta    1632
Gln Thr Lys Pro Asn Ala Asn Phe Val Gln Pro Gly Asp Leu Val Leu
530                 535                 540 agc cac aca cct ggg cag cca ctt cat ata aag gtt act cca gac cat    1680
Ser His Thr Pro Gly Gln Pro Leu His Ile Lys Val Thr Pro Asp His
545                 550                 555                 560 gta caa aac aca gcc act ctt gaa atc aca agt cca acc aca gag agt    1728
Val Gln Asn Thr Ala Thr Leu Glu Ile Thr Ser Pro Thr Thr Glu Ser
                565                 570                 575 cct cac tct tac acg agt act gca gtg ata ccg aac tgt ggc acg cca    1776
Pro His Ser Tyr Thr Ser Thr Ala Val Ile Pro Asn Cys Gly Thr Pro
            580                 585                 590 aag caa agg ata acc atc ctc caa aac gcc tcc ata aca cca gta aag    1824
Lys Gln Arg Ile Thr Ile Leu Gln Asn Ala Ser Ile Thr Pro Val Lys
        595                 600                 605 tcc aaa acc tct acc gaa gac ctc atg aat tta gaa caa ggc atg tcc    1872
Ser Lys Thr Ser Thr Glu Asp Leu Met Asn Leu Glu Gln Gly Met Ser
610                 615                 620 cca att acc atg gca acc ttt gcc aga gca cag acc cca gag tct tgt    1920
Pro Ile Thr Met Ala Thr Phe Ala Arg Ala Gln Thr Pro Glu Ser Cys
625                 630                 635                 640 ggt tct cta act cca gaa agg aca atg tcc cct att cag gtt ttg gct    1968
Gly Ser Leu Thr Pro Glu Arg Thr Met Ser Pro Ile Gln Val Leu Ala
                645                 650                 655 gtg act ggt tca gct agc tct cct gag cag gga cgc tcc cca gaa cca    2016
Val Thr Gly Ser Ala Ser Ser Pro Glu Gln Gly Arg Ser Pro Glu Pro
            660                 665                 670 aca gaa atc agt gcc aag cat gcg ata ttc aga gtc tcc cca gac cgg    2064
Thr Glu Ile Ser Ala Lys His Ala Ile Phe Arg Val Ser Pro Asp Arg
        675                 680                 685 cag tca tca tgg cag ttt cag cgt tca aac agc aat agc tca agt gtg    2112
Gln Ser Ser Trp Gln Phe Gln Arg Ser Asn Ser Asn Ser Ser Ser Val
690                 695                 700 ata act act gag gat aat aaa atc cac att cac tta gga agt cct tac    2160
Ile Thr Thr Glu Asp Asn Lys Ile His Ile His Leu Gly Ser Pro Tyr
705                 710                 715                 720 atg caa gct gta gcc agc cct gtg aga cct gcc agc cct tca gca cca    2208
Met Gln Ala Val Ala Ser Pro Val Arg Pro Ala Ser Pro Ser Ala Pro
                725                 730                 735 ctg cag gat aac cga act caa ggc tta att aac ggg gca cta aac aaa    2256
Leu Gln Asp Asn Arg Thr Gln Gly Leu Ile Asn Gly Ala Leu Asn Lys
            740                 745                 750 aca acc aat aaa gtc acc agc agt att act atc aca cca aca gcc aca    2304
Thr Thr Asn Lys Val Thr Ser Ser Ile Thr Ile Thr Pro Thr Ala Thr
        755                 760                 765
```

```
cct ctt cct cga caa tca caa att aca gtg gaa cca ctt ctt ctg cct    2352
Pro Leu Pro Arg Gln Ser Gln Ile Thr Val Glu Pro Leu Leu Leu Pro
    770             775                 780 cat                                                                 2355
His
785
```

<210> SEQ ID NO 24
<211> LENGTH: 785
<212> TYPE: PRT
<213> ORGANISM: Homo sapiens

<400> SEQUENCE: 24

```
Leu Gln Asp Ile Lys Glu Lys Ile Ser Lys Gly Glu Tyr Gly Asn Ala
1               5                   10                  15

Gly Ile Met Ala Glu Val Glu Leu Arg Lys Arg Val Leu Asp Met
            20                  25                  30

Glu Gly Lys Asp Glu Leu Ile Lys Met Glu Gln Cys Arg Asp
                35                  40                  45

Leu Asn Lys Arg Leu Glu Arg Glu Thr Leu Gln Ser Lys Asp Phe Lys
50                  55                  60

Leu Glu Val Glu Lys Leu Ser Lys Arg Ile Met Ala Leu Glu Lys Leu
65                  70                  75                  80

Glu Asp Ala Phe Asn Lys Ser Lys Gln Glu Cys Tyr Ser Leu Lys Cys
                85                  90                  95

Asn Leu Glu Lys Glu Arg Met Thr Thr Lys Gln Leu Ser Gln Glu Leu
                100                 105                 110

Glu Ser Leu Lys Val Arg Ile Lys Glu Leu Glu Ala Ile Glu Ser Arg
            115                 120                 125

Leu Glu Lys Thr Glu Phe Thr Leu Lys Glu Asp Leu Thr Lys Leu Lys
130                 135                 140

Thr Leu Thr Val Met Phe Val Asp Glu Arg Lys Thr Met Ser Glu Lys
145                 150                 155                 160

Leu Lys Lys Thr Glu Asp Lys Leu Gln Ala Ala Ser Ser Gln Leu Gln
                165                 170                 175

Val Glu Gln Asn Lys Val Thr Thr Val Thr Glu Lys Leu Ile Glu Glu
            180                 185                 190

Thr Lys Arg Ala Leu Lys Ser Lys Thr Asp Val Glu Glu Lys Met Tyr
        195                 200                 205

Ser Val Thr Lys Glu Arg Asp Asp Leu Lys Asn Lys Lys Ala Glu
    210                 215                 220

Glu Glu Lys Gly Asn Asp Leu Leu Ser Arg Val Asn Met Leu Lys Asn
225                 230                 235                 240

Arg Leu Gln Ser Leu Glu Ala Ile Glu Lys Asp Phe Leu Lys Asn Lys
                245                 250                 255

Leu Asn Gln Asp Ser Gly Lys Ser Thr Thr Ala Leu His Gln Glu Asn
                260                 265                 270

Asn Lys Ile Lys Glu Leu Ser Gln Glu Val Glu Arg Leu Lys Leu Lys
            275                 280                 285

Leu Lys Asp Met Lys Ala Ile Glu Asp Asp Leu Met Lys Thr Glu Asp
        290                 295                 300

Glu Tyr Glu Thr Leu Glu Arg Arg Tyr Ala Asn Glu Arg Asp Lys Ala
305                 310                 315                 320

Gln Phe Leu Ser Lys Glu Leu Glu His Val Lys Met Glu Leu Ala Lys
                325                 330                 335
```

```
Tyr Lys Leu Ala Glu Lys Thr Glu Thr Ser His Glu Gln Trp Leu Phe
            340                 345                 350

Lys Arg Leu Gln Glu Glu Ala Lys Ser Gly His Leu Ser Arg Glu
        355                 360                 365

Val Asp Ala Leu Lys Glu Lys Ile His Glu Tyr Met Ala Thr Glu Asp
    370                 375                 380

Leu Ile Cys His Leu Gln Gly Asp His Ser Val Leu Gln Lys Lys Leu
385                 390                 395                 400

Asn Gln Gln Glu Asn Arg Asn Arg Asp Leu Gly Arg Glu Ile Glu Asn
                405                 410                 415

Leu Thr Lys Glu Leu Glu Arg Tyr Arg His Phe Ser Lys Ser Leu Arg
            420                 425                 430

Pro Ser Leu Asn Gly Arg Arg Ile Ser Asp Pro Gln Val Phe Ser Lys
        435                 440                 445

Glu Val Gln Thr Glu Ala Val Asp Asn Glu Pro Pro Asp Tyr Lys Ser
    450                 455                 460

Leu Ile Pro Leu Glu Arg Ala Val Ile Asn Gly Gln Leu Tyr Glu Glu
465                 470                 475                 480

Ser Glu Asn Gln Asp Glu Asp Pro Asn Asp Glu Gly Ser Val Leu Ser
                485                 490                 495

Phe Lys Cys Ser Gln Ser Thr Pro Cys Pro Val Asn Arg Lys Leu Trp
            500                 505                 510

Ile Pro Trp Met Lys Ser Lys Glu Gly His Leu Gln Asn Gly Lys Met
        515                 520                 525

Gln Thr Lys Pro Asn Ala Asn Phe Val Gln Pro Gly Asp Leu Val Leu
    530                 535                 540

Ser His Thr Pro Gly Gln Pro Leu His Ile Lys Val Thr Pro Asp His
545                 550                 555                 560

Val Gln Asn Thr Ala Thr Leu Glu Ile Thr Ser Pro Thr Thr Glu Ser
                565                 570                 575

Pro His Ser Tyr Thr Ser Thr Ala Val Ile Pro Asn Cys Gly Thr Pro
            580                 585                 590

Lys Gln Arg Ile Thr Ile Leu Gln Asn Ala Ser Ile Thr Pro Val Lys
        595                 600                 605

Ser Lys Thr Ser Thr Glu Asp Leu Met Asn Leu Glu Gln Gly Met Ser
    610                 615                 620

Pro Ile Thr Met Ala Thr Phe Ala Arg Ala Gln Thr Pro Glu Ser Cys
625                 630                 635                 640

Gly Ser Leu Thr Pro Glu Arg Thr Met Ser Pro Ile Gln Val Leu Ala
                645                 650                 655

Val Thr Gly Ser Ala Ser Ser Pro Glu Gln Gly Arg Ser Pro Glu Pro
            660                 665                 670

Thr Glu Ile Ser Ala Lys His Ala Ile Phe Arg Val Ser Pro Asp Arg
        675                 680                 685

Gln Ser Ser Trp Gln Phe Gln Arg Ser Asn Ser Asn Ser Ser Ser Val
    690                 695                 700

Ile Thr Thr Glu Asp Asn Lys Ile His Ile His Leu Gly Ser Pro Tyr
705                 710                 715                 720

Met Gln Ala Val Ala Ser Pro Val Arg Pro Ala Ser Pro Ser Ala Pro
                725                 730                 735

Leu Gln Asp Asn Arg Thr Gln Gly Leu Ile Asn Gly Ala Leu Asn Lys
            740                 745                 750
```

-continued

```
Thr Thr Asn Lys Val Thr Ser Ser Ile Thr Ile Thr Pro Thr Ala Thr
        755                 760                 765
Pro Leu Pro Arg Gln Ser Gln Ile Thr Val Glu Pro Leu Leu Leu Pro
        770                 775                 780
His
785

<210> SEQ ID NO 25
<211> LENGTH: 21
<212> TYPE: DNA
<213> ORGANISM: Homo sapiens
<220> FEATURE:
<221> NAME/KEY: CDS
<222> LOCATION: (1)..(21)
<223> OTHER INFORMATION:

<400> SEQUENCE: 25 gaa cca ctt ctt ctg cct cat                                         21
Glu Pro Leu Leu Leu Pro His
1               5

<210> SEQ ID NO 26
<211> LENGTH: 7
<212> TYPE: PRT
<213> ORGANISM: Homo sapiens

<400> SEQUENCE: 26

Glu Pro Leu Leu Leu Pro His
1               5

<210> SEQ ID NO 27
<211> LENGTH: 30
<212> TYPE: DNA
<213> ORGANISM: Homo sapiens
<220> FEATURE:
<221> NAME/KEY: CDS
<222> LOCATION: (1)..(30)
<223> OTHER INFORMATION:

<400> SEQUENCE: 27 ttg gac aaa gtt gtg gaa aaa cat aaa gaa                             30
Leu Asp Lys Val Val Glu Lys His Lys Glu
1               5                   10

<210> SEQ ID NO 28
<211> LENGTH: 10
<212> TYPE: PRT
<213> ORGANISM: Homo sapiens

<400> SEQUENCE: 28

Leu Asp Lys Val Val Glu Lys His Lys Glu
1               5                   10

<210> SEQ ID NO 29
<211> LENGTH: 30
<212> TYPE: DNA
<213> ORGANISM: Homo sapiens
<220> FEATURE:
<221> NAME/KEY: CDS
<222> LOCATION: (1)..(30)
<223> OTHER INFORMATION:

<400> SEQUENCE: 29 gag gaa gag cag aag gca acc aga cta gag                             30
Glu Glu Glu Gln Lys Ala Thr Arg Leu Glu
1               5                   10
```

```
<210> SEQ ID NO 30
<211> LENGTH: 10
<212> TYPE: PRT
<213> ORGANISM: Homo sapiens

<400> SEQUENCE: 30

Glu Glu Glu Gln Lys Ala Thr Arg Leu Glu
1               5                   10

<210> SEQ ID NO 31
<211> LENGTH: 60
<212> TYPE: DNA
<213> ORGANISM: Homo sapiens
<220> FEATURE:
<221> NAME/KEY: CDS
<222> LOCATION: (1)..(60)
<223> OTHER INFORMATION:

<400> SEQUENCE: 31 ttg gac aaa gtt gtg gaa aaa cat aaa gaa tct tac aga cga atc ctg        48
Leu Asp Lys Val Val Glu Lys His Lys Glu Ser Tyr Arg Arg Ile Leu
1               5                   10                  15 gga cag ctt tta                                                        60
Gly Gln Leu Leu
            20

<210> SEQ ID NO 32
<211> LENGTH: 20
<212> TYPE: PRT
<213> ORGANISM: Homo sapiens

<400> SEQUENCE: 32

Leu Asp Lys Val Val Glu Lys His Lys Glu Ser Tyr Arg Arg Ile Leu
1               5                   10                  15

Gly Gln Leu Leu
            20

<210> SEQ ID NO 33
<211> LENGTH: 150
<212> TYPE: DNA
<213> ORGANISM: Homo sapiens
<220> FEATURE:
<221> NAME/KEY: CDS
<222> LOCATION: (1)..(150)
<223> OTHER INFORMATION:

<400> SEQUENCE: 33 gtg gat gaa cag caa agg ctg acg gca cag ctc acc ctt caa aga cag        48
Val Asp Glu Gln Gln Arg Leu Thr Ala Gln Leu Thr Leu Gln Arg Gln
1               5                   10                  15 aaa atc caa gag ctg acc aca aat gca aag gaa aca cat acc aaa cta        96
Lys Ile Gln Glu Leu Thr Thr Asn Ala Lys Glu Thr His Thr Lys Leu
                20                  25                  30 gcc ctt gct gaa gcc aga gtt cag gag gaa gag cag aag gca acc aga       144
Ala Leu Ala Glu Ala Arg Val Gln Glu Glu Glu Gln Lys Ala Thr Arg
            35                  40                  45 cta gag                                                               150
Leu Glu
    50

<210> SEQ ID NO 34
<211> LENGTH: 50
<212> TYPE: PRT
<213> ORGANISM: Homo sapiens
```

```
<400> SEQUENCE: 34

Val Asp Glu Gln Gln Arg Leu Thr Ala Gln Leu Thr Leu Gln Arg Gln
1               5                   10                  15

Lys Ile Gln Glu Leu Thr Thr Asn Ala Lys Glu Thr His Thr Lys Leu
                20                  25                  30

Ala Leu Ala Glu Ala Arg Val Gln Glu Glu Gln Lys Ala Thr Arg
            35                  40                  45

Leu Glu
    50

<210> SEQ ID NO 35
<211> LENGTH: 720
<212> TYPE: DNA
<213> ORGANISM: Homo sapiens
<220> FEATURE:
<221> NAME/KEY: CDS
<222> LOCATION: (1)..(720)
<223> OTHER INFORMATION:

<400> SEQUENCE: 35 atg cgt tcc aga ggc agt gat acc gag ggc tca gcc caa aag aaa ttt      48
Met Arg Ser Arg Gly Ser Asp Thr Glu Gly Ser Ala Gln Lys Lys Phe
1               5                   10                  15 cca aga cat act aaa ggc cac agt ttc caa ggg cct aaa aac atg aag      96
Pro Arg His Thr Lys Gly His Ser Phe Gln Gly Pro Lys Asn Met Lys
                20                  25                  30 cat aga cag caa gac aaa gac tcc ccc agt gag tcg gat gta ata ctt     144
His Arg Gln Gln Asp Lys Asp Ser Pro Ser Glu Ser Asp Val Ile Leu
            35                  40                  45 ccg tgt ccc aag gca gag aag cca cac agt ggt aat ggc cac caa gca     192
Pro Cys Pro Lys Ala Glu Lys Pro His Ser Gly Asn Gly His Gln Ala
        50                  55                  60 gaa gac ctc tca aga gat gac ctg tta ttt ctc ctc agc att ctg gag     240
Glu Asp Leu Ser Arg Asp Asp Leu Leu Phe Leu Leu Ser Ile Leu Glu
65                  70                  75                  80 gga gaa ctg cag gct cga gat gag gtc ata ggc att tta aag gct gaa     288
Gly Glu Leu Gln Ala Arg Asp Glu Val Ile Gly Ile Leu Lys Ala Glu
                85                  90                  95 aaa atg gac ctg gct ttg ctg gaa gct cag tat ggg ttt gtc act cca     336
Lys Met Asp Leu Ala Leu Leu Glu Ala Gln Tyr Gly Phe Val Thr Pro
            100                 105                 110 aaa aag gtg tta gag gct ctc cag aga gat gct ttt caa gcg aaa tct     384
Lys Lys Val Leu Glu Ala Leu Gln Arg Asp Ala Phe Gln Ala Lys Ser
        115                 120                 125 acc cct tgg cag gag gac atc tat gag aaa cca atg aat gag ttg gac     432
Thr Pro Trp Gln Glu Asp Ile Tyr Glu Lys Pro Met Asn Glu Leu Asp
    130                 135                 140 aaa gtt gtg gaa aaa cat aaa gaa tct tac aga cga atc ctg gga cag     480
Lys Val Val Glu Lys His Lys Glu Ser Tyr Arg Arg Ile Leu Gly Gln
145                 150                 155                 160 ctt tta gtg gca gaa aaa tcc cat agg caa acc ata ttg gag ttg gag     528
Leu Leu Val Ala Glu Lys Ser His Arg Gln Thr Ile Leu Glu Leu Glu
                165                 170                 175 gaa gaa aag aga aaa cat aaa gaa tac atg gag aag agt gat gaa ttc     576
Glu Glu Lys Arg Lys His Lys Glu Tyr Met Glu Lys Ser Asp Glu Phe
            180                 185                 190 ata tgc cta cta gaa cag gaa tgt gaa aga tta aag aag cta att gat     624
Ile Cys Leu Leu Glu Gln Glu Cys Glu Arg Leu Lys Lys Leu Ile Asp
        195                 200                 205 caa gaa atc aag tct cag gag gag aag gag caa gaa aag gag aaa agg     672
```

```
Gln Glu Ile Lys Ser Gln Glu Glu Lys Glu Gln Glu Lys Glu Lys Arg
    210                 215                 220 gtc acc acc ctg aaa gag gag ctg acc aag ctg aag tct ttt gct ttg        720
Val Thr Thr Leu Lys Glu Glu Leu Thr Lys Leu Lys Ser Phe Ala Leu
225                 230                 235                 240

<210> SEQ ID NO 36
<211> LENGTH: 240
<212> TYPE: PRT
<213> ORGANISM: Homo sapiens

<400> SEQUENCE: 36

Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Asp Leu Leu Phe Leu Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

Thr Pro Trp Gln Glu Asp Ile Tyr Glu Lys Pro Met Asn Glu Leu Asp
    130                 135                 140

Lys Val Val Glu Lys His Lys Glu Ser Tyr Arg Arg Ile Leu Gly Gln
145                 150                 155                 160

Leu Leu Val Ala Glu Lys Ser His Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205

Gln Glu Ile Lys Ser Gln Glu Glu Lys Glu Gln Glu Lys Glu Lys Arg
    210                 215                 220

Val Thr Thr Leu Lys Glu Glu Leu Thr Lys Leu Lys Ser Phe Ala Leu
225                 230                 235                 240

<210> SEQ ID NO 37
<211> LENGTH: 1152
<212> TYPE: DNA
<213> ORGANISM: Homo sapiens
<220> FEATURE:
<221> NAME/KEY: CDS
<222> LOCATION: (1)..(1152)
<223> OTHER INFORMATION:

<400> SEQUENCE: 37 cta aat caa caa gaa aac agg aac aga gat tta gga aga gag att gaa        48
Leu Asn Gln Gln Glu Asn Arg Asn Arg Asp Leu Gly Arg Glu Ile Glu
1               5                   10                  15 aac ctc act aag gag tta gag agg tac cgg cat ttc agt aag agc ctc        96
Asn Leu Thr Lys Glu Leu Glu Arg Tyr Arg His Phe Ser Lys Ser Leu
            20                  25                  30
```

| | | |
|---|---|---|
| agg cct agt ctc aat gga aga aga att tcc gat cct caa gta ttt tct<br>Arg Pro Ser Leu Asn Gly Arg Arg Ile Ser Asp Pro Gln Val Phe Ser<br>35 40 45 | | 144 |
| aaa gaa gtt cag aca gaa gca gta gac aat gaa cca cct gat tac aag<br>Lys Glu Val Gln Thr Glu Ala Val Asp Asn Glu Pro Pro Asp Tyr Lys<br>50 55 60 | | 192 |
| agc ctc att cct ctg gaa cgt gca gtc atc aat ggt cag tta tat gag<br>Ser Leu Ile Pro Leu Glu Arg Ala Val Ile Asn Gly Gln Leu Tyr Glu<br>65 70 75 80 | | 240 |
| gag agt gag aat caa gac gag gac cct aat gat gag gga tct gtg ctg<br>Glu Ser Glu Asn Gln Asp Glu Asp Pro Asn Asp Glu Gly Ser Val Leu<br>85 90 95 | | 288 |
| tcc ttc aaa tgc agc cag tct act cca tgt cct gtt aac aga aag cta<br>Ser Phe Lys Cys Ser Gln Ser Thr Pro Cys Pro Val Asn Arg Lys Leu<br>100 105 110 | | 336 |
| tgg att ccc tgg atg aaa tcc aag gag ggc cat ctt cag aat gga aaa<br>Trp Ile Pro Trp Met Lys Ser Lys Glu Gly His Leu Gln Asn Gly Lys<br>115 120 125 | | 384 |
| atg caa act aaa ccc aat gcc aac ttt gtg caa cct gga gat cta gtc<br>Met Gln Thr Lys Pro Asn Ala Asn Phe Val Gln Pro Gly Asp Leu Val<br>130 135 140 | | 432 |
| cta agc cac aca cct ggg cag cca ctt cat ata aag gtt act cca gac<br>Leu Ser His Thr Pro Gly Gln Pro Leu His Ile Lys Val Thr Pro Asp<br>145 150 155 160 | | 480 |
| cat gta caa aac aca gcc act ctt gaa atc aca agt cca acc aca gag<br>His Val Gln Asn Thr Ala Thr Leu Glu Ile Thr Ser Pro Thr Thr Glu<br>165 170 175 | | 528 |
| agt cct cac tct tac acg agt act gca gtg ata ccg aac tgt ggc acg<br>Ser Pro His Ser Tyr Thr Ser Thr Ala Val Ile Pro Asn Cys Gly Thr<br>180 185 190 | | 576 |
| cca aag caa agg ata acc atc ctc caa aac gcc tcc ata aca cca gta<br>Pro Lys Gln Arg Ile Thr Ile Leu Gln Asn Ala Ser Ile Thr Pro Val<br>195 200 205 | | 624 |
| aag tcc aaa acc tct acc gaa gac ctc atg aat tta gaa caa ggc atg<br>Lys Ser Lys Thr Ser Thr Glu Asp Leu Met Asn Leu Glu Gln Gly Met<br>210 215 220 | | 672 |
| tcc cca att acc atg gca acc ttt gcc aga gca cag acc cca gag tct<br>Ser Pro Ile Thr Met Ala Thr Phe Ala Arg Ala Gln Thr Pro Glu Ser<br>225 230 235 240 | | 720 |
| tgt ggt tct cta act cca gaa agg aca atg tcc cct att cag gtt ttg<br>Cys Gly Ser Leu Thr Pro Glu Arg Thr Met Ser Pro Ile Gln Val Leu<br>245 250 255 | | 768 |
| gct gtg act ggt tca gct agc tct cct gag cag gga cgc tcc cca gaa<br>Ala Val Thr Gly Ser Ala Ser Ser Pro Glu Gln Gly Arg Ser Pro Glu<br>260 265 270 | | 816 |
| cca aca gaa atc agt gcc aag cat gcg ata ttc aga gtc tcc cca gac<br>Pro Thr Glu Ile Ser Ala Lys His Ala Ile Phe Arg Val Ser Pro Asp<br>275 280 285 | | 864 |
| cgg cag tca tca tgg cag ttt cag cgt tca aac agc aat agc tca agt<br>Arg Gln Ser Ser Trp Gln Phe Gln Arg Ser Asn Ser Asn Ser Ser Ser<br>290 295 300 | | 912 |
| gtg ata act act gag gat aat aaa atc cac att cac tta gga agt cct<br>Val Ile Thr Thr Glu Asp Asn Lys Ile His Ile His Leu Gly Ser Pro<br>305 310 315 320 | | 960 |
| tac atg caa gct gta gcc agc cct gtg aga cct gcc agc cct tca gca<br>Tyr Met Gln Ala Val Ala Ser Pro Val Arg Pro Ala Ser Pro Ser Ala<br>325 330 335 | | 1008 |
| cca ctg cag gat aac cga act caa ggc tta att aac ggg gca cta aac<br>Pro Leu Gln Asp Asn Arg Thr Gln Gly Leu Ile Asn Gly Ala Leu Asn | | 1056 |

```
                      340             345             350
aaa aca acc aat aaa gtc acc agc agt att act atc aca cca aca gcc    1104
Lys Thr Thr Asn Lys Val Thr Ser Ser Ile Thr Ile Thr Pro Thr Ala
        355                 360                 365 aca cct ctt cct cga caa tca caa att aca gta agt aat ata tat aac    1152
Thr Pro Leu Pro Arg Gln Ser Gln Ile Thr Val Ser Asn Ile Tyr Asn
    370                 375                 380
```

<210> SEQ ID NO 38
<211> LENGTH: 384
<212> TYPE: PRT
<213> ORGANISM: Homo sapiens

<400> SEQUENCE: 38

```
Leu Asn Gln Gln Glu Asn Arg Asn Arg Asp Leu Gly Arg Glu Ile Glu
1               5                   10                  15

Asn Leu Thr Lys Glu Leu Glu Arg Tyr Arg His Phe Ser Lys Ser Leu
            20                  25                  30

Arg Pro Ser Leu Asn Gly Arg Ile Ser Asp Pro Gln Val Phe Ser
        35                  40                  45

Lys Glu Val Gln Thr Glu Ala Val Asp Asn Glu Pro Pro Asp Tyr Lys
    50                  55                  60

Ser Leu Ile Pro Leu Glu Arg Ala Val Ile Asn Gly Gln Leu Tyr Glu
65                  70                  75                  80

Glu Ser Glu Asn Gln Asp Glu Asp Pro Asn Asp Glu Gly Ser Val Leu
                85                  90                  95

Ser Phe Lys Cys Ser Gln Ser Thr Pro Cys Pro Val Asn Arg Lys Leu
            100                 105                 110

Trp Ile Pro Trp Met Lys Ser Lys Glu Gly His Leu Gln Asn Gly Lys
        115                 120                 125

Met Gln Thr Lys Pro Asn Ala Asn Phe Val Gln Pro Gly Asp Leu Val
    130                 135                 140

Leu Ser His Thr Pro Gly Gln Pro Leu His Ile Lys Val Thr Pro Asp
145                 150                 155                 160

His Val Gln Asn Thr Ala Thr Leu Glu Ile Thr Ser Pro Thr Thr Glu
                165                 170                 175

Ser Pro His Ser Tyr Thr Ser Thr Ala Val Ile Pro Asn Cys Gly Thr
            180                 185                 190

Pro Lys Gln Arg Ile Thr Ile Leu Gln Asn Ala Ser Ile Thr Pro Val
        195                 200                 205

Lys Ser Lys Thr Ser Thr Glu Asp Leu Met Asn Leu Glu Gln Gly Met
    210                 215                 220

Ser Pro Ile Thr Met Ala Thr Phe Ala Arg Ala Gln Thr Pro Glu Ser
225                 230                 235                 240

Cys Gly Ser Leu Thr Pro Glu Arg Thr Met Ser Pro Ile Gln Val Leu
                245                 250                 255

Ala Val Thr Gly Ser Ala Ser Ser Pro Glu Gln Gly Arg Ser Pro Glu
            260                 265                 270

Pro Thr Glu Ile Ser Ala Lys His Ala Ile Phe Arg Val Ser Pro Asp
        275                 280                 285

Arg Gln Ser Ser Trp Gln Phe Gln Arg Ser Asn Ser Asn Ser Ser Ser
    290                 295                 300

Val Ile Thr Thr Glu Asp Asn Lys Ile His Ile His Leu Gly Ser Pro
305                 310                 315                 320

Tyr Met Gln Ala Val Ala Ser Pro Val Arg Pro Ala Ser Pro Ser Ala
```

-continued

```
                325                 330                 335
Pro Leu Gln Asp Asn Arg Thr Gln Gly Leu Ile Asn Gly Ala Leu Asn
            340                 345                 350

Lys Thr Thr Asn Lys Val Thr Ser Ser Ile Thr Ile Thr Pro Thr Ala
            355                 360                 365

Thr Pro Leu Pro Arg Gln Ser Gln Ile Thr Val Ser Asn Ile Tyr Asn
            370                 375                 380
```

GIPS, A FAMILY OF POLYPEPTIDES WITH TRANSCRIPTION FACTOR ACTIVITY THAT INTERACT WITH GOODPASTURE ANTIGEN BINDING PROTEIN

CROSS REFERENCE

This application claims priority to U.S. Provisional Patent Application Nos. 60/338,287 filed Dec. 7, 2001 and 60/382,004 filed May 20, 2002.

FIELD OF THE INVENTION

The present invention is in the general fields of molecular biology, cell biology, protein-protein interactions, autoimmunity, cancer, and drug discovery.

BACKGROUND

Goodpasture antigen binding protein (GPBP) is a ubiquitous protein kinase with a $M_r$ of 80–89 kDa that is preferentially expressed in tissues and cells that are common targets of autoimmune responses, such as the Langerhans islets (type I diabetes); the white matter of the central nervous system (multiple sclerosis); the biliary ducts (primary biliary cirrhosis); the cortical cells of the adrenal gland (Addison disease); striated muscle cells (myasthenia gravis); spermatogonium (male infertility); Purkinje cells of the cerebellum (paraneoplasic cerebellar degeneration syndrome); and intestinal epithelial cells (pernicious anemia, autoimmune gastritis and enteritis).

GPBP is expressed as two isoforms (GPBP and GPBPΔ26) which result from exon alternative splicing of the corresponding pre-mRNA. GPBP is the more active variant, and its expression is still more restricted to histological structures targeted by common autoimmune responses including human alveolar and glomerular basement membranes (Goodpasture disease). GPBP binds to and phosphorylates the human α3 NC1 domain of type IV collagen (α3(IV)NC1) also called the Goodpasture antigen (WO 00/50607), as this domain is the target of the pathogenic autoantibodies mediating the Goodpasture autoimmune response. Phosphorylation activates the α3(IV)NC1 domain for aggregation, a process that is catalyzed at least in part by GPBP and which comprises conformational isomerization reactions and disulfide-bond exchange (WO 02/061430).

An augmented expression of GPBP with respect to GPBPΔ26 has been associated with the production of non-tolerized, aberrant conformational versions of the human α3(IV)NC1 domain ("aberrant conformers") and the subsequent autoantibody production that causes Goodpasture disease (WO 02/061430). The evidence suggests that a similar pathogenic mechanism is involved in other autoimmune conditions, including cutaneous lupus erythematosus, pemphigus, pemphigoid and lichen planus, and that aberrant GPBP expression and autoimmune pathogenesis are related processes. Furthermore, GPBP is down-regulated in cancer cell lines (WO 00/50607), suggesting that the cell machinery harboring GPBP/GPBPΔ26 is also involved in signaling pathways that decrease cell division or induce cell death. These pathways could be up regulated during autoimmune pathogenesis to cause altered antigen presentation in individuals carrying specific MHC haplotypes, and down regulated during cell transformation to prevent autoimmune attack of the transformed cells during tumor growth.

Based on all of the above, there exists a need in the art to identify methods and reagents for modifying GPBP activity for use in treating autoimmune disorders and cancer.

SUMMARY OF THE INVENTION

In one aspect, the present invention provides isolated GPBP-interacting 90 and 130 kDa polypeptides, and portions thereof (GIP90/130 polypeptides), antibodies to the GIP 90/130 polypeptides, and pharmaceutical compositions thereof. In a further aspect, the present invention provides isolated GIP90/130 nucleic acid sequences, expression vectors comprising the nucleic acid sequences, and host cells transfected with the expression vectors. The invention further provides methods for detecting the GIP90/130 polypeptides or nucleic acid sequences, methods for modifying interactions between GPBP and GIP90/130 polypeptides, aggregation of GIP90/130 polypeptides, and GIP90/130 polypeptide-mediated gene transcription, and methods for treating patients with autoimmune disorders or cancer.

BRIEF DESCRIPTION OF THE FIGURES

FIG. 3 is a sequence alignment of the full length GIP90/130 polypeptides and DOC1 and DOC1-related protein.

FIG. 4 is the amino acid sequence of I-20. Residues in bold font are those identified as essential for interactions between GIP90/130 and GPBP; in small letters are other residues identified as participating in interaction between GIP90/130 and GPBP, but not essential; and underlined are the residues implicated in GIP90/130 aggregation.

DETAILED DESCRIPTION OF THE INVENTION

Figure 1:
FIG. 1 is a diagram of the exon-intron structure of the GIP90 genomic DNA as determined by BLAST search against Human Genome NCBI in May 20, 2002.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109–128, ed. E. J. Murray, The Humana Press Inc., Clifton, N.J.), and the Ambion 1998 Catalog (Ambion, Austin, Tex.).

As used herein, the term "GIP90/130" and "GIP90/130 polypeptide(s)" refers to the family of GPBP-interacting proteins that includes GIP90, GIP130a, GIP130b, and GIP130c, amino acid sequences derived therefrom, and includes both monomers and oligomers thereof.

As used herein, the term "GIP90" refers to the 90 kDa form of GIP, which consists of the amino acid sequence of SEQ ID NO: 10, and includes both monomers and oligomers thereof.

As used herein, the term "GIP130a" refers to one of the 130 kDa forms of GIP, which consists of the amino acid sequence of SEQ ID NO:12, and includes both monomers and oligomers thereof.

As used herein, the term "GIP130b" refers to one of the 130 kDa forms of GIP, which consists of the amino acid sequence of SEQ ID NO:14, and includes both monomers and oligomers thereof.

As used herein, the term "GIP130c" refers to one of the 130 kDa forms of GIP, which consists of the amino acid sequence of SEQ ID NO:16, and includes both monomers and oligomers thereof.

The numbering of nucleotides and residues used below for GIP proteins refer to the GenBank accession number AF329092.

As used herein, the term "DOC proteins" or "DOC1 proteins" refers to down regulated in ovarian cancer-1 (DOC1) (Genbank accession number NM 014890) and DOC1-related protein (Genbank accession number BC027860). DOC1 and DOC1-related protein are derived from the same gene since they are identical in the homology region at nucleotide and amino acid levels As used herein, the term "GPBP" refers to Goodpasture antigen binding protein, and includes both monomers and oligomers thereof, as disclosed in WO 00/50607.

As used herein, the term "GPBPΔ26" refers to the Goodpasture antigen binding protein alternatively spliced product deleted for 26 amino acid residues as disclosed in WO 00/50607, and includes both monomers and oligomers thereof.

As used herein pol κ means the primary protein product of the POLK as disclosed in WO 02/46378.

As used herein, pol κ76 means the 76 kDa alternatively spliced isoform product of the POLK as disclosed in WO 02/46378.

As used herein, "aggregation" refers to both self-aggregation of an individual GIP90/130 polypeptide, and aggregation of two or more different GIP90/130 polypeptides.

In one aspect, the present invention provides isolated GIP90/130 polypeptides. In one embodiment, the isolated GIP90/130 polypeptide comprises at least 6 amino acids of the amino acid sequence of SEQ ID NO:2, which is a unique 10 amino acid polypeptide (SYRRILGQLL) that is herein demonstrated to be essential for the interaction between GIP90/130 and GPBP (discussed in detail below), and is not present in DOC proteins. In further embodiments, the isolated GIP90/130 polypeptide comprises at least 7, 8, 9, or 10 amino acids of the amino acid sequence of SEQ ID NO:2. In still further embodiments, the isolated GIP90/130 polypeptide consists of at least 6, 7, 8, 9, or 10 amino acids of the amino acid sequence of SEQ ID NO:2. These polypeptides can be used, for example, to modify interactions between GPBP and GIP90/130 polypeptides or to raise antibodies that interfere with GPBP-GIP90/130 interaction.

In further embodiments, the isolated GIP90/130 polypeptide comprises and/or consists of the amino acid sequence of SEQ ID NO:4, which is the N-terminal region of GIP90/130a/c that is not present in DOC proteins (described in detail below), and which is encoded by exon II–IV and part of exon V (FIG. 3). These polypeptides are thus useful, for example, to develop reagents, such as antibodies, that can distinguish between GIP90/130 and DOC proteins. This polypeptide includes sequences implicated in the interaction between GPBP and GIP90/130 (including SEQ ID NO: 2), and thus can be used (or antibodies to the polypeptides can be used), for example, to modify interactions between GPBP and GIP90/130 polypeptides. This polypeptide also includes sequences implicated in GIP90/130 aggregation, and thus can further be used (or antibodies to the polypeptides can be used) to modify GIP90/130 aggregation. This polypeptide also includes sequences implicated in the transcriptional activity of GIP90/130 and thus the polypeptides, or antibodies derived therefrom, can be further used for modulating specific gene expression.

The polypeptides of the invention also include polypeptides comprising and/or consisting of the amino acid sequence of SEQ ID NO: 6, which is referred to as I-20, a 265 amino acid polypeptide that is described in detail below. This polypeptide interacts more strongly with GPBP and pol κ76 than the full length GIP90/130 polypeptides, and aggregates more efficiently than the full length GIP90/130 polypeptides. Furthermore, I-20 does not induce gene transcription, in contrast to the full length GIP90/130 polypeptides. Therefore this polypeptide can be used (or antibodies to the polypeptides can be used), for example, to modify (a) interactions between GPBP and GIP90/130 polypeptides; (b) interactions between pol κ76 and GIP90/130 polypeptides; (c) GIP90/130 polypeptide aggregation; and (d) other functions of the GIP90/130 polypeptides, such as induction of gene transcription.

The polypeptides of the invention also include polypeptides comprising and/or consisting of the amino acid sequence of SEQ ID NO:8, which consists of the N-terminus of GIP90 to the end of I-20, and is encoded by exons II–IV and part of exon V up to the end of the I-20 coding sequence. This polypeptide includes sequences implicated in (a) the interaction between GPBP and GIP90/130 polypeptides, (b) GIP90/130 polypeptide aggregation, and (c) the transcriptional activity of GIP90/130 polypeptides, and thus the polypeptides, or antibodies derived therefrom, can be used, for example, to modify interactions between GPBP and GIP90/130 polypeptides, to modify GIP90/130 aggregation, and to modulate gene expression.

The polypeptides of the invention also include polypeptides comprising and/or consisting of the amino acid sequence of SEQ ID NO:10 (GIP90), SEQ ID NO:12 (GIP130a), SEQ ID NO:14 (GIP130b), or SEQ ID NO:16 (GIP130c). These full length polypeptides, described in more detail below, interact with GPBP and are capable of aggregation. These polypeptides can be used, for example, to modify GPBP-GIP90/130 interactions, to modify GIP90/130 aggregation, to modulate gene expression, as well as for other purposes described herein.

In a further embodiment, the isolated GIP 90/130 polypeptide comprises at least 8 amino acids of the amino acid sequence of SEQ ID NO:18, which is a unique 15 amino acid peptide that is present at the C-terminus of GIP90 and is not present in DOC proteins, GIP130a, GIP130b, or GIP130c, and thus can be used, for example, to generate reagents, such as antibodies, to distinguish GIP90 from other members of the GIP90/130 polypeptide family. Furthermore, the polypeptides, or antibodies thereto, can be used to specifically modify GIP90 self-aggregation. In further embodiments, the isolated GIP90/130 polypeptide comprises or consists of at least 9, 10, 11, 12, 13, 14, or 15 amino acids of the amino acid sequence of SEQ ID NO:18.

In a further embodiment, the isolated GIP90/130 polypeptide consists of at least 8 amino acids of the amino acid sequence of SEQ ID NO:20, which is a 30 amino acid polypeptide present within I-20 that has been implicated in the interaction of GIP90/130 with GPBP and also in GIP90/130 aggregation. In further embodiments, the isolated GIP90/130 polypeptide consists of at least 9, 10, 11, 12, 13, 14, 15, 16, 17, 18, 19, 20, 21, 22, 23, 24, 25, 26, 27, 28, 29, or 30 amino acids the amino acid sequence of SEQ ID NO:20. Thus, these polypeptides, or antibodies to the polypeptides, can be used, for example, to modify interactions between GPBP and GIP90/130 polypeptides. Furthermore, since this polypeptide is present in each of GIP90, GIP130a, GIP130b, GIP130c, and DOC1 proteins, these polypeptides, or antibodies thereto, can be used to generally modify aggregation of the GIP90/130 polypeptides and DOC1 proteins. Despite the fact that DOC1 proteins contain SEQ ID NO:20, they do not interact in a two hybrid assay with GPBP (see below), and thus SEQ ID NO:20, while implicated in the interaction of GIP90/130 polypeptides and GPBP, is not sufficient for GPBP interaction.

In a still further embodiment, the isolated GIP90/130 polypeptide comprises or consists of the amino acid sequence of SEQ ID NO:22, which is a unique 386 amino acid polypeptide that is present at the C-terminus of GIP130a but is not present in GIP90, is not wholly present in DOC1, and includes variations from GIP130b, GIP130c, and DOC1-related protein, and thus can be used, for example, to modify GIP130a aggregation, and to generate reagents, such as antibodies, to distinguish GIP130a from other members of the GIP90/130 polypeptide family, and the DOC proteins. This region contains sequences that down-regulate GIP 90/130 interaction with GPBP which can be used to modify GIP90/130-GPBP interaction, or to generate reagents, such as antibodies for the same purposes.

In a still further embodiment, the isolated GIP90/130 polypeptide comprises or consists of the amino acid sequence of SEQ ID NO:24, which is GIP130a deleted from the N-terminus to the end of I-20. This polypeptide lacks critical regions of the GIP90/130 polypeptides implicated in GPBP interaction and induction of gene expression, and like the C terminus of GIP130b/c contains amino acid sequences that down-regulate interaction with GPPB. Thus, the polypeptides, or antibodies thereto, can be used, for example, to modify GPBP-GIP90/130 polypeptide interactions or to modify GIP90/130 polypeptide aggregation.

In a still further embodiment, the isolated GIP 90/130 polypeptide comprises or consists of the amino acid sequence of SEQ ID NO:26, which is a unique 7 amino acid polypeptide present at the C-terminus of GIP130a, and is not present in any of GIP90, GIP130b, GIP130c, and DOC proteins. Thus, these polypeptides can be used to produce reagents, such as antibodies, that are specific for GIP130a, and which can be used, for example, to specifically modify GIP130a aggregation.

In another embodiment, the isolated GIP90/130 polypeptide comprises at least 6 amino acids of the amino acid sequence of SEQ ID NO:28, which is a unique 10 amino acid polypeptide (LDKVVEKHKE) within I-20 that participates in interactions between GIP90/130 polypeptides and GPBP, is essential for GIP90/130 polypeptide aggregation, and is not present in DOC proteins. In further embodiments, the isolated GIP90/130 polypeptide comprises or consists of at least 7, 8, 9, or 10 amino acids of the amino acid sequence of SEQ ID NO:28. These polypeptides or antibodies raised against them can be used, for example, to modify interactions between GPBP and GIP90/130 polypeptides or to modify GIP90/130 polypeptide aggregation.

In another embodiment, the isolated GIP90/130 polypeptide consists of at least 6 amino acids of the amino acid sequence of SEQ ID NO:30, which is an 10 amino acid polypeptide (EEEQKATRLE) within I-20 that participates in interactions between GIP90/130 polypeptides and GPBP, is essential for GIP90/130 polypeptide aggregation, and is present in DOC proteins. In further embodiments, the isolated GIP90/130 polypeptide consists of at least 7, 8, 9, or 10 amino acids of the amino acid sequence of SEQ ID NO:30. These polypeptides or antibodies raised against them can be used, for example, to modify interactions between GPBP and GIP90/130 polypeptides or to modify GIP90/130 polypeptide aggregation. Furthermore, since this polypeptide is present in each of GIP90, GIP130a, GIP130b, GIP130c, and DOC1 proteins, these polypeptides, or antibodies thereto, can be used to generally modify aggregation of the GIP90/130 polypeptides and DOC1/DOC1-related proteins. Despite the fact that DOC1 proteins contain SEQ ID NO:20, they do not interact in a two hybrid assay with GPBP (see below), and thus SEQ ID NO:20, while implicated in the interaction of GIP90/130 polypeptides and GPBP, is not sufficient for GPBP interaction.

In another embodiment, the isolated GIP90/130 polypeptide comprises at least 8 amino acids of the amino acid sequence of SEQ ID NO:32, which is a unique 20 amino acid polypeptide (LDKVVEKHKESYRRILGQLL) within I-20 that contains essential residues for the interaction between GIP90/130 polypeptides and GPBP and for GIP90/130 polypeptide aggregation, and is not present in DOC proteins. In further embodiments, the isolated GIP90/130 polypeptide comprises or consists of at least 9, 10, 11, 12, 13, 14, 15, 16, 17, 18, 19, or 20 amino acids of the amino acid sequence of SEQ ID NO:32. These polypeptides can be used, for example, to modify interactions between GPBP and GIP90/130 polypeptides and to modify GIP90/130 polypeptide aggregation, or to raise antibodies that modify interactions between GPBP and GIP90/130 polypeptides and to modify GIP90/130 polypeptide aggregation.

In another embodiment, the isolated GIP90/130 polypeptide consists of at least 8 amino acids of the amino acid sequence of SEQ ID NO:34, which is a 50 amino acid polypeptide that is contained within I-20, contains regions essential for the interaction between GIP90/130 polypeptides and GPBP and for GIP90/130 polypeptide aggregation, and is present in DOC proteins. In further embodiments, the isolated GIP90/130 polypeptide consists of at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids of the amino acid sequence of SEQ ID NO:34. These polypeptides can be used, for example, to modify interactions between GPBP and GIP90/130 polypeptides and to modify GIP90/130 polypeptide aggregation, or to raise antibodies that modify interactions between GPBP and GIP90/130 polypeptides and to modify GIP90/130 polypeptide aggregation. Furthermore, since this polypeptide is present in each of GIP90, GIP130a, GIP130b, GIP130c, and DOC1 proteins, these polypeptides, or antibodies thereto, can be used to generally modify aggregation of the GIP90/130 polypeptides and DOC1/DOC1-related proteins. Despite the fact that DOC1 proteins contain SEQ ID NO:20, they do not interact in a two hybrid assay with GPBP (see below), and thus SEQ ID NO:20, while implicated in the interaction of GIP90/130 polypeptides and GPBP, is not sufficient for GPBP interaction.

The polypeptides of the invention also include polypeptides comprising and/or consisting of the amino acid sequence of SEQ ID NO:36, which consists of the first 240 amino acids of the N-terminus of GIP130b, which is not present in DOC1 proteins, and which differs from the corresponding sequence in GIP90, GIP130a, and GIP130c by a single amino acid residue at position 168. This polypeptide includes sequences implicated in (a) the interaction between GPBP and GIP90/130 polypeptides, (b) GIP90/130 polypeptide aggregation, and (c) the transcriptional activity of GIP90/130 polypeptides, and thus the polypeptides, or antibodies derived therefrom, can be used, for example, to modify interactions between GPBP and GIP90/130 polypeptides, to modify GIP90/130 aggregation, and to modulate gene expression.

In a still further embodiment, the isolated GIP 90/130 polypeptide consists of the amino acid sequence of SEQ ID NO:38 which is a unique 384 amino acid polypeptide that is present at the C terminus of GIP130b/c and DOC1-related protein but is not present in GIP90, is not wholly present in DOC1, and includes variations from GIP130a, and thus can be used, for example, to modify GIP130b/c aggregation, and to generate reagents, such as antibodies, to distinguish GIP130b/c and the DOC1-related protein from other members of the GIP90/130 polypeptide family.

As used herein, an "isolated polypeptide" refers to a polypeptide that is substantially free of other proteins, cellular material and culture medium when isolated from cells or produced by recombinant DNA techniques, or chemical precursors or other chemicals when chemically synthesized. Thus, the protein can either be purified from natural sources, chemically synthesized, or recombinant protein can be purified from the recombinant host cells disclosed below.

Synthetic polypeptides, prepared using the well known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with the standard deprotecting, neutralization, coupling and wash protocols of the original solid phase procedure of Merrifield (1963, J. Am. Chem. Soc. 85:2149–2154), or the base-labile Nα-amino protected 9-fluorenylmethoxycarbonyl (Fmoc) amino acids first described by Carpino and Han (1972, J. Org. Chem. 37:3403–3409). Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art.

Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers. The polypeptides of the invention may comprise D-amino acids (which are resistant to L-amino acid-specific proteases in vivo), a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine.

In addition, the polypeptides can have peptidomimetic bonds, such as ester bonds, to prepare peptides with novel properties. For example, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo.

Alternatively, the proteins are produced by the recombinant host cells disclosed below, and purified using standard techniques. (See for example, *Molecular Cloning: A Laboratory Manual* (Sambrook, et al., 1989, Cold Spring Harbor Laboratory Press.)) The protein can thus be purified from prokaryotic or eukaryotic sources. In various further preferred embodiments, the protein is purified from bacterial, yeast, or mammalian cells.

The protein may comprise additional sequences useful for promoting purification of the protein, such as epitope tags and transport signals. Examples of such epitope tags include, but are not limited to FLAG (Sigma Chemical, St. Louis, Mo.), myc (9E10) (Invitrogen, Carlsbad, Calif.), 6-His (Invitrogen; Novagen, Madison, Wis.), and HA (Boehringer Manheim Biochemicals). Examples of such transport signals include, but are not limited to, export signals, secretory signals, nuclear localization signals, and plasma membrane localization signals.

In another aspect, the present invention provides antibodies against the GIP90/130 polypeptides disclosed herein. Such antibodies can be used in a manner similar to the polypeptides they recognize in modifying GPBP-GIP90/130 interactions, modifying GIP90/130 aggregation, and/or modifying GIP90/130-mediated transcriptional activity. Furthermore, such antibodies can be used to distinguish between members of the GIP90/130 family, as discussed above.

In one embodiment, the antibodies are directed against an epitope present in a polypeptide of one or more of the amino acid sequences selected from the group consisting of SEQ ID NO:2, SEQ ID NO:4, SEQ ID NO:18, SEQ ID NO:26, SEQ ID NO:28, SEQ ID NO:32, and SEQ ID NO:36. In a further embodiment, the antibodies are directed against an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, and SEQ ID NO:38.

Antibodies can be made by well-known methods, such as described in Harlow and Lane, Antibodies; A Laboratory Manual, Cold Spring Harbor Laboratory, Cold Spring Harbor, N.Y., (1988). In one example, pre-immune serum is collected prior to the first immunization. A peptide portion of the amino acid sequence of a GIP90/130 polypeptide, together with an appropriate adjuvant, is injected into an animal in an amount and at intervals sufficient to elicit an immune response. Animals are bled at regular intervals, preferably weekly, to determine antibody titer. The animals may or may not receive booster injections following the initial immunization. At about 7 days after each booster immunization, or about weekly after a single immunization, the animals are bled, the serum collected, and aliquots are stored at about −20° C. Polyclonal antibodies against GIP90/130 polypeptides can then be purified directly by passing serum collected from the animal through a column to which non-antigen-related proteins prepared from the same expression system without GIP90/130 polypeptides bound.

Monoclonal antibodies can be produced by obtaining spleen cells from the animal. (See Kohler and Milstein, Nature 256, 495–497 (1975)). In one example, monoclonal antibodies (mAb) of interest are prepared by immunizing inbred mice with a GIP90/130 polypeptide, or portion thereof. The mice are immunized by the IP or SC route in an amount and at intervals sufficient to elicit an immune response. The mice receive an initial immunization on day 0 and are rested for about 3 to about 30 weeks. Immunized mice are given one or more booster immunizations of by the intravenous (IV) route. Lymphocytes from antibody positive mice are obtained by removing spleens from immunized mice by standard procedures known in the art. Hybridoma cells are produced by mixing the splenic lymphocytes with an appropriate fusion partner under conditions which will allow the formation of stable hybridomas. The antibody producing cells and fusion partner cells are fused in polyethylene glycol at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells and are screened for antibody production by an immunoassay such as solid phase immunoradioassay. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

To generate such an antibody response, a GIP90/130 polypeptide or portion thereof is typically formulated with a pharmaceutically acceptable carrier for parenteral administration. Such acceptable adjuvants include, but are not limited to, Freund's complete, Freund's incomplete, alum-precipitate, water in oil emulsion containing Corynebacterium parvum and tRNA. The formulation of such compositions, including the concentration of the polypeptide and the selection of the vehicle and other components, is within the skill of the art.

The term antibody as used herein is intended to include antibody fragments thereof which are selectively reactive with GIP90/130 polypeptides. Antibodies can be fragmented using conventional techniques, and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

In another aspect, the present invention provides isolated nucleic acids that encode GIP90/130 polypeptides. In one embodiment, the isolated nucleic acid sequences comprise sequences encoding an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:22, SEQ ID NO:24, SEQ ID NO:26, SEQ ID NO:28, SEQ ID NO:32, and SEQ ID NO:36. In a further embodiment, the isolated nucleic acid sequences consist of sequences encoding an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO: 18, SEQ ID NO: 20, SEQ ID NO:22, SEQ ID NO:24, SEQ ID NO:26, SEQ ID NO:28, SEQ ID NO:30, SEQ ID NO:32, SEQ ID NO;34, SEQ ID NO:36, and SEQ ID NO:38.

In another embodiment, the isolated nucleic acids comprise sequences that hybridize under high stringency conditions to a nucleic acid sequence selected from the group consisting of SEQ ID NO:1, SEQ ID NO:3, SEQ ID NO:17, SEQ ID NO:25, SEQ ID NO:27, SEQ ID NO:31, and SEQ ID NO:35, their complement, or their transcription product. Stringency of hybridization is used herein to refer to conditions under which nucleic acid hybrids are stable. As known to those of skill in the art, the stability of hybrids is reflected in the melting temperature ($T_M$) of the hybrids. $T_M$ decreases approximately 1–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein, high stringency refers to conditions that permit hybridization of those nucleic acid sequences that form stable hybrids in 0.1% SSPE at 65° C. It is understood that these conditions may be duplicated using a variety of buffers and temperatures and that they are not necessarily precise. Denhardt's solution and SSPE (see, e.g., Sambrook, Fritsch, and Maniatis, in: Molecular Cloning, A Laboratory Manual, Cold Spring Harbor Laboratory Press, 1989) are well known to those of skill in the art, as are other suitable hybridization buffers.

In another embodiment, the isolated nucleic acids comprise one or more sequences selected from the group consisting of SEQ ID NO:1, SEQ ID NO:3, SEQ ID NO:17, SEQ ID NO:25, SEQ ID NO:27, SEQ ID NO:31, and SEQ ID NO:35, their complement, or their transcription product. In a further embodiment, the isolated nucleic acid sequences comprise one or more sequences selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:21, SEQ ID NO:23, SEQ ID NO:25, SEQ ID NO:27, SEQ ID NO:31, and SEQ ID NO:35, their complement, or their transcription product. In a further embodiment, the isolated nucleic acid sequences consist of one or more sequences selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, and SEQ ID NO:37, their complement, or their transcription product.

As used herein, an "isolated nucleic acid sequence" refers to a nucleic acid sequence that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). An "isolated" GIP90/130 nucleic acid sequence according to the present invention may, however, be linked to other nucleotide sequences that do not normally flank the recited sequence, such as a heterologous promoter sequence, or other vector sequences. It is not necessary for the isolated nucleic acid sequence to be free of other cellular material to be considered "isolated", as a nucleic acid sequence according to the invention may be part of an expression vector that is used to transfect host cells (see below).

In all of these embodiments, the isolated nucleic acid sequence may comprise RNA or DNA, and may be single stranded or double stranded. Such single stranded sequences can comprise the disclosed sequence, its complement, or the transcription product thereof. The isolated sequence may further comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals.

In another embodiment, the present invention provides an expression vector comprising an isolated nucleic acid as described above, operatively linked to a promoter. In a preferred embodiment, the promoter is heterologous (i.e.: is not the naturally occurring GIP90/130 promoter). A promoter and a GIP90/130 nucleic acid sequence are "operatively linked" when the promoter is capable of driving expression of the GIP90/130 DNA into RNA.

As used herein, the term "vector" refers to a nucleic acid molecule capable of transporting another nucleic acid to which it has been linked. One type of vector is a "plasmid", which refers to a circular double stranded DNA into which additional DNA segments may be cloned. Another type of vector is a viral vector, wherein additional DNA segments may be cloned into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors), are integrated into the genome of a host cell upon introduction into the host cell, and thereby are replicated along with the host genome. Moreover, certain vectors are capable of directing the expression of nucleic acid sequences to which they are operatively linked. Such vectors are referred to herein as "recombinant expression vectors" or simply "expression vectors". In the present invention, the expression of any nucleic acid sequence is directed by operatively linking the promoter sequences of the invention to the nucleic acid sequence to be expressed. In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The vector may also contain additional sequences, such as a polylinker for subcloning of additional nucleic acid sequences and a polyadenylation signal to effect proper polyadenylation of the transcript. The nature of the polyadenylation signal is not believed to be crucial to the successful practice of the invention, and any such sequence may be employed, including but not limited to the SV40 and bovine growth hormone poly-A sites. The vector may further include a termination sequence, which can serve to enhance message levels and to minimize read through from the construct into other sequences. Finally, expression vectors typically have selectable markers, often in the form of antibiotic resistance genes, that permit selection of cells that carry these vectors.

In a further embodiment, the present invention provides recombinant host cells in which the expression vectors disclosed herein have been introduced. As used herein, the term "host cell" is intended to refer to a cell into which a nucleic acid of the invention, such as a recombinant expression vector of the invention, has been introduced. Such cells may be prokaryotic or eukaryotic.

The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The host cells can be transiently or stably transfected with one or more of the expression vectors of the invention. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. Alternatively, the host cells can be infected with a recombinant viral vector comprising the GIP90/130 nucleic acid. (See, for example, *Molecular Cloning: A Laboratory Manual* (Sambrook, et al., 1989, Cold Spring Harbor Laboratory Press; *Culture of Animal Cells: A Manual of Basic Technique*, 2$^{nd}$ Ed. (R. I. Freshney. 1987. Liss, Inc. New York, N.Y.).

In a further aspect, the invention provides methods for detecting the presence of the GIP90/130 polypeptides in a protein sample, comprising providing a protein sample to be screened, contacting the protein sample to be screened with an antibody against one or more GIP90/130 polypeptides, and detecting the formation of antibody-GIP90/130 polypeptide complexes. The antibody can be either polyclonal or monoclonal, although monoclonal antibodies are preferred. As used herein, the term "protein sample" refers to any sample that may contain GIP90/130 polypeptides, including but not limited to tissues and portions thereof, tissue sections, intact cells, cell extracts, purified or partially purified protein samples, bodily fluids, and nucleic acid expression libraries. Accordingly, this aspect of the present invention may be used to test for the presence of GIP90/130 polypeptides in these various protein samples by standard techniques including, but not limited to, immunolocalization, immunofluorescence analysis, Western blot analysis, ELISAs, and nucleic acid expression library screening, (See for example, Sambrook et al, 1989.) In one embodiment, the techniques may determine only the presence or absence of GIP90/130 polypeptides. Alternatively, the techniques may be quantitative, and provide information about the relative amount of GIP90/130 polypeptides in the sample. For quantitative purposes, ELISAs are preferred.

Detection of immunocomplex formation between GIP90/130 polypeptides and antibodies or fragments thereof directed against GIP90/130 polypeptides can be accomplished by standard detection techniques. For example, detection of immunocomplexes can be accomplished by using labeled antibodies or secondary antibodies. Such methods, including the choice of label are known to those ordinarily skilled in the art. (Harlow and Lane, Supra). Alternatively, the polyclonal or monoclonal antibodies can be coupled to a detectable substance. The term "coupled" is used to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase. Examples of suitable prosthetic-group complexes include streptavidin/biotin and avidinibiotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of suitable radioactive material include $^{125}$I, $^{131}$I, $^{35}$S or $^{3}$H.

Such methods of detection are useful for a variety of purposes, including but not limited to detecting an autoimmune condition, identifying cell division arrest or cell death, detecting GIP90/130 interactions with GPBP or other proteins, immunolocalization of GIP90/130 polypeptides in a tissue sample, Western blot analysis, and screening of expression libraries to find related proteins.

In yet another aspect, the invention provides methods for detecting the presence of nucleic acid sequences encoding GIP90/130 polypeptides in a sample comprising providing a nucleic acid sample to be screened, contacting the sample with a nucleic acid probe derived from the isolated nucleic acid sequences of the invention, or fragments thereof, and detecting complex formation.

As used herein, the term "sample" refers to any sample that may contain a GIP90/130 polypeptide-encoding nucleic acid, including but not limited to tissues and portions thereof, tissue sections, intact cells, cell extracts, purified or partially purified nucleic acid samples, DNA libraries, and bodily fluids. Accordingly, this aspect of the present invention may be used to test for the presence of GIP90/130 polypeptide-encoding mRNA or DNA in these various samples by standard techniques including, but not limited to, in situ hybridization, Northern blotting, Southern blotting, DNA library screening, polymerase chain reaction (PCR) or reverse transcription-PCR (RT-PCR). (See for example, Sambrook et al, 1989.) In one embodiment, the techniques may determine only the presence or absence of the nucleic acid of interest. Alternatively, the techniques may be quantitative, and provide information about the relative amount of the nucleic acid of interest in the sample. For quantitative purposes, quantitative PCR and RT-PCR are preferred. Thus, in one example, RNA is isolated from a sample, and contacted with an oligonucleotide derived from the GIP90/130 polypeptide-encoding nucleic acid sequence, together with reverse transcriptase, under suitable buffer and temperature conditions to produce cDNAs from the GIP90/130 RNA. The cDNA is then subjected to PCR using primer pairs derived from the appropriate nucleic acid sequence disclosed herein. In a preferred embodiment, the primers are designed to detect the presence of the RNA expression product of GIP90/130, and the amount of GIP90/130 gene expression in the sample is compared to the level in a control sample.

For detecting GIP90/130 nucleic acid sequences, standard labeling techniques can be used to label the probe, the nucleic acid of interest, or the complex between the probe and the nucleic acid of interest, including, but not limited to radio-, enzyme-, chemiluminescent-, or avidin or biotin-labeling techniques, all of which are well known in the art. (See, for example, *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.); *PCR Protocols: A Guide to Methods and Applications* (Innis, et al. 1990. Academic Press, San Diego, Calif.)).

Such methods of nucleic acid detection are useful for a variety of purposes, including but not limited to detecting an autoimmune condition, identifying cell division arrest or cell death, identifying cells that express GIP90/130 nucleic acid sequences, in situ hybridization for GIP90/130 gene expression, Northern and Southern blot analysis, and DNA library screening.

As discussed above, GIP90/130 polypeptides are likely to be involved in cell signaling pathways that impair cell division or cause cell death, which are thought to be up-regulated during autoimmune pathogenesis and down-regulated in cancer cells to prevent autoimmune attack during tumor growth. Thus, the detection methods disclosed herein can be used to detect cells that are undergoing such cell death-related processes.

Furthermore, the present invention provides method for treating an autoimmune disorder or cancer comprising modifying the expression or activity of GIP90/130 RNA or GIP90/130 polypeptides, such as by increasing or decreasing their expression or activity. Modifying the expression or activity of GIP90/130 RNA or GIP90/130 polypeptides can be accomplished by using specific inducers or inhibitors of GIP90/130 polypeptide expression or activity, such as GIP90/130 antibodies, polypeptides representing interactive motifs of GIP90/130 such as those disclosed herein, antisense or RNA interference therapy based on the design of antisense oligonucleotides or double stranded RNAs to the GIP90/130 nucleic acid sequences disclosed herein, cell therapy using host cells expressing one or more GIP90/130 polypeptides, or other techniques known in the art. As used herein, "modification of expression or activity" refers to modifying expression or activity of either the RNA or protein product.

For example, knowing that the GIP90/130 gene is a tumor suppressor gene, that aberrantly increased cell death processes are the basis of specific autoimmune pathogenesis (WO 00/50607), and that aggregates of GIP90/130 polypeptides are expressed in a number of human tissues that are common target of autoimmune responses, the administration of GIP90/130 polypeptides or nucleic acids of the invention, particularly those representing essential interactive motifs for GIP90/130 polypeptide aggregation and/or interaction with other cellular components, such as GPBP, would impact pathogenesis and therefore serve as therapeutic agents for autoimmunity. Alternatively, tumor cells express little or no GPBP or GIP90/130, and thus the administration of the GIP90/130 polypeptide or nucleic acid sequences of the invention, particularly the full length GIP90, GIP130a, GIP130b, and/or GIP130c, alone or in combination with GPBP, is expected to provide a therapeutic benefit in patients with cancer.

While not being limited to any specific mechanism of action, it is believed that a therapeutic benefit in cancer patients would be derived by promoting GIP90/130 interactions with other cellular constituents, such as GPBP and/or GIP90/130 aggregation, whereas a therapeutic benefit to autoimmunity patients would be derived by inhibiting these interactions and/or aggregation.

In another aspect, the invention provides methods for modifying GIP90/130 activity comprising contacting cells with an amount effective of one or more of the polypeptides, antibodies, nucleic acids, or pharmaceutical compositions thereof, of the invention to modify GIP90/130 activity. Such cell contacting can be in vitro or in vivo, and "modifying" includes both increasing or decreasing GIP90/130 activity, including transcription-promoting activity.

In another aspect, the invention provides methods for modifying GPBP activity, comprising contacting cells with an amount effective of one or more of the polypeptides, antibodies, nucleic acids, or pharmaceutical compositions thereof, of the invention to modify GPBP activity. Such cell contacting can be in vitro or in vivo, and "modifying" includes both increasing or decreasing GPBP activity. For example, augmented GPBP activity is associated with autoimmunity, and thus the administration of the GIP90/130 polypeptides or antibodies of the invention (or gene therapy by administration of the GIP90/130 nucleic acid sequences or vectors thereof of the invention) would be expected to impact GPBP-GIP90/130 interactions, and to provide a therapeutic benefit in patients with an autoimmune disorder. Alternatively, tumor cells express little or no GPBP, and thus the co-administration of the GIP90/130 polypeptides of the invention, particularly the full length GIP90, GIP130a, GIP130b, and/or GIP130c, in combination with GPBP, would be expected to provide a therapeutic benefit in patients with cancer.

In another aspect, the present invention provides methods for modifying pol κ76 polypeptide activity, comprising contacting cells with an amount effective of one or more of the polypeptides, antibodies, nucleic acids, or pharmaceutical compositions thereof, of the invention to modify pol κ76 activity. Such cell contacting can be in vitro or in vivo, and "modifying" includes both increasing or decreasing pol κ76 activity. For example, augmented pol κ76 activity is associated with autoimmunity (WO 02/46378), and thus the administration of the GIP90/130 polypeptides or antibodies of the invention (or gene therapy by administration of the GIP90/130 nucleic acid sequences or vectors thereof of the invention) would be expected to impact pol κ76-GIP90/130 interactions, and to provide a therapeutic benefit in patients with an autoimmune disorder.

In practicing the therapeutic methods of the invention, the amount or dosage range of the GIP90/130 polypeptides or antibodies thereto generally ranges between about 0.01 μg/kg body weight and about 10 mg/kg body weight, preferably ranging between about 0.10 μg/kg and about 5 mg/kg body weight, and more preferably between about 1 μg/kg and about 5 mg/kg body weight.

In a further aspect, the present invention provides pharmaceutical compositions, comprising an amount effective of the GIP90/130 polypeptides, antibodies thereto, and nucleic acids disclosed herein to carry out one or more of the therapeutic methods of the invention, and a pharmaceutically acceptable carrier. The GIP90/130 polypeptides, or antibodies thereto, may be subjected to conventional pharmaceutical operations such as sterilization and/or may contain conventional adjuvants, such as preservatives, stabilizers, wetting agents, emulsifiers, buffers etc.

For administration, the polypeptides are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The polypeptides or pharmaceutical compositions thereof may be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. In preferred embodiments, the polypeptides are administered intravenously or subcutaneously.

The polypeptides may be made up in a solid form (including granules, powders or suppositories) or in a liquid form (e.g., solutions, suspensions, or emulsions). The polypeptides of the invention may be applied in a variety of solutions. Suitable solutions for use in accordance with the invention are sterile, dissolve sufficient amounts of the polypeptides, and are not harmful for the proposed application.

The present invention may be better understood with reference to the accompanying examples that are intended for purposes of illustration only and should not be construed to limit the scope of the invention, as defined by the claims appended hereto.

EXAMPLES

Identification and Characterization of GIP90/130 Polypeptides

We performed a yeast two-hybrid screening on several human cDNA libraries searching for GPBP-interactive proteins. The screenings were performed using full length GPBP as bait, cloned in vector pGBT9 to generate the GAL4 binding domain-fusion protein. With the resulting construct we transformed yeast HF7c cells to obtain a stably transfected cell line which was subsequently transformed with the different cDNA libraries we have used: Human Skeletal Muscle (pGAD10 vector), Human Kidney (pGAD10), Human Pancreas (pGAD10), Human Brain (pACT2) and Hela (pGADGH) cDNA libraries (all from Clontech). The transformations were carried out according to the supplier's instructions and plated on medium deficient in Trp, Leu and His containing 20 mM 3-amino-1,2,4-triazol. Interactions were assessed following the manufacture's recommendations. Specifically β-galactosidase activity was assayed with X-GAL (0.75 mg/ml) for the lift colony assays and with ortho-nitrophenyl β-D galactopyranoside (0.66 mg/ml) for the in-solution determinations.

We isolated an 800 bp cDNA ("I-20 cDNA") encompassing an open reading frame (ORF) which encodes a 265 residue polypeptide, I-20 (SEQ ID NO:6); from a human skeletal muscle library. Part of the ORF coincided with the ORF encoding DOC1 (down-regulated in ovarian cancer 1) (GenBank accession NP_055705) (Mok et al., Gynecol. Oncol. 52(2):247–252 (1994)), a polypeptide whose encoding mRNA is not found in ovarian cancer cell lines, but is abundantly expressed in normal ovarian cell lines. For this reason, the DOC-1 gene is considered to be a tumor suppressor gene.

Using the I-20 cDNA, we probed a multi-tissue Northern blot (Clontech) to determine the level of expression of the I-20 encoding mRNA in normal human tissues and in a number of human cancer cell lines. The membranes were hybridized with $^{32}P$-α-dCTP labelled I-20 cDNA (SEQ ID NO:5), and specific mRNAs species were identified by autoradiography. We identified four mRNA species of 9, 4.4, 4 and 3 Kb. The species of 9, 4.4 and 3 Kb were more abundant in skeletal muscle, while the 4 Kb species displayed similar expression in skeletal muscle, pancreas and lung, and higher expression in heart tissue. With the exception of heart, which contained traces of the 9, 4.4 and 3 Kb species, the rest of the tissues tested mainly expressed the 4 Kb mRNA species. As expected from previous studies for DOC1, I-20 cDNA did not hybridize significantly to any mRNA species from the individual human cancer cell lines tested (MTN human cancer cell line blot from Clontech), thus confirming I-20 as being encoded by a tumor suppressor gene.

Since the I-20 ORF contained no stop codon and extended 5' past the ORF proposed for DOC1, we explored the possibility that in skeletal muscle I-20 represents a partial sequence of a larger protein. By probing the corresponding cDNA library with the I-20 cDNA, we isolated and characterized by nucleotide sequencing four overlapping cDNA clones which in total comprise an ORF encoding a predicted 764-amino acid polypeptide of 90 kDa that was named GIP90 (SEQ ID NO:10), for GPBP interacting protein 90 kDa. The existence of GIP90 mRNA was confirmed by isolating and nucleotide sequencing a continuous PCR fragment derived from the same library containing the proposed overlapping ORF. The more remarkable structural features of GIP90 are the presence of two nuclear localization signals (NLS), one in the N terminal region and another at the C terminal region, and a highly predictable coiled-coil formation through most of its sequence including two leucine zippers.

Using the cDNA nucleotide sequence of GIP90 ("GIP90 cDNA") (SEQ ID NO: 9) we carried out a BLAST search against the human genome and found that GIP90 cDNA matched at chromosome 3 (3q12) (genomic DNA accession numbers NT_030634 for exon I and NT_033050 for the rest of the exons). We determined the exon/intron structure for the GIP90 genomic sequence, which encompass a total of six exons (FIG. 1). Exons I–IV of the GIP90 gene contain 5' untranslatable sequence and encode the first 201 residues of an N-terminal segment of 240 residues that is absent in DOC1 and DOC1-related protein (GenBank accession number AAH27860). Exon V encodes the remaining 39 residues not present in DOC proteins as well as the additional 524-residues of GIP90, and exon VI contains 3' untranslatable sequence.

Comparison of the GIP90 cDNA and the GIP90 genomic sequence revealed the existence of an adenine (A) at position 2720 ($A^{2720}$) in the GIP90 cDNA that was not present in the GIP90 genomic DNA, suggesting that GIP90 cDNA represents either a cDNA artifact, or a native mRNA species that derives from a DNA polymorphism or mRNA editing. Mutational artifacts are generally unique events unlikely to be found in more than one cDNA molecular species. We have identified $A^{2720}$ in at least two different GIP90 cDNA fragments, representing two different reverse transcription events, and PCR on total cDNA from the human muscle library (Clontech) using a forward primer from exon I and a reverse primer from exon VI, and subsequent direct sequencing, revealed that the resulting cDNA exclusively contained $A^{2720}$. A homologous nucleotide was also found in a DOC1 encoding sequence, but not in DOC1-related protein encoding sequences. These results indicate that the $A^{2720}$ in the GIP90 cDNA does not represent an artifact.

In order to further analyze the origin of GIP90 cDNA, we studied the expression of GIP90 in two independent human skeletal muscle tissue samples by RT-PCR. We were unable to amplify GIP90 mRNA from these samples. In contrast, we isolated and characterized a continuous cDNA fragment (SEQ ID NO: 11) representing a related mRNA species that encodes a 130 kDa polypeptide (1135-residues) that we named GIP130a (SEQ ID NO:12). GIP130a results from faithful transcription and translation of the GIP90 genomic sequence (ie: no $A^{2720}$), suggesting that a specific mechanism for mRNA diversification is responsible for the production of GIP90 encoding mRNA from the GIP90 genomic sequence.

To further explore the mRNA diversification mechanism of the DOC1/GIP90/130 family, we compared the nucleotide sequences encoding DOC1/DOC1-related protein, GIP90, and GIP130a. Several nucleotide differences were identified, namely: (1) DOC-1 and DOC1-related mRNA are devoid of exon I–IV; (2) DOC1 mRNA showed nucleotide deletions of 42- and 18-bp in exon V, and both DOC1 and DOC1-related mRNA contain an additional 276-bp at the 3' end of this exon, which corresponds to an intron sequence in GIP90/130a; (3) DOC-1 and DOC1-related mRNAs are both devoid of exon VI.

Therefore, it appeared that the expression of exon VI is associated with expression of GIP90/130a mRNAs, and that DOC-1 and DOC1-related mRNAs are exclusively encoded by an intron-extended exon V. The existence of DOC-1 mRNAs containing exons I–IV was then assessed by PCR of mRNA from human skeletal muscle and from human 293 cells. We obtained two different cDNAs (SEQ ID NOS: 13 and 15) both containing exon I–V sequences and DOC-1 exclusive exon V, and diverging with respect to each other in one single nucleotide (A/G) at position 975, which leads to an amino acid change at position 168 ($H^{168}/R^{168}$). This results in two different 1133-residue long polypeptides (130-kDa) which we named GIP130b (SEQ ID NO: 14) and GIP130c (SEQ ID NO: 16), respectively. A comparison of the amino acid sequences of GIP90/130 polypeptides and the DOC1 polypeptide family is shown in FIG. 3.

The amino acid sequence of rat filamin A-interacting protein (FILFP) (Genbank accession number BAC00851) and hypothetical human KIAA1275 protein (Genbank accession number BAA86589) are highly homologous (approximately 50%) to the GIP90/130 and DOC proteins. This suggests that these genes are related and that FILIP, KIAA1275 and GIP90/130 are likely to share biological functions. Therefore, knowing that FILIP impairs cell migration of cortical neurons (Nature Cell Biology 2002 July; 4(7): 495–501), it is plausible to hypothesize that GIP90/130 polypeptides exert their tumor suppressor activity, at least in part, by impairing cell migration.

The above data demonstrate that the DOC-1/GIP90/130 mRNA family results from a complex diversification mechanism operating on the expression of the corresponding gene (GIP90 genomic sequence). Thus, we have found that the presence of $R^{168}$ or $H^{168}$ is the result of a GIP90 genomic sequence polymorphism. The presence of exon V, which is characteristic of GIP90/GIP130a (exon Va), is linked to the expression of exon VI and represents a complex alternative exon splicing in which the alternative use of two 5' splice sites of an intron is coordinated with the splicing of an alternative 3+ terminal exon. Thus, when the more upstream 5' splice site is used to yield a shorter exon V (exon Va), the 3' terminal exon (exon VI) is spliced, whereas when using the more downstream 5' splice site resulting in a larger exon V (exon Vb), the 3' terminal exon (exon VI) is not spliced. Regarding $A^{2720}$, we still are in the process of determining the specific diversification mechanism responsible for its presence. The exon/intron structure of the gene for the DOC-1/GIP90/130 family is shown in FIG. 1 and a scheme for the more relevant features regarding mRNA and protein structure for the GIP family is presented in FIG. 2. Finally, similar genetic diversification mechanisms perhaps are responsible for the deletion of $C^{2708}$ in DOC1 and an aberrant alternative splicing within long exons (previously described for other genes) appears to account for the 42- and 18-bp deletions found in DOC1 mRNA.

Figure 2:
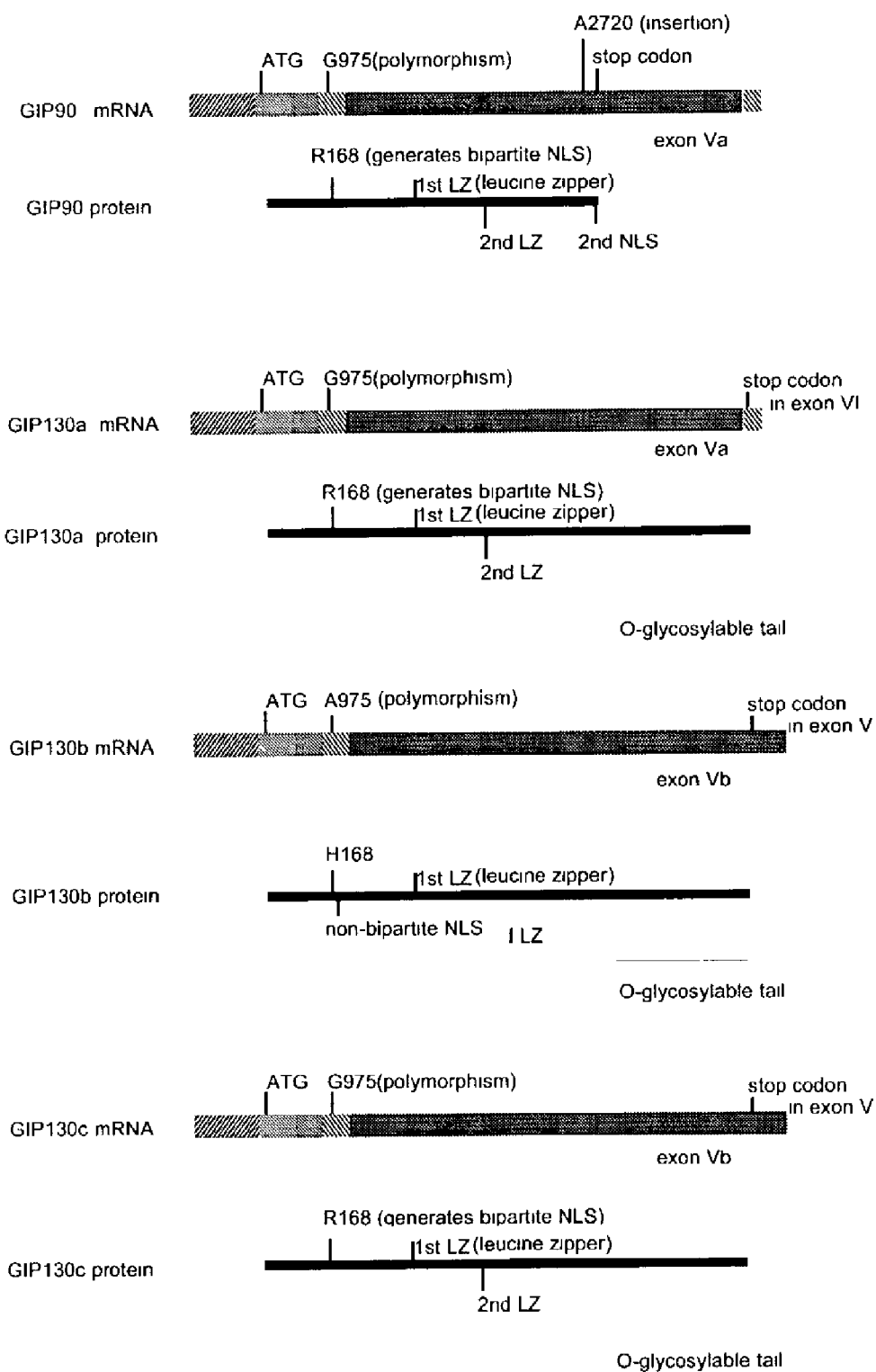
FIG. 2 is a representation of differences between various GIP90/130 mRNA and polypeptide species.

The presence of $R^{168}$ in GIP90 generates a putative bipartite NLS signal and a consensus for PKA phosphorylation, whereas the presence of $A^{2720}$ causes a frame-shift in the ORF encoding GIP90, which results in the appearance of a second nuclear localization signal and a premature stop codon. The latter removes a total of 386 residues of the C terminal region that is present in GIP130 proteins. These residues appear to conform to a domain with no predictable coiled-coils containing a number of putative O-glycosylation sites (FIG. 2).

Characterization of GIP90/130 Interactions

Using a yeast two-hybrid system, we found that the four members of the GIP90/130 interact with GPBP, although to a more limited extent than I-20 (SEQ ID NO:6). GIP90 displayed the strongest interaction with GPBP, whereas individual GIP130 proteins interacted similarly with GPBP, although to a lesser extent than GIP90. These data implicate the C-terminal residues of the GIP130 proteins, which are not present in GIP90, and also the C-terminal residues of GIP90 not present in I-20 in a negative modulation of the interaction of GIP90/130 polypeptides with GPBP. Deletion of the N terminal 240-residues of GIP90, GIP130b, and GIP130c resulted in molecular species that do not interact with GPBP, indicating that the N-terminal region contains residues involved in the interaction of GIP90/130 polypeptides with GPBP. All of these findings account for the observation that I-20 (SEQ ID NO: 6), which contains the bulk of this N terminal region (residues 86–240), and does not harbor the inhibitory C terminal regions, displayed the strongest interaction in a two hybrid system with GPBP. The production of additional I-20 deletion mutants and their use in specific two hybrid studies permitted the identification of two specific regions of I-20 that are essential for GPBP interaction as well as the identification of other residues directly involved but not essential for the interaction (FIG. 4).

GIP90/130 polypeptides self-aggregate and aggregate with each other in a yeast two-hybrid assays, indicating that, similarly to GPBP (WO 00/50607), GIP90/130 polypeptides aggregate to form homo and hetero oligomers. No significant differences were found among GIP90/130 full length polypeptides in their ability to self-aggregate. Deletion of the N-terminal 240-residues from GIP130b/c results in DOC1-related protein, which aggregates more efficiently and does not interact with GPBP. Since the deleted residues contain motifs for I-20 self-aggregation, it is conceivable that the deleted region contains residues that are critical for GIP90/130 aggregation, but not for DOC/DOC1-related protein aggregation, and that GIP90/130 polypeptides and DOC1 polypeptides aggregate in a different manner. Since the N terminal 240 residues also contain essential residues for GIP90/130 polypeptide interactions with GPBP, this further suggests that GPBP interaction negatively modulates GIP90/130 polypeptide aggregation but not DOC aggregation. Consistently, two hybrid assays using I-20 deletion mutants show that essential sequences for GIP90/130 interactions with GPBP and for I-20 aggregation overlap extensively (FIG. 4), strongly suggesting that GPBP binding to GIP90/130 polypeptides prevents GIP90/130 polypeptide aggregation but not DOC aggregation. Accordingly, we have observed with a yeast three-hybrid system that GPBP expression efficiently impairs both I-20 and GIP90 aggregation, and that I-20 and GIP90 efficiently impair GPBP aggregation.

Deletion mutants were obtained using specific primers and PCR, followed by cloning of the resulting cDNAs in the pGBT9 and pGAD424 vectors. The assays were performed in SFY526 or HF7c Saccharomyces cerevisiae strains, with pGBT9 as GAL4 binding domain vector and pGAD424 as GAL4 activation domain vector, by the lift colony assay procedure. Briefly, the yeast cells were co-transformed with constructs of both binding domain and activation domain vectors, and the co-transformants were selected in medium deficient in both tryptophan and leucine. After five days of incubation at 30° C. the colonies were tested for the expression of β-galactosidase with X-Gal substrate (0.75 mg/ml). The intensity of the blue color displayed in the assay informed us about the relative strength of the interactions. When the assays were performed with the HF7c strain, the interactions were assessed by the lift colony assay procedure and by growth in medium deficient in histidine, tryptophan and leucine. For yeast three-hybrid system, we used the pBRIDGE vector, which allows the conditional expression of a third protein apart from the usual GAL4 binding and activation domain-fusion proteins of the two-hybrid system. In this case, the expression of GPBP or I-20 or GIP90 was driven by Met25 promoter, active in absence of methionine. In these experiments, the transformed SFY526 cells were plated in medium deficient in tryptophan, leucine and methionine, and subjected to the colony lift assay after five days at 30° C. In the case of the strain HF7c the colonies grown in the cited plates were streaked on medium with the additional deficiency of histidine.

In an attempt to establish the viability of these molecular interactions in human cells, the interaction between GIP90 and GPBP was assessed in a mammalian two-hybrid system using 293 cells. We used the CLONTECH mammalian two hybrid kit, with vectors pM and pRK5-GAL4BD as GAL4 binding domain vectors and pVP16 as activation domain vector. We transfected 293 cells by the calcium phosphate procedure with the appropriate constructs and reporter vectors and the interactions determined by the CAT ELISA kit (Roche), following the manufacturer's instructions.

Finally, using a yeast two hybrid system, we investigated the interactions between pol κ/pol κ76 and GPBP/GPBPΔ26 and we got no positive results. However, when we challenged interaction between pol κ or pol κ76 and I-20, we obtained positive results with pol κ76 but not with pol κ. The positive interaction of I-20 with pol κ76 suggests that GIP90 is a biological bridge between GPBP and pol κ76 and that the three proteins are partners in specific strategies which become deregulated during autoimmune pathogenesis.

From all these data, we conclude that: (1) GIP90/130 polypeptides aggregate in a different manner than DOC/DOC1-related polypeptides; (2) GPBP interacts with GIP90/130 polypeptides and this interaction counteracts GIP90/130 polypeptide aggregation; (3) GPBP does not interact with DOC/DOC1-related proteins, and therefore GPBP is not expected to influence DOC/DOC1-related protein aggregation; (4) I-20 contains essential amino acid sequences involved in GPBP interaction with GIP90/130 polypeptides and in GIP90/130 polypeptide aggregation; (5) the C terminal domain of GIP130 species exerts a negative effect on their interactions with GPBP, and (6) GIP90/130 polypeptides contain sequences not present in I-20 that negatively modulate both GIP90/130 polypeptide interaction with GPBP and GIP90/130 polypeptide aggregation.

Further Characterization of GIP90/130

Given that GPBP is a protein kinase, we assessed the capacity of GPBP to phosphorylate GIP90 in vitro by using purified yeast recombinant counterparts. GIP90 was cloned in pHIL-D2 vector in frame with the FLAG tag at N-terminal position and with a 6 histidine tail at C-terminal position. It was expressed in the Pichia pastoris expression system (Invitrogen) and purified with an affinity resin (Clontech) making profit of the polyhistidine tail, using an 8 M urea-containing breaking buffer, which was eliminated by dialysis against Tris-buffered saline. The purified protein was incubated with yeast recombinant GPBP in a suitable reaction buffer and labelled for 12 hours at 30° C. The phosphorylation mixtures were analysed by Western blot using FLAG-specific antibodies (Sigma) and autoradiography. Incubation of purified GIP90 and GPBP in the presence of [γ$^{32}$P] ATP resulted in $^{32}$P incorporation into GIP90, thus confirming that GPBP interacts with GIP90 and phosphorylates it.

Remarkable structural features of GIP90/130 proteins are (1) the existence of two nuclear localization sequences (NLS) whose presence appears to be regulated by single nucleotide replacement or addition (see above); and (2) the existence of a large number of predictable coiled-coil motifs including two leucine zippers. Consequently we have assayed the ability of GIP90/130 and DOC1-related protein to induce transcription from a heterologous promoter of a reporter gene. This was accomplished by fusing either GIP90, GIP130a, GIP130b or DOC1-related protein to the binding domain of GAL4 transcription factor in a high level expression pAS2-1 vector (Clontech) and transforming SFY526 yeast cells carrying a LacZ reporter gene under the control of a promoter with a GAL4 binding site. Transformants were selected in tryptophan-deficient medium at 30° C. for five days and colony lift assays performed. The GIP90, GIP130a, and GIP130b fusion polypeptides, but not DOC1-related protein fusion polypeptides, efficiently induced expression of LacZ, as estimated by the appearance of β-galactosidase activity.

We have also expressed GIP90 in bacteria, and have used the corresponding recombinant protein to immunize both rabbits and mice to obtain respectively polyclonal and monoclonal antibodies specific for GIP proteins. GIP90 was cloned in pGEX vector, in frame with glutathione-S-transpherase cDNA. The resulting construct was used to transform DH5α cells and expression of the GST-GIP90 fusion protein was induced with IPTG and further purified on glutathione affinity column. GST-GIP90 purified protein was used to immunize both rabbits and mice in order to obtain respectively polyclonal and monoclonal antibodies. These antibodies were used to identify a native protein in 293 cells displaying the same mobility as recombinant GIP130 which likely represents endogenous GIP130b or GIP130c, since exon VI appears to not be expressed in these cells, as determined by specific RT-PCR approaches. One of the monoclonal antibodies (Mab3) maps in the N terminal 240 residues of GIP90, whereas Mab 8 maps within the next 509 residues (i.e.: between residues 241–750).

By indirect immunofluorescence on COS-7 cells transiently expressing recombinant GIP90 we have identified cells that expressed GIP90 in the nucleus, cells expressing GIP90 in the cytosol, and cells that expressed GIP90 in both the nucleus and the cytosol. When these cells co-expressed recombinant GIP90 and GPBP, double indirect immunofluorescence revealed expression of the two proteins at the cytosol and in some cells GIP90 was also detected in the nucleus. We have not seen GIP90 and GPBP being co-expressed in the nucleus. Finally, using confocal microscopy and NIH3T3 or 293 cells, we have confirmed nuclear localization of GIP90 and cytosolic co-localization GIP90/GPBP. These cells do not express detectable levels of GIP90/130 polypeptides, as no significant fluorescence was detected when non-transfected cells were incubated with anti-GIP antibodies and an appropriate secondary antibody. For immunofluorescence and confocal microscopy studies, GIP90 cDNA was cloned in pRK5 mammalian expression vector, and this construct was used alone or co-transfected with GPBP cloned in pCDNA3 vector (Invitrogen), using the DEAE-dextran or calcium phosphate procedures. After 24 hours of incubation at 37° C., the cells were washed with phosphate-buffered saline (PBS), fixed with methanol or methanol:acetone, blocked with 3% BSA in PBS and incubated with a pool of mouse anti-GIP90 monoclonal antibodies and rabbit anti-GPBP polyclonal antibodies. FITC-conjugated anti-mouse IgG and TRITC-conjugated anti-rabbit IgG antibodies were respectively used as secondary antibody.

Finally, we have performed immunohistochemistry studies on paraffin embedded human tissues and have found GIP proteins to localize in a number of cells and structures also expressing GPBP. Immunohistochemistry studies were done on human multi-tissue control slides (Biomeda, Dako), using the ABC peroxidase method. GIP proteins are widely expressed in human tissues, but are more abundantly expressed in some locations. A strong staining is found in smooth muscle cells, particularly in those of vessel walls, with a diffuse cytoplasmic pattern. There is intense expression in alveolar septa, with a linear pattern suggestive of being associated to basement membrane locations, along with cytoplasmic staining of the pneumocytes. The kidneys show expression in the epithelial cells of the tubules, mainly in distant ones, and also in mesangial cells and podocytes of the glomerulus. In the pancreas there is staining in the cells of endocrine Langerhans islets. In the adrenal gland, the cortical cells show higher expression than the medullar cells. In the liver, hepatocytes show expression of the GIP90/130, which is higher at the epithelial cells of the biliary ducts. The white matter of the central nervous system shows diffuse staining with a fibrillar pattern, with presence also found in some neuronal bodies. Expression of the GIP90/130 is also evident at the epithelial cells of the prostate, breast, bronchi and intestine, in striated muscle cells of the myocardium, in secretory cells of the pituitary, and in spermatogonium and Leydig cells in the testicle.

The expression of the GIP90/130 is quite similar to that previously described for GPBP (WO 00/50607), with staining in tissues targeted by autoimmune responses, such as the Langerhans islets (type I diabetes), the white matter of the central nervous system (multiple sclerosis), the biliary ducts (primary biliary cirrhosis), the cortex of the adrenal gland (Addison disease), alveolar septa (Goodpasture syndrome), and spermatogonium (male infertility).

The evidence suggests that GIP90/130 is a family of proteins encoded by a tumor suppressor gene, which display transcription factor activity, and which interact and are phosphorylated by GPBP. Given the role of GPBP in autoimmune pathogenesis and in cancer, GIP90/130 represent a potential therapeutic or therapeutic target in these disorders.

We claim:

1. An isolated polypeptide comprising the amino acid sequence of SEQ ID NO:6.

2. The isolated polypeptide of claim 1 consisting of the amino acid sequence of SEQ ID NO:6.

3. A composition comprising:
a) an isolated polypeptide according to claim 1; and
b) a pharmaceutically acceptable carrier.

* * * * *